US009645146B2

(12) United States Patent
Rakestraw et al.

(10) Patent No.: US 9,645,146 B2
(45) Date of Patent: *May 9, 2017

(54) CELL SURFACE DISPLAY, SCREENING AND PRODUCTION OF PROTEINS OF INTEREST

(71) Applicant: Agenus Inc., Lexington, MA (US)

(72) Inventors: James A. Rakestraw, Cambridge, MA (US); Stan I. Letovsky, Canton, MA (US); Shaun Lippow, San Francisco, CA (US)

(73) Assignee: Agenus, Inc., Lexington, MA (US)

( * ) Notice: Subject to any disclaimer, the term of this patent is extended or adjusted under 35 U.S.C. 154(b) by 209 days.

This patent is subject to a terminal disclaimer.

(21) Appl. No.: 14/226,114

(22) Filed: Mar. 26, 2014

(65) Prior Publication Data

US 2014/0357508 A1    Dec. 4, 2014

Related U.S. Application Data

(62) Division of application No. 12/056,264, filed on Mar. 26, 2008, now Pat. No. 8,709,980.

(Continued)

(51) Int. Cl.
*C40B 30/04* (2006.01)
*G01N 33/566* (2006.01)
(Continued)

(52) U.S. Cl.
CPC ....... *G01N 33/566* (2013.01); *C12N 15/1037* (2013.01); *C40B 10/00* (2013.01);
(Continued)

(58) Field of Classification Search
None
See application file for complete search history.

(56) References Cited

U.S. PATENT DOCUMENTS

| 5,223,409 A | 6/1993 | Ladner |
| 5,252,466 A | 10/1993 | Cronan, Jr. |

(Continued)

FOREIGN PATENT DOCUMENTS

| WO | 98/15833 | 4/1998 |
| WO | WO03/102196 | 12/2003 |

(Continued)

OTHER PUBLICATIONS

Asai, T., et al. "A human biotin acceptor domain allows site-specific conjugation of an enzyme to an antibody-avidin fusion protein for targeted drug delivery," Biomolecular Engineering, 21: 145-155, Feb. 2005.

(Continued)

*Primary Examiner* — Christian Boesen
(74) *Attorney, Agent, or Firm* — Greenberg Traurig, LLP; Natalie Salem

(57) ABSTRACT

Aspects of the invention provide compositions and methods for displaying engineered polypeptides on a cell surface. According to aspects of the invention, immobilized polypeptides can be screened to identify one or more variants having one or more functional or structural properties of interest. Aspects of the invention provide composition and methods for producing engineered protein or protein variants having a functional or a structural property of interest.

17 Claims, 25 Drawing Sheets

Related U.S. Application Data

(60) Provisional application No. 60/920,375, filed on Mar. 26, 2007, provisional application No. 60/920,378, filed on Mar. 26, 2007, provisional application No. 60/959,719, filed on Jul. 16, 2007, provisional application No. 61/004,841, filed on Dec. 1, 2007.

(51) Int. Cl.

| | | |
|---|---|---|
| *C12N 15/10* | (2006.01) | |
| *C40B 10/00* | (2006.01) | |
| *C40B 40/02* | (2006.01) | |
| *C40B 40/08* | (2006.01) | |

(52) U.S. Cl.
CPC ............. *C40B 40/02* (2013.01); *C40B 40/08* (2013.01); *C07K 2319/035* (2013.01); *C40B 30/04* (2013.01); *G01N 2333/705* (2013.01)

(56) References Cited

U.S. PATENT DOCUMENTS

| | | |
|---|---|---|
| 5,348,867 A | 9/1994 | Georgiou et al. |
| 5,403,484 A | 4/1995 | Ladner |
| 5,571,698 A | 11/1996 | Ladner |
| 5,723,584 A | 3/1998 | Schatz |
| 5,837,500 A | 11/1998 | Ladner |
| 5,866,344 A | 2/1999 | Georgiou et al. |
| 5,874,239 A | 2/1999 | Schatz |
| 5,932,433 A | 8/1999 | Schatz |
| 5,948,635 A | 9/1999 | Kay et al. |
| 6,027,910 A | 2/2000 | Klis |
| 6,057,098 A | 5/2000 | Buechler |
| 6,114,147 A | 9/2000 | Frenken |
| 6,255,075 B1 | 7/2001 | Huang |
| 6,265,552 B1 | 7/2001 | Schatz |
| 6,300,065 B1 | 10/2001 | Kieke |
| 6,420,113 B1 | 7/2002 | Buechler |
| 6,423,538 B1 | 7/2002 | Wittrup |
| 6,555,310 B1 | 4/2003 | Gray |
| 6,686,168 B1 | 2/2004 | Lok |
| 6,696,251 B1 | 2/2004 | Wittrup |
| 6,699,658 B1 | 3/2004 | Wittrup |
| 6,759,243 B2 | 7/2004 | Kranz et al. |
| 6,919,183 B2 | 7/2005 | Fandl |
| 6,979,538 B2 | 12/2005 | Ladner |
| 7,118,879 B2 | 10/2006 | Ladner |
| 7,125,973 B2 | 10/2006 | Lok |
| 7,132,273 B1 | 11/2006 | Choi |
| 7,166,423 B1 | 1/2007 | Miltenyi |
| 7,192,764 B2 | 3/2007 | Fukuda |
| 7,208,293 B2 | 4/2007 | Ladner |
| 7,435,553 B2 | 10/2008 | Fandl |
| 7,465,787 B2 | 12/2008 | Wittrup et al. |
| 7,569,357 B2 | 8/2009 | Kranz et al. |
| 7,795,411 B2 | 9/2010 | Scholler et al. |
| 8,043,830 B2 | 10/2011 | Barat et al. |
| 8,067,179 B2 | 11/2011 | Georgiou et al. |
| 8,372,636 B2 | 2/2013 | Wittrup et al. |
| 8,709,980 B2 | 4/2014 | Rakestraw et al. |
| 8,722,586 B2 | 5/2014 | Rakestraw |
| 8,741,810 B2 | 6/2014 | Zauderer et al. |
| 8,999,897 B2 | 4/2015 | Samaddar et al. |
| 9,005,927 B2 | 4/2015 | Hufton et al. |
| 9,012,181 B2 | 4/2015 | Hufton et al. |
| 9,040,258 B2 | 5/2015 | Hufton et al. |
| 9,139,637 B2 | 9/2015 | Wittrup et al. |
| 2002/0142355 A1 | 10/2002 | Barry |
| 2003/0100023 A1 | 5/2003 | Iverson et al. |
| 2003/0186374 A1 | 10/2003 | Hufton et al. |
| 2004/0033603 A1 | 2/2004 | Zhang |
| 2004/0072740 A1 | 4/2004 | Iverson et al. |
| 2004/0132133 A1 | 7/2004 | Bennett |
| 2004/0197857 A1 | 10/2004 | Fukuda |
| 2004/0219611 A1 | 11/2004 | Racher |
| 2005/0196743 A1 | 9/2005 | Ostanin |
| 2006/0141540 A1 | 6/2006 | Miltenyi |
| 2007/0258954 A1 | 11/2007 | Iverson et al. |
| 2007/0259417 A1 | 11/2007 | Ladner |
| 2008/0085539 A1 | 4/2008 | Scholler |
| 2008/0090282 A1 | 4/2008 | Binder |
| 2011/0190159 A1 | 8/2011 | Hufton et al. |
| 2011/0281360 A1 | 11/2011 | Hufton et al. |
| 2011/0281761 A1 | 11/2011 | Hufton et al. |
| 2011/0287971 A1 | 11/2011 | Hufton et al. |

FOREIGN PATENT DOCUMENTS

| | | |
|---|---|---|
| WO | WO2005/047317 | 5/2005 |
| WO | WO2008/063310 | 5/2008 |
| WO | WO2008/143684 | 11/2008 |

OTHER PUBLICATIONS

Barker and Campbell "Genetic and biochemical characterization of the birA gene and its product: evidence for a direct role of biotin holoenzyme synthetase in repression of the biotin operon in *Escherichia coli*," J. Mol. Biol., 146:469-492, 1981.

Boder E.T. and Wittrup D.K. "Optimal screening of surface-displayed polypeptide libraries," Biotechnol. Prog., 14: 55-62, 1998.

Boder E.T. and Wittrup D.K. "Yeast surface display for screening combinatorial polypeptide libraries," Nature Biotechnology, 15: 553-557, 1997.

Bohm, E., et al. "Screening for improved cell performance: Selection of subclones with altered production kinetics or improved stability by cell sorting," Biotechnology and Bioengineering, 88(6):699-706, Dec. 20, 2004.

Brunet, E., et al. "A Novel Strategy for the Functional Cloning of Enzymes Using Filamentous Phage Display: the Case of Nucleotidyl Transferases," Nucleic Acids Res, 30:e40, 2002.

Cronan, JE "Biotination of proteins in vivo. A post-translational modification to label, purify, and study proteins," J. of Biological Chemistry, 265:10327-10333, 1990.

Cronan and Wallace "The gene encoding the biotin-apoprotein ligase from S. cerevisiae," FEMS Lett, 130:221-229, 1995.

Chapman-Smith and J.E. Cronan, Jr. "In vivo enzymatic protein biotinylation," Biomol. Eng., 16(16):19-125, 1999.

De Boer, et al. "Efficient biotinylation and single-step purification of tagged transcription factors in mammalian cells and transgenic mice," PNAS, 100(13):7480-7485, 2003.

Dhillon, JK, et al. "Bacterial surface display of an anti-pollutant antibody fragment," Lett Appl Microbiol, 28(5):350-354, 1999.

Etz, et al. "Bacterial Phage Receptors, Versatile Tools for Display of Polypeptides on the Cell Surface," Journal of Bacteriology, 183(23): 6924-6935, Dec. 2001.

Fa, M., et al. "Expanding the Substrate Repertoire of a DNA Polymerase by Directed Evolution," J American Chem. Society, 126: 1748-1754, 2004.

Fall "Analysis of microbial biotin proteins", Methods in Enzymology, 62: 390-398, 1979.

Feldhaus M.J., et al. "Flow-cytometric isolation of human antibodies from a non-immune Saccharomyces cerevisiae surface display library," Nature Biotechnology, 21:163-170, 2003.

Furukawa, et al. "Development of novel yeast cell surface display system for homo-oligomeric protein by coexpression of native and anchored subunits," Biotechnol. Prog., 22: 994-99, 2006.

Gaj, et al. "The AviD•tag, a NeutrAvidin/avidin specific peptide affinity tag for the immobilization and purification of recombinant proteins," Protein Expr. Pur., 56(1):54-61, 2007.

Ghadessy, F., et al. "Directed Evolution of Polymerase Function by compartmentalized Self-replication," PNAS USA, 98:4552-4557, 2001.

Ghaemmaghami, S, et al. "Global analysis of protein expression in yeast," Nature, 425(6959);737-41, 2003.

Guo, et al. "A *Saccharomyces* gene family involved in invasive growth, cell-cell adhesion, and mating," P.N.A.S , 97(22):12158-12163, 2000.

Green, N. M. "Avidin," Adv. Protein Chem., 29:85-133, 1975.

(56) References Cited

OTHER PUBLICATIONS

Ho, M., et al. "Isolation of anti-CD22 Fv with high affinity by Fv display on human cells," PNAS, 103(25): 9637-9642, 2006.
Holmes "Improved cell line development by high throughput affinity capture surface display techniques to select for high secretor," J. Immunol. Methods, 230:141-147, 1999.
Howard P.K., et al. "Nucleotide sequence of the birA gene encoding the biotin operon repressor and biotin holoenzyme synthetase functions of *Escherichia coli*," Gene, 35(3):321-331, 1985.
Jang KH, et al. "Extracellular secretion of levansucrase from Zymomonas mobilis in *Escherichia coli*," Bioprocess Engineering, 21(5): 453-458, 1999.
Jestin, J.L., et al. "A Method for the Selection of Catalytic Activity Using Phage display and Proximity Coupling," Angew Chem. Int Ed Engl., 38:1124-2237, 1999.
Kaderbhai, M. A "Targeting of active human cytochrome P4501A1 (CYPIA1) to the periplasmic space of *Escherichia coli*," Biochem. Biophys. Res. Commun., 279(3):803•807, 2000.
Kim, Y-S, et al. "Directed evolution of the epidermal growth factor receptor extracellular domain for expression in yeast," Proteins, 62(4):1026-1035, Mar. 1, 2006.
Kondo, et al., "Yeast cell-surface display—applications of molecular display," Appl. Microbiol. Biotechnical, 64:28-40, 2004.
Kujau, M.J., et al. "Expression and secretion of functional miniantibodies McPC603scFvDhlx in cell-wall-less L•form strains of *Proteus mirabilis* and *Escherichia coli*: a comparison of the synthesis capacities of L•form strains with an *E. coli* producer strain," Applied Microbial Biotechnology, 49:51•58,1998.
Laitinen OH, et al. "Brave new (strept)avidins in biotechnology," Trends in Biotechnology, 25:269-277, 2007.
Laitinen, OH, et al. "Rational Design of an Active Avidin Monomer," The Journal of Biological Chemistry, 278:4010-4014, 2003.
Lang "Outer Membrane Proteins as Surface Display Systems," Int. J. Med. Microbiol., 290(7):579-585, 2000.
Lenkei, R., et al. "Performance of calibration standards for antigen quantitation with flow cytometry," Cytometry, 33(2):188-196, Oct. 1, 1998.
Levin A.M. and Wales G.A. "Optimizing the affinity and specificity or proteins with molecular display," Mol. BioSyst., 249-257, 2006.
Lin "Display of a functional hetero-oligomeric catalytic antibody on the yeast cell surface," Appl. Microbiol. Biotcchnol., 62:226-236, 2003.
Manz R., et al. "Analysis and Sorting of Live Cells According to Secreted Molecules, Relocated to Cell-Surface Affinity Matrix," PNAS, 92(6):1921-1925, 1995.
Matsumoto, et al. "Construction of Yeast Strains with High Cell Surface Lipase Activity by Using Novel Display Systems Based on the Flolp Flocculation Functional Domain," Applied and Environmental Microbiology, 68(9):4517-4522, 2002.
McCafferty, et al. "Phage antibodies: filamentous phage displaying antibody variable domains," Nature, 348:552-554, 1990.
Mechold, et al. "Codon optimization of the BirA enzyme gene leads to higher expression and an improved efficiency of biotinylation of target proteins in mammalian cells," Journal of Biotechnology, 116(3):245-249, 2005.
Meyer, et al. "Highly selective cyclic peptide ligands for neutravidin and avidin identified by phage display," Chemical Biology & Drug Design, 68:3-10, 2006.
Nordlund, HR, et al. "Construction of a Dual Chain Pseudotetrameric Chicken Avidin by Combining Two Circularly Permuted Avidins," The Journal of Biological Chemistry, 279:36715-36719, 2004.
Nordlund, HR, et al. "Tetravalent single-chain avidin: from subunits to protein domains via circularly permuted avidins," Biochem. J., 392:485-491, 2005.
Ong, J.L. "Directed Evolution of DNA Polymerase, RNA Polymerase, and Reverse Transcriptase Activity in a Single Polypeptide," Jour. Mol. Biol. 361:537-550, 2006.
Parker, MH, et al. "Antibody mimics based on human fibronectin type three domain engineered for thermostability and high-affinity binding to vascular endothelial growth factor receptor two," Protein Engineering Design and Selection, 18(9):435-444, 2005.
Piatesi, A., et al. "Directed evolution for improved secretion of cancer-testis antigen NY-ESO-1 from yeast," Protein Purification and Expression, 48(2):232-242, Aug. 2006.
Rakestraw, J.A. "A Directed Evolution Approach to Engineering Recombinant Protein Production in *S. Cerevisiae*," Thesis (Ph.D.), Massachusetts Institute of Technology, i.-155, May 2006.
Rakestraw, J. A., et al. "A Flow Cytometric Assay for Screening Improved Heterologous Protein Secretion in Yeast," Biotechnology Progress, 22(4):1200-1208, 2006.
Rakestraw, J. A., et al. "Contrasting Secretory Processing of Simultaneously Expressed Heterologous Proteins in *Saccharomyces cerevisiae*," Biotechnology and Bioengineering, 93(5): 896-905, Apr. 2006.
Rakestraw, J.A., et al. "Directed Evolution of a Secretory Leader for the Improved Expresion of Heterologous Proteins and Full-Length Antibodies in *Saccharomyces cerevisiae*," Biotechnology and Bioengineering, 103(6):1192-1201, Aug. 15, 2009.
Samols, et al. "Evolutionary conservation among biotin enzymes," J. Biol. Chem., 263:6461-6464, 1988.
Schatz, et al. "Use of peptide libraries to map the substrate specificity a peptide-modifying enzyme: a 13 residue consensus peptide specifies biotinylation in *Escherichia coli*," Biotechnology, 11:1138-1143, 1993.
Scholler, et al. "Method for the generation of in vivo biotinylated recombinant antibodies by yeast mating," J. Immunol. Methods, 317(1-2):132-143, 2006.
Shusta, et al. "Yeast Polypeptide Fusion Surface Display Levels Predict Thermal Stability and Soluble Secretion Efficiency," J. Mol. Biol., 292:949-956, 1999.
Sergeeva, et al. "Display technologies: Application for the discovery of drug and gene delivery agents," Advanced Drug Delivery Reviews, 58(15):1622-1654, 2006.
Smith, et al. "A plasmid expression system for quantitative in vivo biotinylation of thioredoxin fusion proteins in *Escherichia coli*," Nucleic Acids Research, 26(6):1414-1420, 1998.
Suzuki, et al. "Isolation and characterization of mutations in the human holocarboxylase synthetase cDNA," Nature Genetics 8: 122-128, 1994.
Tawfik DS and Griffiths AD "A Man-made Cell-like Compartments for Molecular Evolution," Nature Biotechnology, 16:652-656, 1998.
Teunissen, A., et al. "Localization of the dominant flocculation genes FL05 and FL08 of *Saccharomyces cerevisiae*," Yeast, 11:735-745, 1995.
Tsao, et al. "A versatile plasmid expression vector for the production of biotinylated proteins by site-specific, enzymatic modification in *Escherichia coli*," Gene, 169: 59-64, 1996.
Van der Wal, F., et al. "Optimization of bacteriocin-release-protein (BRP)-mediated protein release by *Escherichia coli*: extracellular production of the periplasmic molecular chaperone FaeE," Appl. Microbiol. Biotechnol., 44(3-4):459-465, Dec. 1995.
Van der Wal, F., et al. "Optimization of Bacteriocin Release Protein (BRP)-Mediated Protein Release by *Escherichia coli*: Random Mutagenesis of the pC1oDF13-Derived BRP Gene To Uncouple Lethality and Quasi-Lysis from Protein Release," Applied and Environmental Microbiology, 64(2):392-398, Feb. 1998.
Weaver-Feldhaus, J. M., et al. "Directed evolution for the development of conformation-specific affinity reagents using yeast display," Protein Engineering Design and Selection, 18(11):527-536, Nov. 2005.
Worn, et al., "Correlation between in vitro Stability and in vivo Performance of Anti-GCN4 Intrabodies as Cytoplasmic Inhibitors," J. Biol. Chern., 275:2795-2803, 2000.
Xia, G., et al. "Directed Evolution of Novel Polymerase Activities: Mutation of a DNA Polymerase into an efficient RNA Polymerase," PNAS USA, 99:6597-6602, 2002.
Yamano, et al. "In vivo biotinylation of fusion proteins expressed in *Escherichia coli* with a sequence of Propionibacterium freudenreichii transcarboxylase 1.3S biotin subunit," Bioscience, Biotechnology, and Biochemistry, 56(7):1017-1026, 1992.

(56) References Cited

OTHER PUBLICATIONS

Yang, J., et al. "One Hundred Seventy-Fold Increase in Excretion of an FV Fragment-Tumor Necrosis Factor Alpha Fusion Protein (sFV/TNF-alpha) from *Escherichia coli* Caused by the Synergistic Effects of Glycine and Triton X-100," Appl. Environ. Microbiol., 64:2869-2874, 1998.

Zhou, S., et al. "Enhancement of expression and apparent secretion of Erwinia chrysanthemi endoglucanase (encoded by celZ) in *Escherichia coli B*," Applied Environmental Microbiology, 65:2439-2445, 1999.

Van den Beucken et al. "Affinity maturation of Fab antibody fragments by fluorescent-activated cell sorting of yeast-displayed libraries," FEBS Letters 546(2003) 288-294.

European Search Report issued in European Application No. 12154795.4 mailed Jun. 21, 2013.

International Search Report and written Opinion issued for International application No. PCT/US2008/003978 mailed Nov. 9, 2008.

Parrott, M. et al., "Metabolic Biotinylation of Recombinant Proteins in Mammalian Cells and in Mice", Molecular Therapy, vol. 1, No. 1, pp. 96-104, Jan. 2000.

Parrott, M. et al., "Metabolic Biotinylation of secreted and cell surface proteins from mammalian cells", Biochem Biophys Res Commun., 281(4):993-1000; Mar. 9, 2001.

Pepper, L. et al., "A decade of yeast surface display technology: Where are we now?", Comb Chem High Throughput Screen, 11(2), pp. 127-134, Feb. 2008.

Rakestraw, J.A. et al., "Secretion-and-capture cell-surface display for selection of target-binding proteins", Protein Engineering, Design and Selection, 24(6), pp. 525-530, Jun. 2011.

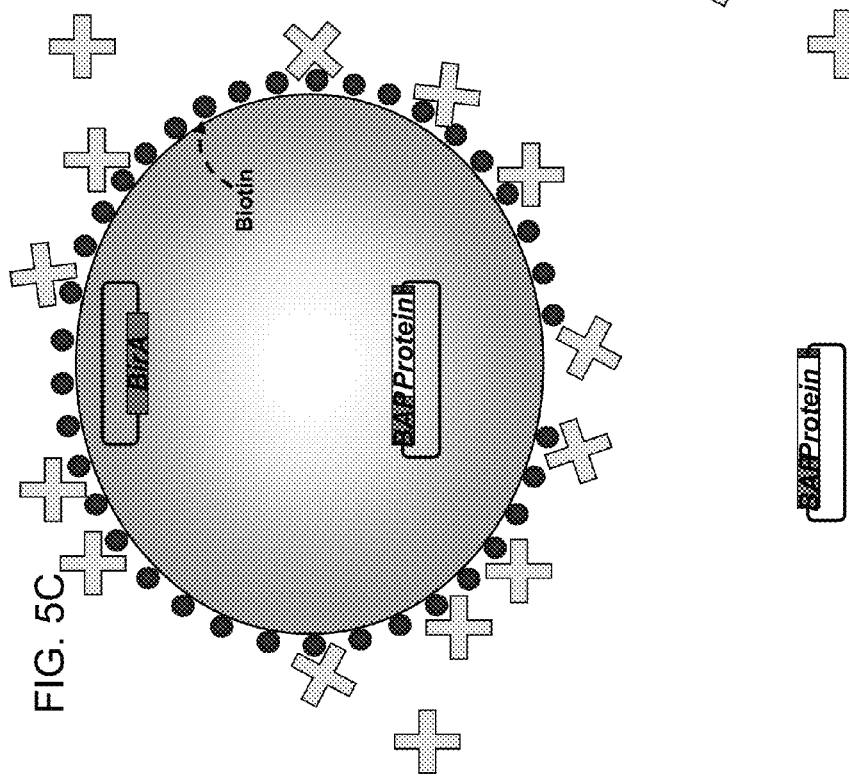
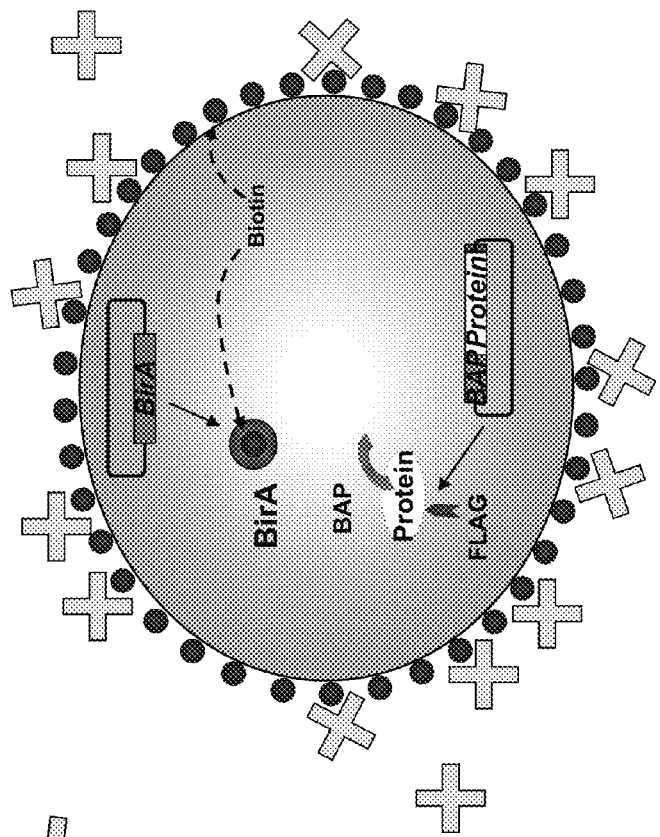
FIG. 5C
FIG. 5D

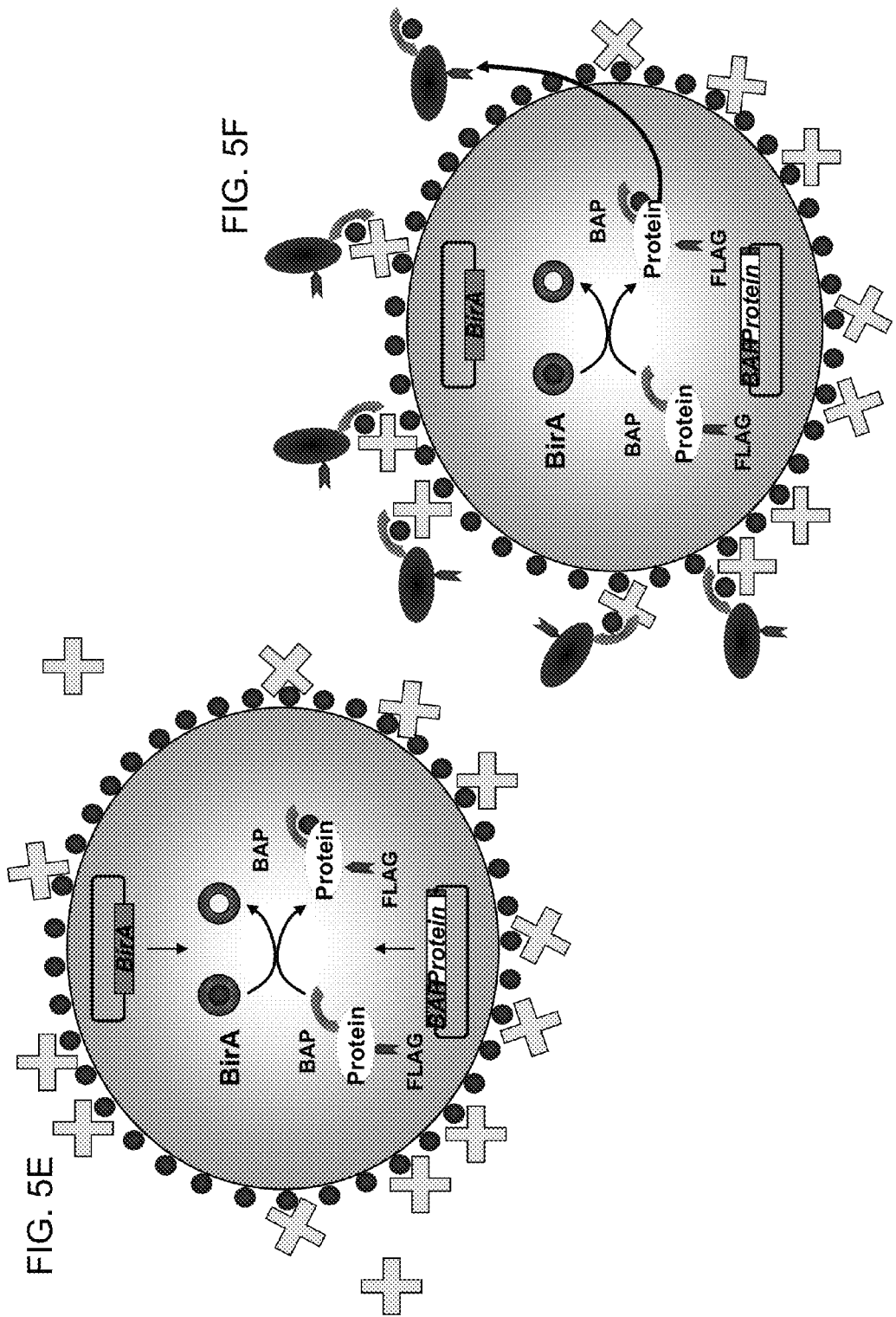

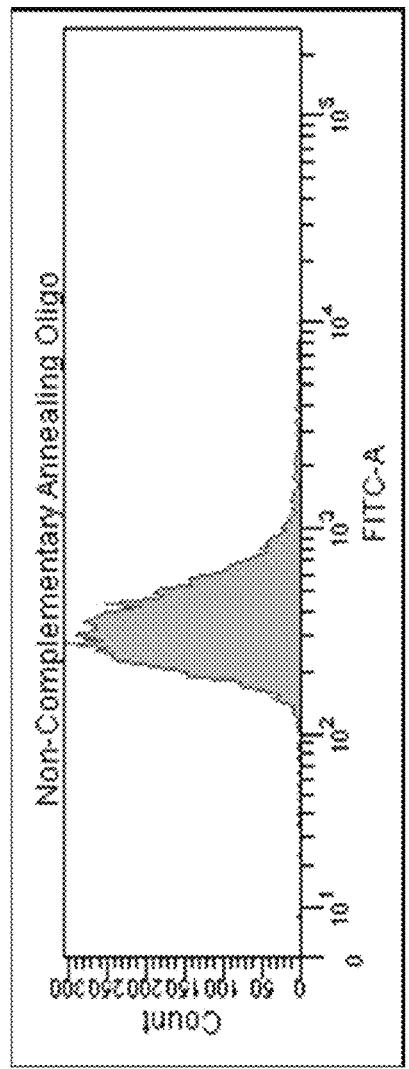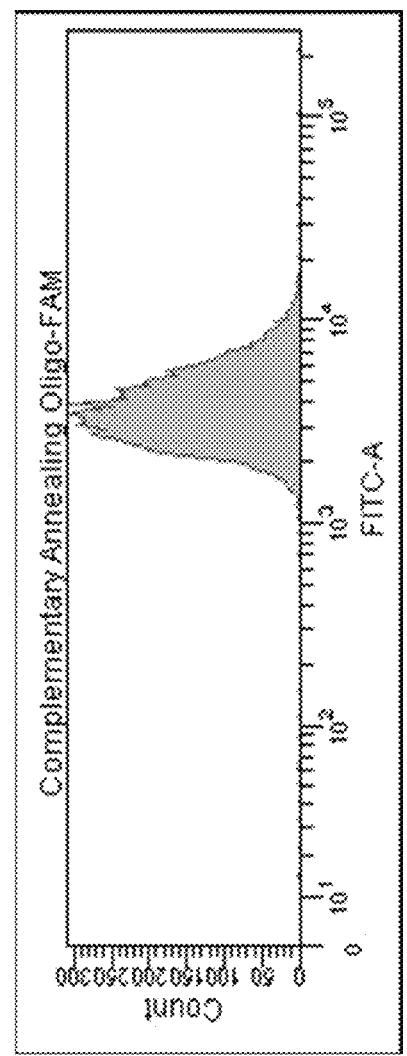
FIG. 14A
FIG. 14B

SEQUENCE LISTING

```
<160> NUMBER OF SEQ ID NOS: 13

<210> SEQ ID NO 1
<211> LENGTH: 321
<212> TYPE: PRT
<213> ORGANISM: Escherichia coli

<400> SEQUENCE: 1

Met Lys Asp Asn Thr Val Pro Leu Lys Leu Ile Ala Leu Leu Ala Asn
1               5                   10                  15

Gly Glu Phe His Ser Gly Glu Gln Leu Gly Glu Thr Leu Gly Met Ser
            20                  25                  30

Arg Ala Ala Ile Asn Lys His Ile Gln Thr Leu Arg Asp Trp Gly Val
```

```
            35                  40                  45
Asp Val Phe Thr Val Pro Gly Lys Gly Tyr Ser Leu Pro Glu Pro Ile
 50                  55                  60

Gln Leu Leu Asn Ala Lys Gln Ile Leu Gly Gln Leu Asp Gly Gly Ser
 65                  70                  75                  80

Val Ala Val Leu Pro Val Ile Asp Ser Thr Asn Gln Tyr Leu Leu Asp
                 85                  90                  95

Arg Ile Gly Glu Leu Lys Ser Gly Asp Ala Cys Ile Ala Glu Tyr Gln
                100                 105                 110

Gln Ala Gly Arg Gly Arg Gly Arg Lys Trp Phe Ser Pro Phe Gly
            115                 120                 125

Ala Asn Leu Tyr Leu Ser Met Phe Trp Arg Leu Glu Gln Gly Pro Ala
            130                 135                 140

Ala Ala Ile Gly Leu Ser Leu Val Ile Gly Ile Val Met Ala Glu Val
145                 150                 155                 160

Leu Arg Lys Leu Gly Ala Asp Lys Val Arg Val Lys Trp Pro Asn Asp
                165                 170                 175

Leu Tyr Leu Gln Asp Arg Lys Leu Ala Gly Ile Leu Val Glu Leu Thr
                180                 185                 190

Gly Lys Thr Gly Asp Ala Ala Gln Ile Val Ile Gly Ala Gly Ile Asn
            195                 200                 205

Met Ala Met Arg Arg Val Glu Glu Ser Val Val Asn Gln Gly Trp Ile
210                 215                 220

Thr Leu Gln Glu Ala Gly Ile Asn Leu Asp Arg Asn Thr Leu Ala Ala
225                 230                 235                 240

Met Leu Ile Arg Glu Leu Arg Ala Ala Leu Glu Leu Phe Glu Gln Glu
                245                 250                 255

Gly Leu Ala Pro Tyr Leu Ser Arg Trp Glu Lys Leu Asp Asn Phe Ile
            260                 265                 270

Asn Arg Pro Val Lys Leu Ile Ile Gly Asp Lys Glu Ile Phe Gly Ile
            275                 280                 285

Ser Arg Gly Ile Asp Lys Gln Gly Ala Leu Leu Leu Glu Gln Asp Gly
            290                 295                 300

Ile Ile Lys Pro Trp Met Gly Gly Glu Ile Ser Leu Arg Ser Ala Glu
305                 310                 315                 320

Lys

<210> SEQ ID NO 2
<211> LENGTH: 321
<212> TYPE: PRT
<213> ORGANISM: Escherichia coli

<400> SEQUENCE: 2

Met Lys Asp Asn Thr Val Pro Leu Lys Leu Ile Ala Leu Leu Ala Asn
 1                   5                  10                  15

Gly Glu Phe His Ser Gly Glu Gln Leu Gly Glu Thr Leu Gly Met Ser
                 20                  25                  30

Arg Ala Ala Ile Asn Lys His Ile Gln Thr Leu Arg Asp Trp Gly Val
            35                  40                  45

Asp Val Phe Thr Val Pro Gly Lys Gly Tyr Ser Leu Pro Glu Pro Ile
 50                  55                  60

Gln Leu Leu Asn Ala Lys Gln Ile Leu Gly Gln Leu Asp Gly Gly Ser
 65                  70                  75                  80

Val Ala Val Leu Pro Val Ile Asp Ser Thr Asn Gln Tyr Leu Leu Asp
```

```
                 85                  90                  95
Arg Ile Gly Glu Leu Lys Ser Gly Asp Ala Cys Ile Ala Glu Tyr Gln
            100                 105                 110

Gln Ala Gly Arg Gly Arg Gly Arg Lys Trp Phe Ser Pro Phe Gly
        115                 120                 125

Ala Asn Leu Tyr Leu Ser Met Phe Trp Arg Leu Glu Gln Gly Pro Ala
        130                 135                 140

Ala Ala Ile Gly Leu Ser Leu Val Ile Gly Ile Val Met Ala Glu Val
145                 150                 155                 160

Leu Arg Lys Leu Gly Ala Asp Lys Val Arg Val Lys Trp Pro Asn Asp
                165                 170                 175

Leu Tyr Leu Gln Asp Arg Lys Leu Ala Gly Ile Leu Val Glu Leu Thr
            180                 185                 190

Gly Lys Thr Gly Asp Ala Ala Gln Ile Val Ile Gly Ala Gly Ile Asn
        195                 200                 205

Met Ala Met Arg Gln Val Glu Glu Ser Val Val Asn Gln Gly Trp Ile
210                 215                 220

Thr Leu Gln Glu Ala Gly Ile Asn Leu Asp Arg Asn Thr Leu Ala Ala
225                 230                 235                 240

Met Leu Ile Arg Glu Leu Arg Ala Ala Leu Glu Leu Phe Glu Gln Glu
                245                 250                 255

Gly Leu Ala Pro Tyr Leu Ser Arg Trp Glu Lys Leu Asp Asn Phe Ile
            260                 265                 270

Asn Arg Pro Val Lys Leu Ile Ile Gly Asp Lys Glu Ile Phe Gly Ile
        275                 280                 285

Ser Arg Gly Ile Asp Lys Gln Gly Ala Leu Leu Leu Glu Gln Asp Gly
        290                 295                 300

Ile Ile Lys Pro Trp Met Gly Gly Glu Ile Ser Leu Arg Ser Ala Glu
305                 310                 315                 320

Lys

<210> SEQ ID NO 3
<211> LENGTH: 321
<212> TYPE: PRT
<213> ORGANISM: Escherichia coli

<400> SEQUENCE: 3

Met Lys Asp Asn Thr Val Pro Leu Lys Leu Ile Ala Leu Leu Ala Asn
1               5                   10                  15

Gly Glu Phe His Ser Gly Glu Gln Leu Gly Glu Thr Leu Gly Met Ser
            20                  25                  30

Arg Ala Ala Ile Asn Lys His Ile Gln Thr Leu Arg Asp Trp Gly Val
        35                  40                  45

Asp Val Phe Thr Val Pro Gly Lys Gly Tyr Ser Leu Pro Glu Pro Ile
    50                  55                  60

Gln Leu Leu Asn Ala Lys Gln Ile Leu Gly Gln Leu Asp Gly Gly Ser
65                  70                  75                  80

Val Ala Val Leu Pro Val Ile Asp Ser Thr Asn Gln Tyr Leu Leu Asp
                85                  90                  95

Arg Ile Gly Glu Leu Lys Ser Gly Asp Ala Cys Ile Ala Glu Tyr Gln
            100                 105                 110

Gln Ala Gly Arg Gly Arg Gln Gly Arg Lys Trp Phe Ser Pro Phe Gly
        115                 120                 125

Ala Asn Leu Tyr Leu Ser Met Phe Trp Arg Leu Glu Gln Gly Pro Ala
```

```
                130                 135                 140
Ala Ala Ile Gly Leu Ser Leu Val Ile Gly Ile Val Met Ala Glu Val
145                 150                 155                 160

Leu Arg Lys Leu Gly Ala Asp Lys Val Arg Val Lys Trp Pro Asn Asp
                165                 170                 175

Leu Tyr Leu Gln Asp Arg Lys Leu Ala Gly Ile Leu Val Glu Leu Thr
                180                 185                 190

Gly Lys Thr Gly Asp Ala Ala Gln Ile Val Ile Gly Ala Gly Ile Asn
                195                 200                 205

Met Ala Met Arg Gln Val Glu Glu Ser Val Val Asn Gln Gly Trp Ile
                210                 215                 220

Thr Leu Gln Glu Ala Gly Ile Asn Leu Asp Arg Asn Thr Leu Ala Ala
225                 230                 235                 240

Met Leu Ile Arg Glu Leu Arg Ala Ala Leu Glu Leu Phe Glu Gln Glu
                245                 250                 255

Gly Leu Ala Pro Tyr Leu Ser Arg Trp Glu Lys Leu Asp Asn Phe Ile
                260                 265                 270

Asn Arg Pro Val Lys Leu Ile Ile Gly Asp Lys Glu Ile Phe Gly Ile
                275                 280                 285

Ser Arg Gly Ile Asp Lys Gln Gly Ala Leu Leu Leu Glu Gln Asp Gly
                290                 295                 300

Ile Ile Lys Pro Trp Met Gly Gly Glu Ile Ser Leu Arg Ser Ala Glu
305                 310                 315                 320

Lys

<210> SEQ ID NO 4
<211> LENGTH: 321
<212> TYPE: PRT
<213> ORGANISM: Escherichia coli

<400> SEQUENCE: 4

Met Lys Asp Asn Thr Val Pro Leu Lys Leu Ile Ala Leu Leu Ala Asn
1               5                   10                  15

Gly Glu Phe His Ser Gly Glu Gln Leu Gly Glu Thr Leu Gly Met Ser
                20                  25                  30

Arg Ala Ala Ile Asn Lys His Ile Gln Thr Leu Arg Asp Trp Gly Val
                35                  40                  45

Asp Val Phe Thr Val Pro Gly Lys Gly Tyr Ser Leu Pro Glu Pro Ile
                50                  55                  60

Gln Leu Leu Asn Ala Lys Gln Ile Leu Gly Gln Leu Asp Gly Gly Ser
65                  70                  75                  80

Val Ala Val Leu Pro Val Ile Asp Ser Thr Asn Gln Tyr Leu Leu Asp
                85                  90                  95

Arg Ile Gly Glu Leu Lys Ser Gly Asp Ala Ser Ile Ala Glu Tyr Gln
                100                 105                 110

Gln Ala Gly Arg Gly Arg Arg Gly Arg Lys Trp Phe Ser Pro Phe Gly
                115                 120                 125

Ala Asn Leu Tyr Leu Ser Met Phe Trp Arg Leu Glu Gln Gly Pro Ala
                130                 135                 140

Ala Ala Ile Gly Leu Ser Leu Val Ile Gly Ile Val Met Ala Glu Val
145                 150                 155                 160

Leu Arg Lys Leu Gly Ala Asp Lys Val Arg Val Lys Trp Pro Asn Asp
                165                 170                 175

Leu Tyr Leu Gln Asp Arg Lys Leu Ala Gly Ile Leu Val Glu Leu Thr
```

```
              180                 185                 190
Gly Lys Thr Gly Asp Ala Ala Gln Ile Val Ile Gly Ala Gly Ile Asn
            195                 200                 205

Met Ala Met Arg Arg Val Glu Glu Ser Val Val Asn Gln Gly Trp Ile
            210                 215                 220

Thr Leu Gln Glu Ala Gly Ile Asn Leu Asp Arg Asn Thr Leu Ala Ala
225                 230                 235                 240

Met Leu Ile Arg Glu Leu Arg Ala Ala Leu Glu Leu Phe Glu Gln Glu
                    245                 250                 255

Gly Leu Ala Pro Tyr Leu Ser Arg Trp Glu Lys Leu Asp Asn Phe Ile
                260                 265                 270

Asn Arg Pro Val Lys Leu Ile Ile Gly Asp Lys Glu Ile Phe Gly Ile
            275                 280                 285

Ser Arg Gly Ile Asp Lys Gln Gly Ala Leu Leu Glu Gln Asp Gly
        290                 295                 300

Ile Ile Lys Pro Trp Met Gly Gly Glu Ile Ser Leu Arg Ser Ala Glu
305                 310                 315                 320

Lys

<210> SEQ ID NO 5
<211> LENGTH: 321
<212> TYPE: PRT
<213> ORGANISM: Escherichia coli

<400> SEQUENCE: 5

Met Lys Asp Asn Thr Val Pro Leu Lys Leu Ile Ala Leu Leu Ala Asn
1               5                   10                  15

Gly Glu Phe His Ser Gly Glu Gln Leu Gly Glu Thr Leu Gly Met Ser
            20                  25                  30

Arg Ala Ala Ile Asn Lys His Ile Gln Thr Leu Arg Asp Trp Gly Val
        35                  40                  45

Asp Val Phe Thr Val Pro Gly Lys Gly Tyr Ser Leu Pro Glu Pro Ile
    50                  55                  60

Gln Leu Leu Asn Ala Lys Gln Ile Leu Gly Gln Leu Asp Gly Gly Ser
65                  70                  75                  80

Val Ala Val Leu Pro Val Ile Asp Ser Thr Asn Gln Tyr Leu Leu Asp
                85                  90                  95

Arg Ile Gly Glu Leu Lys Ser Gly Asp Ala Ser Ile Ala Glu Tyr Gln
            100                 105                 110

Gln Ala Gly Arg Gly Arg Arg Gly Arg Lys Trp Phe Ser Pro Phe Gly
        115                 120                 125

Ala Asn Leu Tyr Leu Ser Met Phe Trp Arg Leu Glu Gln Gly Pro Ala
    130                 135                 140

Ala Ala Ile Gly Leu Ser Leu Val Ile Gly Ile Val Met Ala Glu Val
145                 150                 155                 160

Leu Arg Lys Leu Gly Ala Asp Lys Val Arg Val Lys Trp Pro Asn Asp
                165                 170                 175

Leu Tyr Leu Gln Asp Arg Lys Leu Ala Gly Ile Leu Val Glu Leu Thr
            180                 185                 190

Gly Lys Thr Gly Asp Ala Ala Gln Ile Val Ile Gly Ala Gly Ile Asn
        195                 200                 205

Met Ala Met Arg Gln Val Glu Glu Ser Val Val Asn Gln Gly Trp Ile
    210                 215                 220

Thr Leu Gln Glu Ala Gly Ile Asn Leu Asp Arg Asn Thr Leu Ala Ala
```

```
                    225                 230                 235                 240

Met Leu Ile Arg Glu Leu Arg Ala Ala Leu Glu Leu Phe Glu Gln Glu
                245                 250                 255

Gly Leu Ala Pro Tyr Leu Ser Arg Trp Glu Lys Leu Asp Asn Phe Ile
            260                 265                 270

Asn Arg Pro Val Lys Leu Ile Ile Gly Asp Lys Glu Ile Phe Gly Ile
        275                 280                 285

Ser Arg Gly Ile Asp Lys Gln Gly Ala Leu Leu Glu Gln Asp Gly
    290                 295                 300

Ile Ile Lys Pro Trp Met Gly Glu Ile Ser Leu Arg Ser Ala Glu
305                 310                 315                 320

Lys

<210> SEQ ID NO 6
<211> LENGTH: 321
<212> TYPE: PRT
<213> ORGANISM: Escherichia coli

<400> SEQUENCE: 6

Met Lys Asp Asn Thr Val Pro Leu Lys Leu Ile Ala Leu Leu Ala Asn
1               5                  10                  15

Gly Glu Phe His Ser Gly Glu Gln Leu Gly Glu Thr Leu Gly Met Ser
                20                  25                  30

Arg Ala Ala Ile Asn Lys His Ile Gln Thr Leu Arg Asp Trp Gly Val
            35                  40                  45

Asp Val Phe Thr Val Pro Gly Lys Gly Tyr Ser Leu Pro Glu Pro Ile
        50                  55                  60

Gln Leu Leu Asn Ala Lys Gln Ile Leu Gly Gln Leu Asp Gly Gly Ser
65                  70                  75                  80

Val Ala Val Leu Pro Val Ile Asp Ser Thr Asn Gln Tyr Leu Leu Asp
                85                  90                  95

Arg Ile Gly Glu Leu Lys Ser Gly Asp Ala Ser Ile Ala Glu Tyr Gln
            100                 105                 110

Gln Ala Gly Arg Gly Arg Gln Gly Arg Lys Trp Phe Ser Pro Phe Gly
        115                 120                 125

Ala Asn Leu Tyr Leu Ser Met Phe Trp Arg Leu Glu Gln Gly Pro Ala
    130                 135                 140

Ala Ala Ile Gly Leu Ser Leu Val Ile Gly Ile Val Met Ala Glu Val
145                 150                 155                 160

Leu Arg Lys Leu Gly Ala Asp Lys Val Arg Val Lys Trp Pro Asn Asp
                165                 170                 175

Leu Tyr Leu Gln Asp Arg Lys Leu Ala Gly Ile Leu Val Glu Leu Thr
            180                 185                 190

Gly Lys Thr Gly Asp Ala Ala Gln Ile Val Ile Gly Ala Gly Ile Asn
        195                 200                 205

Met Ala Met Arg Gln Val Glu Glu Ser Val Val Asn Gln Gly Trp Ile
    210                 215                 220

Thr Leu Gln Glu Ala Gly Ile Asn Leu Asp Arg Asn Thr Leu Ala Ala
225                 230                 235                 240

Met Leu Ile Arg Glu Leu Arg Ala Ala Leu Glu Leu Phe Glu Gln Glu
                245                 250                 255

Gly Leu Ala Pro Tyr Leu Ser Arg Trp Glu Lys Leu Asp Asn Phe Ile
            260                 265                 270

Asn Arg Pro Val Lys Leu Ile Ile Gly Asp Lys Glu Ile Phe Gly Ile
```

```
                275                 280                 285
Ser Arg Gly Ile Asp Lys Gln Gly Ala Leu Leu Glu Gln Asp Gly
    290                 295                 300

Ile Ile Lys Pro Trp Met Gly Gly Glu Ile Ser Leu Arg Ser Ala Glu
305                 310                 315                 320

Lys
```

<210> SEQ ID NO 7
<211> LENGTH: 690
<212> TYPE: PRT
<213> ORGANISM: Saccharomyces cerevisiae

<400> SEQUENCE: 7

```
Met Asn Val Leu Val Tyr Asn Gly Pro Gly Thr Thr Pro Gly Ser Val
1               5                   10                  15

Lys His Ala Val Glu Ser Leu Arg Asp Phe Leu Glu Pro Tyr Tyr Ala
                20                  25                  30

Val Ser Thr Val Asn Val Lys Val Leu Gln Thr Glu Pro Trp Met Ser
            35                  40                  45

Lys Thr Ser Ala Val Val Phe Pro Gly Gly Ala Asp Leu Pro Tyr Val
50                  55                  60

Gln Ala Cys Gln Pro Ile Ile Ser Arg Leu Lys His Phe Val Ser Lys
65                  70                  75                  80

Gln Gly Gly Val Phe Ile Gly Phe Cys Ala Gly Gly Tyr Phe Gly Thr
                85                  90                  95

Ser Arg Val Glu Phe Ala Gln Gly Asp Pro Thr Met Glu Val Ser Gly
            100                 105                 110

Ser Arg Asp Leu Arg Phe Phe Pro Gly Thr Ser Arg Gly Pro Ala Tyr
        115                 120                 125

Asn Gly Phe Gln Tyr Asn Ser Glu Ala Gly Ala Arg Ala Val Lys Leu
    130                 135                 140

Asn Leu Pro Asp Gly Ser Gln Phe Ser Thr Tyr Phe Asn Gly Gly Ala
145                 150                 155                 160

Val Phe Val Asp Ala Asp Lys Phe Asp Asn Val Glu Ile Leu Ala Thr
                165                 170                 175

Tyr Ala Glu His Pro Asp Val Pro Ser Ser Asp Ser Gly Lys Gly Gln
            180                 185                 190

Ser Glu Asn Pro Ala Ala Val Leu Cys Thr Val Gly Arg Gly Lys
        195                 200                 205

Val Leu Leu Thr Gly Pro His Pro Glu Phe Asn Val Arg Phe Met Arg
    210                 215                 220

Lys Ser Thr Asp Lys His Phe Leu Glu Thr Val Val Glu Asn Leu Lys
225                 230                 235                 240

Ala Gln Glu Ile Met Arg Leu Lys Phe Met Arg Thr Val Leu Thr Lys
                245                 250                 255

Thr Gly Leu Asn Cys Asn Asn Asp Phe Asn Tyr Val Arg Ala Pro Asn
            260                 265                 270

Leu Thr Pro Leu Phe Met Ala Ser Ala Pro Asn Lys Arg Asn Tyr Leu
        275                 280                 285

Gln Glu Met Glu Asn Asn Leu Ala His His Gly Met His Ala Asn Asn
    290                 295                 300

Val Glu Leu Cys Ser Glu Leu Asn Ala Glu Thr Asp Ser Phe Gln Phe
305                 310                 315                 320

Tyr Arg Gly Tyr Arg Ala Ser Tyr Asp Ala Ala Ser Ser Ser Leu Leu
```

```
            325                 330                 335
His Lys Glu Pro Asp Glu Val Pro Lys Thr Val Ile Phe Pro Gly Val
        340                 345                 350

Asp Glu Asp Ile Pro Pro Phe Gln Tyr Thr Pro Asn Phe Asp Met Lys
        355                 360                 365

Glu Tyr Phe Lys Tyr Leu Asn Val Gln Asn Thr Ile Gly Ser Leu Leu
        370                 375                 380

Leu Tyr Gly Glu Val Val Thr Ser Thr Ser Thr Ile Leu Asn Asn Asn
385                 390                 395                 400

Lys Ser Leu Leu Ser Ser Ile Pro Glu Ser Thr Leu Leu His Val Gly
                405                 410                 415

Thr Ile Gln Val Ser Gly Arg Gly Arg Gly Gly Asn Thr Trp Ile Asn
                420                 425                 430

Pro Lys Gly Val Cys Ala Ser Thr Ala Val Val Thr Met Pro Leu Gln
                435                 440                 445

Ser Pro Val Thr Asn Arg Asn Ile Ser Val Val Phe Val Gln Tyr Leu
        450                 455                 460

Ser Met Leu Ala Tyr Cys Lys Ala Ile Leu Ser Tyr Ala Pro Gly Phe
465                 470                 475                 480

Ser Asp Ile Pro Val Arg Ile Lys Trp Pro Asn Asp Leu Tyr Ala Leu
                485                 490                 495

Ser Pro Thr Tyr Tyr Lys Arg Lys Asn Leu Lys Leu Val Asn Thr Gly
                500                 505                 510

Phe Glu His Thr Lys Leu Pro Leu Gly Asp Ile Glu Pro Ala Tyr Leu
                515                 520                 525

Lys Ile Ser Gly Leu Leu Val Asn Thr His Phe Ile Asn Asn Lys Tyr
530                 535                 540

Cys Leu Leu Leu Gly Cys Gly Ile Asn Leu Thr Ser Asp Gly Pro Thr
545                 550                 555                 560

Thr Ser Leu Gln Thr Trp Ile Asp Ile Leu Asn Glu Glu Arg Gln Gln
                565                 570                 575

Leu His Leu Asp Leu Leu Pro Ala Ile Lys Ala Glu Lys Leu Gln Ala
                580                 585                 590

Leu Tyr Met Asn Asn Leu Glu Val Ile Leu Lys Gln Phe Ile Asn Tyr
                595                 600                 605

Gly Ala Ala Glu Ile Leu Pro Ser Tyr Tyr Glu Leu Trp Leu His Ser
610                 615                 620

Asn Gln Ile Val Thr Leu Pro Asp His Gly Asn Thr Gln Ala Met Ile
625                 630                 635                 640

Thr Gly Ile Thr Glu Asp Tyr Gly Leu Leu Ile Ala Lys Glu Leu Val
                645                 650                 655

Ser Gly Ser Ser Thr Gln Phe Thr Gly Asn Val Tyr Asn Leu Gln Pro
                660                 665                 670

Asp Gly Asn Thr Phe Asp Ile Phe Lys Ser Leu Ile Ala Lys Lys Val
                675                 680                 685

Gln Ser
    690

<210> SEQ ID NO 8
<211> LENGTH: 690
<212> TYPE: PRT
<213> ORGANISM: Saccharomyces cerevisiae

<400> SEQUENCE: 8
```

```
Met Asn Val Leu Val Tyr Asn Gly Pro Gly Thr Thr Pro Gly Ser Val
1               5                   10                  15

Lys His Ala Val Glu Ser Leu Arg Asp Phe Leu Glu Pro Tyr Tyr Ala
            20                  25                  30

Val Ser Thr Val Asn Val Lys Val Leu Gln Thr Glu Pro Trp Met Ser
            35                  40                  45

Lys Thr Ser Ala Val Val Phe Pro Gly Gly Ala Asp Leu Pro Tyr Val
50                      55                  60

Gln Ala Cys Gln Pro Ile Ile Ser Arg Leu Lys His Phe Val Ser Lys
65                      70                  75                  80

Gln Gly Gly Val Phe Ile Gly Phe Cys Ala Gly Gly Tyr Phe Gly Thr
                85                  90                  95

Ser Arg Val Glu Phe Ala Gln Gly Asp Pro Thr Met Glu Val Ser Gly
            100                 105                 110

Ser Arg Asp Leu Arg Phe Phe Pro Gly Thr Ser Arg Gly Pro Ala Tyr
            115                 120                 125

Asn Gly Phe Gln Tyr Asn Ser Glu Ala Gly Ala Arg Ala Val Lys Leu
            130                 135                 140

Asn Leu Pro Asp Gly Ser Gln Phe Ser Thr Tyr Phe Asn Gly Gly Ala
145                 150                 155                 160

Val Phe Val Asp Ala Asp Lys Phe Asp Asn Val Glu Ile Leu Ala Thr
                165                 170                 175

Tyr Ala Glu His Pro Asp Val Pro Ser Ser Asp Ser Gly Lys Gly Gln
            180                 185                 190

Ser Glu Asn Pro Ala Ala Val Val Leu Cys Thr Val Gly Arg Gly Lys
            195                 200                 205

Val Leu Leu Thr Gly Pro His Pro Glu Phe Asn Val Arg Phe Met Arg
210                 215                 220

Lys Ser Thr Asp Lys His Phe Leu Glu Thr Val Val Glu Asn Leu Lys
225                 230                 235                 240

Ala Gln Glu Ile Met Arg Leu Lys Phe Met Arg Thr Val Leu Thr Lys
                245                 250                 255

Thr Gly Leu Asn Cys Asn Asn Asp Phe Asn Tyr Val Arg Ala Pro Asn
            260                 265                 270

Leu Thr Pro Leu Phe Met Ala Ser Ala Pro Asn Lys Lys Asn Tyr Leu
            275                 280                 285

Gln Glu Met Glu Asn Asn Leu Ala His His Gly Met His Ala Asn Asn
            290                 295                 300

Val Glu Leu Cys Ser Glu Leu Asn Ala Glu Thr Asp Ser Phe Gln Phe
305                 310                 315                 320

Tyr Arg Gly Tyr Arg Ala Ser Tyr Asp Ala Ala Ser Ser Leu Leu
                325                 330                 335

His Lys Glu Pro Asp Glu Val Pro Lys Thr Val Ile Phe Pro Gly Val
            340                 345                 350

Asp Glu Asp Ile Pro Pro Phe Gln Tyr Thr Pro Asn Phe Asp Met Lys
            355                 360                 365

Glu Tyr Phe Lys Tyr Leu Asn Val Gln Asn Thr Ile Gly Ser Leu Leu
            370                 375                 380

Leu Tyr Gly Glu Val Val Thr Ser Thr Ser Thr Ile Leu Asn Asn Asn
385                 390                 395                 400

Lys Ser Leu Leu Ser Ser Ile Pro Glu Ser Thr Leu Leu His Val Gly
                405                 410                 415

Thr Ile Gln Val Ser Gly Arg Gly Arg Gly Gly Asn Thr Trp Ile Asn
```

420             425             430
Pro Lys Gly Val Cys Ala Ser Thr Ala Val Val Thr Met Pro Leu Gln
            435                 440                 445

Ser Pro Val Thr Asn Arg Asn Ile Ser Val Val Phe Val Gln Tyr Leu
    450                 455                 460

Ser Met Leu Ala Tyr Cys Lys Ala Ile Leu Ser Tyr Ala Pro Gly Phe
465                 470                 475                 480

Ser Asp Ile Pro Val Arg Ile Lys Trp Pro Asn Asp Leu Tyr Ala Leu
                485                 490                 495

Ser Pro Thr Tyr Tyr Lys Lys Asn Leu Lys Leu Val Asn Thr Gly
            500                 505                 510

Phe Glu His Thr Lys Leu Pro Leu Gly Asp Ile Glu Pro Ala Tyr Leu
        515                 520                 525

Lys Ile Ser Gly Leu Leu Val Asn Thr His Phe Ile Asn Asn Lys Tyr
    530                 535                 540

Cys Leu Leu Gly Cys Gly Ile Asn Leu Thr Ser Asp Gly Pro Thr
545                 550                 555                 560

Thr Ser Leu Gln Thr Trp Ile Asp Ile Leu Asn Glu Glu Arg Gln Gln
                565                 570                 575

Leu His Leu Asp Leu Leu Pro Ala Ile Lys Ala Glu Lys Leu Gln Ala
            580                 585                 590

Leu Tyr Met Asn Asn Leu Glu Val Ile Leu Lys Gln Phe Ile Asn Tyr
        595                 600                 605

Gly Ala Ala Glu Ile Leu Pro Ser Tyr Tyr Glu Leu Trp Leu His Ser
    610                 615                 620

Asn Gln Ile Val Thr Leu Pro Asp His Gly Asn Thr Gln Ala Met Ile
625                 630                 635                 640

Thr Gly Ile Thr Glu Asp Tyr Gly Leu Leu Ile Ala Lys Glu Leu Val
                645                 650                 655

Ser Gly Ser Ser Thr Gln Phe Thr Gly Asn Val Tyr Asn Leu Gln Pro
            660                 665                 670

Asp Gly Asn Thr Phe Asp Ile Phe Lys Ser Leu Ile Ala Lys Lys Val
        675                 680                 685

Gln Ser
    690

<210> SEQ ID NO 9
<211> LENGTH: 690
<212> TYPE: PRT
<213> ORGANISM: Saccharomyces cerevisiae

<400> SEQUENCE: 9

Met Asn Val Leu Val Tyr Asn Gly Pro Gly Thr Thr Pro Gly Ser Val
1               5                   10                  15

Lys His Ala Val Glu Ser Leu Arg Asp Phe Leu Glu Pro Tyr Tyr Ala
            20                  25                  30

Val Ser Thr Val Asn Val Lys Val Leu Gln Thr Glu Pro Trp Met Ser
        35                  40                  45

Lys Thr Ser Ala Val Val Phe Pro Gly Gly Ala Asp Leu Pro Tyr Val
    50                  55                  60

Gln Ala Cys Gln Pro Ile Ile Ser Arg Leu Lys His Phe Val Ser Lys
65                  70                  75                  80

Gln Gly Gly Val Phe Ile Gly Phe Cys Ala Gly Gly Tyr Phe Gly Thr
                85                  90                  95

```
Ser Arg Val Glu Phe Ala Gln Gly Asp Pro Thr Met Glu Val Ser Gly
            100                 105                 110

Ser Arg Asp Leu Arg Phe Phe Pro Gly Thr Ser Arg Gly Pro Ala Tyr
        115                 120                 125

Asn Gly Phe Gln Tyr Asn Ser Glu Ala Gly Ala Arg Ala Val Lys Leu
    130                 135                 140

Asn Leu Pro Asp Gly Ser Gln Phe Ser Thr Tyr Phe Asn Gly Gly Ala
145                 150                 155                 160

Val Phe Val Asp Ala Asp Lys Phe Asp Asn Val Glu Ile Leu Ala Thr
                165                 170                 175

Tyr Ala Glu His Pro Asp Val Pro Ser Ser Asp Ser Gly Lys Gly Gln
            180                 185                 190

Ser Glu Asn Pro Ala Ala Val Val Leu Cys Thr Val Gly Arg Gly Lys
        195                 200                 205

Val Leu Leu Thr Gly Pro His Pro Glu Phe Asn Val Arg Phe Met Arg
    210                 215                 220

Lys Ser Thr Asp Lys His Phe Leu Glu Thr Val Val Glu Asn Leu Lys
225                 230                 235                 240

Ala Gln Glu Ile Met Arg Leu Lys Phe Met Arg Thr Val Leu Thr Lys
                245                 250                 255

Thr Gly Leu Asn Cys Asn Asn Asp Phe Asn Tyr Val Arg Ala Pro Ser
            260                 265                 270

Leu Thr Pro Leu Phe Met Ala Ser Ala Pro Asn Lys Lys Asn Tyr Leu
        275                 280                 285

Gln Glu Met Glu Asn Asn Leu Ala His His Gly Met His Ala Asn Asn
    290                 295                 300

Val Glu Leu Cys Ser Glu Leu Asn Ala Glu Thr Asp Ser Phe Gln Phe
305                 310                 315                 320

Tyr Arg Gly Tyr Arg Ala Ser Tyr Asp Ala Ala Ser Ser Ser Leu Leu
                325                 330                 335

His Lys Glu Pro Asp Glu Val Pro Lys Thr Val Ile Phe Pro Gly Val
            340                 345                 350

Asp Glu Asp Ile Pro Pro Phe Gln Tyr Thr Pro Asn Phe Asp Met Lys
        355                 360                 365

Glu Tyr Phe Lys Tyr Leu Asn Val Gln Asn Thr Ile Gly Ser Leu Leu
    370                 375                 380

Leu Tyr Gly Glu Val Val Thr Ser Thr Ser Thr Ile Leu Asn Asn Asn
385                 390                 395                 400

Lys Ala Leu Leu Ser Ser Ile Pro Glu Ser Thr Leu Leu His Val Gly
                405                 410                 415

Thr Ile Gln Val Ser Gly Arg Gly Arg Gly Gly Asn Thr Trp Ile Asn
            420                 425                 430

Pro Lys Gly Val Cys Ala Ser Thr Ala Val Val Thr Met Pro Leu Gln
        435                 440                 445

Ser Pro Val Thr Asn Arg Ala Ile Ser Val Val Phe Gln Tyr Leu
    450                 455                 460

Ser Met Leu Ala Tyr Cys Lys Ala Ile Leu Ser Tyr Ala Pro Gly Phe
465                 470                 475                 480

Ser Asp Ile Pro Val Arg Ile Lys Trp Pro Asn Asp Leu Tyr Ala Leu
                485                 490                 495

Ser Pro Thr Tyr Tyr Lys Lys Asn Leu Lys Leu Val Asn Thr Gly
            500                 505                 510

Phe Glu His Thr Lys Leu Pro Leu Gly Asp Ile Glu Pro Ala Tyr Leu
```

```
            515                 520                 525
Lys Ile Ser Gly Leu Leu Val Asn Thr His Phe Ile Asn Asn Lys Tyr
    530                 535                 540

Cys Leu Leu Gly Cys Gly Ile Ser Leu Thr Ser Asp Gly Pro Thr
545                 550                 555                 560

Thr Ser Leu Gln Thr Trp Ile Asp Ile Leu Asn Glu Glu Arg Gln Gln
                565                 570                 575

Leu His Leu Asp Leu Leu Pro Ala Ile Lys Ala Glu Lys Leu Gln Ala
            580                 585                 590

Leu Tyr Met Asn Asn Leu Glu Val Ile Leu Lys Gln Phe Ile Asn Tyr
                595                 600                 605

Gly Ala Ala Glu Ile Leu Pro Ser Tyr Tyr Glu Leu Trp Leu His Ser
    610                 615                 620

Asn Gln Ile Val Thr Leu Pro Asp His Gly Asn Thr Gln Ala Met Ile
625                 630                 635                 640

Thr Gly Ile Thr Glu Asp Tyr Gly Leu Leu Ile Ala Lys Glu Leu Val
                645                 650                 655

Ser Gly Ser Ser Thr Gln Phe Thr Gly Asn Val Tyr Asn Leu Gln Pro
            660                 665                 670

Asp Gly Asn Thr Phe Asp Ile Phe Lys Ser Leu Ile Ala Lys Lys Val
                675                 680                 685

Gln Ser
    690

<210> SEQ ID NO 10
<211> LENGTH: 690
<212> TYPE: PRT
<213> ORGANISM: Saccharomyces cerevisiae

<400> SEQUENCE: 10

Met Asn Val Leu Val Tyr Asn Gly Pro Gly Thr Thr Pro Gly Ser Val
1               5                   10                  15

Lys His Ala Val Glu Ser Leu Arg Asp Phe Leu Glu Pro Tyr Tyr Ala
                20                  25                  30

Val Ser Thr Val Asn Val Lys Val Leu Gln Thr Glu Pro Trp Met Ser
            35                  40                  45

Lys Thr Ser Ala Val Val Phe Pro Gly Gly Ala Asp Leu Pro Tyr Val
    50                  55                  60

Gln Ala Cys Gln Pro Ile Ile Ser Arg Leu Lys His Phe Val Ser Lys
65                  70                  75                  80

Gln Gly Gly Val Phe Ile Gly Phe Cys Ala Gly Gly Tyr Phe Gly Thr
                85                  90                  95

Ser Arg Val Glu Phe Ala Gln Gly Asp Pro Thr Met Glu Val Ser Gly
                100                 105                 110

Ser Arg Asp Leu Arg Phe Phe Pro Gly Thr Ser Arg Gly Pro Ala Tyr
            115                 120                 125

Asn Gly Phe Gln Tyr Asn Ser Glu Ala Gly Ala Arg Ala Val Lys Leu
    130                 135                 140

Asn Leu Pro Asp Gly Ser Gln Phe Ser Thr Tyr Phe Asn Gly Gly Ala
145                 150                 155                 160

Val Phe Val Asp Ala Asp Lys Phe Asp Asn Val Glu Ile Leu Ala Thr
                165                 170                 175

Tyr Ala Glu His Pro Asp Val Pro Ser Ser Asp Ser Gly Lys Gly Gln
            180                 185                 190
```

```
Ser Glu Asn Pro Ala Ala Val Val Leu Cys Thr Val Gly Arg Gly Lys
            195                 200                 205
Val Leu Leu Thr Gly Pro His Pro Glu Phe Asn Val Arg Phe Met Arg
    210                 215                 220
Lys Ser Thr Asp Lys His Phe Leu Glu Thr Val Val Glu Asn Leu Lys
225                 230                 235                 240
Ala Gln Glu Ile Met Arg Leu Lys Phe Met Arg Thr Val Leu Thr Lys
                245                 250                 255
Thr Gly Leu Asn Cys Asn Asn Asp Phe Asn Tyr Val Arg Ala Pro Ser
            260                 265                 270
Leu Thr Pro Leu Phe Met Ala Ser Ala Pro Asn Lys Arg Asn Tyr Leu
        275                 280                 285
Gln Glu Met Glu Asn Asn Leu Ala His His Gly Met His Ala Asn Asn
    290                 295                 300
Val Glu Leu Cys Ser Glu Leu Asn Ala Glu Thr Asp Ser Phe Gln Phe
305                 310                 315                 320
Tyr Arg Gly Tyr Arg Ala Ser Tyr Asp Ala Ala Ser Ser Ser Leu Leu
                325                 330                 335
His Lys Glu Pro Asp Glu Val Pro Lys Thr Val Ile Phe Pro Gly Val
            340                 345                 350
Asp Glu Asp Ile Pro Pro Phe Gln Tyr Thr Pro Asn Phe Asp Met Lys
        355                 360                 365
Glu Tyr Phe Lys Tyr Leu Asn Val Gln Asn Thr Ile Gly Ser Leu Leu
    370                 375                 380
Leu Tyr Gly Glu Val Val Thr Ser Thr Ser Thr Ile Leu Asn Asn Asn
385                 390                 395                 400
Lys Ala Leu Leu Ser Ser Ile Pro Glu Ser Thr Leu Leu His Val Gly
                405                 410                 415
Thr Ile Gln Val Ser Arg Gly Arg Gly Gly Asn Thr Trp Ile Asn
            420                 425                 430
Pro Lys Gly Val Cys Ala Ser Thr Ala Val Val Thr Met Pro Leu Gln
        435                 440                 445
Ser Pro Val Thr Asn Arg Ala Ile Ser Val Val Phe Val Gln Tyr Leu
    450                 455                 460
Ser Met Leu Ala Tyr Cys Lys Ala Ile Leu Ser Tyr Ala Pro Gly Phe
465                 470                 475                 480
Ser Asp Ile Pro Val Arg Ile Lys Trp Pro Asn Asp Leu Tyr Ala Leu
                485                 490                 495
Ser Pro Thr Tyr Tyr Lys Arg Lys Asn Leu Lys Leu Val Asn Thr Gly
            500                 505                 510
Phe Glu His Thr Lys Leu Pro Leu Gly Asp Ile Glu Pro Ala Tyr Leu
        515                 520                 525
Lys Ile Ser Gly Leu Leu Val Asn Thr His Phe Ile Asn Asn Lys Tyr
    530                 535                 540
Cys Leu Leu Leu Gly Cys Gly Ile Ser Leu Thr Ser Asp Gly Pro Thr
545                 550                 555                 560
Thr Ser Leu Gln Thr Trp Ile Asp Ile Leu Asn Glu Glu Arg Gln Gln
                565                 570                 575
Leu His Leu Asp Leu Leu Pro Ala Ile Lys Ala Glu Lys Leu Gln Ala
            580                 585                 590
Leu Tyr Met Asn Asn Leu Glu Val Ile Leu Lys Gln Phe Ile Asn Tyr
        595                 600                 605
Gly Ala Ala Glu Ile Leu Pro Ser Tyr Tyr Glu Leu Trp Leu His Ser
```

610                 615                 620
Asn Gln Ile Val Thr Leu Pro Asp His Gly Asn Thr Gln Ala Met Ile
625                 630                 635                 640

Thr Gly Ile Thr Glu Asp Tyr Gly Leu Leu Ile Ala Lys Glu Leu Val
                645                 650                 655

Ser Gly Ser Ser Thr Gln Phe Thr Gly Asn Val Tyr Asn Leu Gln Pro
                660                 665                 670

Asp Gly Asn Thr Phe Asp Ile Phe Lys Ser Leu Ile Ala Lys Lys Val
                675                 680                 685

Gln Ser
    690

<210> SEQ ID NO 11
<211> LENGTH: 311
<212> TYPE: PRT
<213> ORGANISM: Streptococcus pneumoniae

<400> SEQUENCE: 11

Met Lys Ser Tyr Gln Ala Val Tyr Gln Ile Leu Ser Lys Glu Thr Asp
1               5                   10                  15

Tyr Ile Ser Gly Glu Lys Ile Ala Glu Lys Leu Ser Leu Ser Arg Thr
                20                  25                  30

Ser Ile Trp Lys Ala Ile Lys Arg Leu Glu Gln Glu Gly Ile Glu Ile
            35                  40                  45

Asp Ser Ile Lys Asn Arg Gly Tyr Lys Leu Met Asn Gly Asp Leu Ile
50                  55                  60

Leu Pro Glu Ile Leu Glu Asn Leu Pro Ile Lys Val Ser Phe Lys
65                  70                  75                  80

Pro Glu Thr Lys Ser Thr Gln Leu Asp Ala Lys Glu Ala Ile Asp Leu
                85                  90                  95

Gly His Glu Ala Asn Thr Leu Tyr Leu Ala Ser Tyr Gln Thr Ala Gly
            100                 105                 110

Arg Gly Arg Phe Gln Arg Ser Phe Tyr Ser Pro Gln Gly Gly Ile Tyr
        115                 120                 125

Met Thr Leu His Leu Lys Pro Asn Leu Pro Tyr Asp Lys Leu Pro Ser
130                 135                 140

Tyr Thr Leu Leu Val Ala Gly Ala Val Tyr Lys Ala Ile Lys Asn Leu
145                 150                 155                 160

Thr Leu Ile Asp Val Asp Ile Lys Trp Val Asn Asp Ile Tyr Leu Asn
                165                 170                 175

Asn His Lys Ile Gly Gly Ile Leu Thr Glu Ala Met Thr Ser Val Glu
            180                 185                 190

Thr Gly Leu Val Thr Asp Ile Ile Gly Val Gly Ile Asn Phe Thr
        195                 200                 205

Ile Lys Asp Phe Pro Gln Glu Leu Lys Glu Lys Ala Ala Ser Leu Phe
210                 215                 220

Lys Ala Thr Ala Pro Ile Thr Arg Asn Glu Leu Ile Ile Glu Ile Trp
225                 230                 235                 240

Arg Ala Phe Phe Glu Thr Pro Ala Glu Glu Leu Leu Tyr Leu Tyr Lys
                245                 250                 255

Lys Gln Ser Phe Ile Leu Gly Lys Glu Val Thr Phe Thr Leu Glu Gln
            260                 265                 270

Lys Asp Tyr Lys Gly Leu Ala Lys Asp Ile Ser Glu Asn Gly Lys Leu
        275                 280                 285

```
Leu Val Gln Cys Asp Asn Gly Lys Glu Ile Trp Leu Asn Ser Gly Glu
    290                 295                 300

Ile Ser Leu Asn Ser Trp Lys
305                 310

<210> SEQ ID NO 12
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa is Arg or Leu
<220> FEATURE:
<221> NAME/KEY: MISC_FEATURE
<222> LOCATION: (4)..(4)
<223> OTHER INFORMATION: Xaa is Ser or Thr
<220> FEATURE:
<221> NAME/KEY: MISC_FEATURE
<222> LOCATION: (6)..(6)
<223> OTHER INFORMATION: Xaa is Tyr or Trp

<400> SEQUENCE: 12

Asp Xaa Ala Xaa Pro Xaa
1               5

<210> SEQ ID NO 13
<211> LENGTH: 15
<212> TYPE: PRT
<213> ORGANISM: Artificial Sequence
<220> FEATURE:
<223> OTHER INFORMATION: Synthetic peptide

<400> SEQUENCE: 13

Gly Gly Gly Gly Ser Gly Gly Gly Gly Ser Gly Gly Gly Gly Ser
1               5                   10                  15
```

CELL SURFACE DISPLAY, SCREENING AND PRODUCTION OF PROTEINS OF INTEREST

RELATED APPLICATIONS

This application is a divisional of U.S. patent application Ser. No. 12/056,264, filed Mar. 26, 2008, now U.S. Pat. No. 8,709,980, issued on Apr. 29, 2014, which claims the benefit under 35 U.S.C. §119(e) from U.S. provisional application Ser. No. 60/920,378 entitled "In vivo protein display as tools for surface display" filed Mar. 26, 2007, Ser. No. 60/920,375 entitled "Evaluating predetermined protein functions", filed Mar. 26, 2007, Ser. No. 60/959,719 entitled "Cell surface display of proteins", filed Jul. 16, 2007, and Ser. No. 61/004,841 entitled "Cell surface display, screening and production of proteins of interest" filed Dec. 1, 2007, the entire contents of which are herein incorporated by reference.

REFERENCE TO SEQUENCE LISTING

This specification includes a sequence listing, submitted herewith, which includes the file entitled "128255-011511DIV_ST25.txt" having the following size: 44,554 bytes which was created Mar. 26, 2014, the content of which is incorporated by reference herein.

FIELD OF THE INVENTION

The invention relates to the field of protein screening and libraries and components for protein screening. The invention also relates to the display and production of proteins of interest.

BACKGROUND OF THE INVENTION

Recombinant and synthetic nucleic acids have many applications in research, industry, agriculture, and medicine. Recombinant and synthetic nucleic acids can be used to express and obtain large amounts of polypeptides, including enzymes, antibodies, growth factors, receptors, and other polypeptides that may be used for a variety of medical, industrial, or agricultural purposes. Methods for screening of polypeptides with a predetermined function or property have been described, including phage display. However, current screening methods are limited by the size of the libraries, the lengths and complexities of polypeptides and available functional assays.

SUMMARY OF THE INVENTION

Aspects of the invention relate to compositions and methods for displaying an engineered protein on a host cell surface. In some embodiments, an engineered protein is expressed in a host cell under conditions that result in the protein being modified in such a way that the modified protein binds to a surface-immobilized binding partner if it is secreted from the host cell.

Accordingly, aspects of the invention are useful to express engineered proteins from host cell nucleic acids so that engineered proteins are secreted and retained on the surface of the host cells. Therefore, embodiments of the invention are useful to express and display many different variant proteins and polypeptides on host cell surfaces and to generate protein display libraries. These protein display libraries can be used to screen for one or more structural and/or functional properties of the protein. Once a host cell is identified as having a surface-displayed protein with a desired characteristic or function, the nucleic acid that encodes that protein can be isolated and characterized.

Aspects of the invention include methods of expressing and displaying engineered proteins on host cells. Aspects of the invention include nucleic acid constructs, expressed proteins, host cells, and/or isolated proteins.

In some embodiments, the invention provides a method for displaying an engineered protein on a host cell, the method comprising incubating a host cell comprising a first nucleic acid under conditions sufficient for expressing an engineered protein encoded by the first nucleic acid, wherein the host cell displays a first binding partner on its surface, wherein the engineered protein comprises a modification motif and a second binding partner is coupled to the modification motif when the engineered protein is expressed and, wherein the expressed engineered protein is secreted from the host cell and displayed on the cell surface via binding of the second binding partner to the first binding partner. In some embodiments, the method further comprises displaying a plurality of different engineered proteins, wherein each different engineered protein is encoded on a different first nucleic acid in a different host cell. In some embodiments, the different engineered proteins are sequence variants of each other. In some embodiments, the engineered protein comprises a secretion peptide. In some embodiments, the host cell is a yeast cell. In some embodiments, the modification motif is a biotin acceptor peptide. In some embodiments, the first binding partner is displayed via interaction with a further second binding partner attached to the cell surface. In some embodiments, the first binding partner is an avidin-like protein. In some embodiments, the second binding partner is biotin. In some embodiments, coupling of the second binding partner to the modification motif is catalyzed by a coupling enzyme. In some embodiments, the coupling enzyme is encoded on a second nucleic acid, wherein the second nucleic acid is a recombinant nucleic acid integrated into a vector or the genome of the host cell. In some embodiments, the coupling enzyme is a biotin ligase. In some embodiments, the method further comprises expressing a chaperone protein in the host cell.

In some embodiments, the invention provides a method for displaying an engineered protein on a cell surface, the method comprising incubating a host cell comprising a first nucleic acid under conditions sufficient for expressing an engineered protein encoded by the first nucleic acid, wherein the host cell comprises a first binding partner on its surface, and wherein the first binding partner is attached to the cell surface by binding to a cell wall protein comprising a second binding partner that specifically binds to the first binding partner, contacting the host cell with a target molecule that also comprises the second binding partner under conditions sufficient to immobilize the target molecule on the surface of the host cell via binding of the second binding partner to the first binding partner, incubating the cells under conditions resulting in secretion of the engineered protein, wherein the engineered protein binds to the target molecule, thereby displaying the engineered protein on the host cell surface. In some embodiments, the engineered protein is an antibody, a single chain antibody, a scaffold protein, or a fragment thereof.

In some embodiments, the invention provides a protein screening method comprising expressing an engineered protein comprising a modification motif in a host cell having a cell surface comprising a first binding partner, wherein a second binding partner is coupled to the expressed engineered protein, and wherein the expressed engineered protein is secreted and displayed on the cell surface via binding of the second binding partner to the first binding partner; and, evaluating a property of the engineered protein displayed on the cell surface. In some embodiments, the evaluating step comprises assaying a level of activity, determining whether the engineered protein has a predetermined function, comparing the property of the engineered protein to the property of a reference protein, or determining the amount of the engineered protein displayed on the cell surface. In some embodiments, the engineered protein is an antibody, and the function of the antibody being evaluated is the binding affinity of the antibody to the target molecule, wherein the target molecule comprises an antigen and/or epitope. In some embodiments, the host cells are selected on the basis of a first predetermined property of the displayed engineered protein. In some embodiments, the method further comprises selecting the host cells on the basis of a second predetermined property of the displayed engineered protein. In some embodiments, the method further comprises releasing the engineered protein from selected host cells displaying at least the predetermined level of the engineered protein. In some embodiments, assaying a level of activity comprises assaying if the engineered protein can process a substrate. In some embodiments, the substrate is coupled to the surface. In some embodiments, the substrate is a polypeptide, nucleic acid, lipid, polysaccharide, synthetic polymer or synthetic compound. In some embodiments, processing a substrate comprises binding to the substrate, dissociating the substrate, nicking the substrate, cutting the substrate, activating the substrate, deactivating the substrate, charging the substrate, decharging the substrate, changing substrate conformation, copying the substrate, replicating the substrate, conjugating molecules to the substrate, conjugating peptides to the substrate or modifying the substrate.

In some embodiments, the invention provides a method for evaluating if an engineered protein can process a substrate, the method comprising inducing expression of an engineered protein in a host cell, and measuring the level of a detectable signal generated by the engineered protein processing a substrate, wherein, a) the engineered protein is secreted, and b) the substrate is coupled to the host cell surface. In some embodiments, the substrate is a polypeptide, nucleic acid, lipid, polysaccharide, synthetic polymer or synthetic compound. In some embodiments, processing a substrate comprises binding to the substrate, dissociating the substrate, nicking the substrate, cutting the substrate, activating the substrate, deactivating the substrate, charging the substrate, decharging the substrate, changing substrate conformation, copying the substrate, replicating the substrate, conjugating molecules to the substrate, conjugating peptides to the substrate or modifying the substrate.

In some embodiments, the invention provides a host cell that comprises a first nucleic acid that encodes an engineered protein, wherein the host cell is capable of having a first binding partner coupled to its cell surface, wherein the engineered protein comprises a modification motif, and wherein expression of the engineered protein results in coupling of a second binding partner to the modification motif and secretion of the engineered protein so that it can be displayed on the cell surface via interaction binding of the second binding partner to the first binding partner. In some embodiments, the host cell displays at least $10^2$ engineered proteins. In some embodiments, the host cell displays at least $10^3$ engineered proteins. In some embodiments, the host cell displays at least $10^4$ engineered proteins. In some embodiments, the host cell displays at least $10^5$ engineered proteins, at least $10^6$ engineered proteins or more. In some embodiments, the invention provides a library of any of the host cells described herein. In some embodiments, the library has at least $10^8$ different members. In some embodiments, the library has at least 2, at least 5, at least 10, at least 50, at least 100, at least 1000, at least 10,000, at least 100,000, at least 1,000,000, at least $10^7$, at least $10^8$, at least $10^9$, at least $10^{10}$ or at least $10^{11}$ members.

In some embodiments, the invention provides a library of nucleic acids, the library comprising a plurality of nucleic acids, wherein each nucleic acid encodes a different variant of an engineered protein, and wherein each variant comprises an identical modification motif capable of coupling a binding partner. In some embodiments, the modification motif is a biotinylation motif. In some embodiments, the library has at least $10^8$ different members. In some embodiments, the library has at least 2, at least 5, at least 10, at least 50, at least 100, at least 1000, at least 10,000, at least 100,000, at least 1,000,000, at least $10^7$, at least $10^8$, at least $10^9$, at least $10^{10}$ or at least $10^{11}$ members.

In some embodiments, the invention provides methods of isolating an engineered protein with a predetermined function or level of activity.

In some embodiments, the invention provides a method for displaying an engineered protein on a host cell, the method comprising incubating a host cell comprising a first nucleic acid under conditions sufficient for expressing an engineered protein encoded by the first nucleic acid, wherein the host cell displays a first binding partner, wherein the engineered protein comprises a modification motif and a second binding partner is coupled to the modification motif when the engineered protein is expressed, and, wherein the expressed engineered protein is secreted from the host cell and displayed on the cell surface via binding of the second binding partner to the first binding partner. In some embodiments, the first binding partner is an avidin-like protein. In some embodiments, the second binding partner is biotin. In some embodiments the modification motif is a biotinylation peptide. In some embodiments, coupling of the second binding partner is done by a coupling enzyme. In some embodiments, the coupling enzyme is a biotin ligase. In some embodiments, the method further comprises expressing a chaperone protein.

In some embodiments, the invention provides a method for displaying an engineered protein on a cell surface, the method comprising introducing a vector comprising a gene encoding an engineered protein in a host cell, wherein the host cell displays a first binding partner on the cell surface, coupling a target molecule attached to a second binding partner to the first binding partner on the cell surface, thereby immobilizing the target molecule on the cell surface, incubating the cells under conditions resulting in secretion of the engineered protein, wherein the engineered protein binds to the target molecule, thereby displaying the engineered protein on the host cell surface. In some embodiments, the first binding partner is attached to the cell surface through a cell wall protein. In some embodiments, the engineered protein is an antibody and the target molecule is an antigen. In some embodiments, the engineered protein is a scaffold protein.

In some embodiments, the invention provides a method for displaying an engineered protein on a cell surface, the method comprising introducing a vector comprising a gene encoding an engineered protein in a host cell, wherein the host cell displays a third binding partner on the cell surface, adding a second binding partner to the host cell displaying the third binding partner, wherein the second binding partner binds to the third binding partner resulting in the display of the second binding partner on the cell surface, adding a target molecule attached to a first binding partner to the second binding partner, wherein the second binding partner binds to the first binding partner resulting in the display of the target molecule on the host cell surface, incubating the cells under conditions resulting in secretion of the engineered protein, wherein the engineered protein binds to the target molecule, thereby displaying the engineered protein on the host cell surface.

In some embodiments, the invention provides a protein screening method, the method comprising expressing an engineered protein comprising a modification motif in a host cell having a cell surface comprising a first binding partner, wherein a second binding partner is coupled to the expressed engineered protein, and wherein the expressed engineered protein is secreted and displayed on the cell surface via binding of the second binding partner to the first binding partner; and, evaluating a function of the engineered protein displayed on the cell surface. In some embodiments, the evaluating step comprises assaying a level of activity, determining whether the engineered protein has a predetermined function, or comparing the engineered protein to a reference protein. In some embodiments, assaying a level of activity comprises assaying if the engineered protein can process a substrate. In some embodiments, the substrate is a polypeptide, nucleic acid, lipid, polysaccharide, synthetic polymer or synthetic compound. In some embodiments, process a substrate comprises binding to the substrate, dissociating the substrate, nicking the substrate, cutting the substrate, activating the substrate, deactivating the substrate, charging the substrate, decharging the substrate, changing substrate conformation, copying the substrate, replicating the substrate, conjugating molecules to the substrate, conjugating peptides to the substrate or modifying the substrate.

In some embodiments, the invention provides a method for evaluating if an engineered protein can process a substrate, the method comprising inducing expression of an engineered protein in a host cell, and measuring the level of a detectable signal generated by the engineered protein processing a substrate, wherein a) the engineered protein is secreted, and b) the substrate is coupled to the host cell surface. In some embodiments, the substrate is a polypeptide, nucleic acid, lipid, polysaccharide, synthetic polymer or synthetic compound. In some embodiments, processing a substrate comprises binding to the substrate, dissociating the substrate, nicking the substrate, cutting the substrate, activating the substrate, deactivating the substrate, charging the substrate, decharging the substrate, changing substrate conformation, copying the substrate, replicating the substrate, conjugating molecules to the substrate, conjugating peptides to the substrate or modifying the substrate.

In some embodiments, the invention provides a host cell that comprises a first nucleic acid that encodes an engineered protein, wherein the host cell is capable of having a first binding partner coupled to its cell surface, wherein the engineered protein comprises a modification motif, and wherein expression of the engineered protein results in coupling of a second binding partner to the modification motif and secretion of the engineered protein so that it can be displayed on the cell surface via interaction binding of the second binding partner to the first binding partner. In some embodiments, the host cell displays at least $10^4$ engineered proteins. In some embodiments, the invention provides library of host cells. In some embodiments, the library has at least 2, at least 5, at least 10, at least 50, at least 100, at least 1000, at least 10,000, at least 100,000, at least 1,000,000, at least $10^7$, at least $10^8$, at least $10^9$, at least $10^{10}$ or at least $10^{11}$ members.

In some embodiments, the invention provides a library of nucleic acids, the library comprising a plurality of nucleic acids, wherein each nucleic acid encodes a different variant of an engineered protein, and wherein each variant comprises an identical modification motif. In some embodiments, the library has at least 2, at least 5, at least 10, at least 50, at least 100, at least 1000, at least 10,000, at least 100,000, at least 1,000,000, at least $10^7$, at least $10^8$, at least $10^9$, at least $10^{10}$ or at least $10^{11}$ members.

In some embodiments, the invention provides a method for displaying an engineered protein on a cell surface, the method comprising introducing a vector comprising a gene encoding an engineered protein in a host cell, wherein the host cell displays a first binding partner on the cell surface, wherein the engineered protein comprises a modification motif expressing the engineered proteins under conditions sufficient for coupling a second binding partner to the modification motif, secreting the engineered protein to the host cell surface; and, binding the second binding partner to the first binding partner on the cell surface, thereby displaying the engineered protein on the host cell surface.

In some embodiments, the invention provides a method for displaying an engineered protein on a cell surface, the method comprising generating a host cell displaying a first binding partner at its cell surface, introducing a nucleic acid encoding an engineered protein comprising a sequence encoding for a second binding partner or a modification motif allowing for in vivo coupling of a second binding partner, and, incubating the host cell under conditions sufficient for secreting engineered protein, wherein the first binding partner binds the second binding partner, thereby displaying the engineered protein on the host cell surface.

In some embodiments, the invention provides a method for displaying an engineered protein on a cell surface, the method comprising generating a host cell displaying a first binding partner on the cell surface, introducing a vector comprising a gene encoding an engineered protein comprising a second binding partner, incubating the host cell under conditions sufficient for secreting the engineered protein, and binding the second binding partner to the first binding partner on the cell surface, thereby displaying the engineered protein on the host cell surface.

In some embodiments, the invention provides a method for displaying an engineered protein on a cell surface, the method comprising introducing a vector comprising a gene encoding an engineered protein in a host cell, wherein the host cell displays a first binding partner on the cell surface, coupling the target molecule to the first binding partner on the cell surface, thereby immobilizing the target molecule on the cell surface, inducing secretion of the engineered protein, and binding the engineered protein to the target molecule, thereby displaying the engineered protein on the host cell surface, wherein the first binding partner is connected to the cell surface through binding to a second binding partner that is attached to the cell surface.

In some embodiments, the invention provides a method for generating a library of engineered proteins displayed on a cell surface, the method comprising introducing a plurality of vectors into a population of host cells, wherein the host cell displays a first binding partner on the cell surface, wherein each vector comprises a gene encoding a unique engineered protein, wherein each engineered protein comprises a unique polypeptide linked to an immobilization peptide, wherein the immobilization peptide comprises a modification motif, expressing the engineered proteins under conditions sufficient for: a) coupling a second binding partner to the modification motif; b) secreting the engineered proteins to the host cell surfaces, and, binding the second binding partner to the first binding partner on the cell surface, thereby generation of a library of engineered proteins displayed on a cell surface.

In some embodiments, the invention provides a method for generating a library of engineered proteins displayed on a cell surface, the method comprising introducing a plurality of vectors into a population of host cells, wherein the host cell displays a first binding partner on the cell surface, wherein each vector comprises a gene encoding a unique engineered protein linked to a second binding partner, expressing the engineered proteins under conditions sufficient for secreting the engineered proteins, and binding the second binding partner to the first binding partner on the cell surface, thereby generation of a library of engineered proteins displayed on a cell surface.

In some embodiments, the invention provides a method for generating a library of engineered proteins on a cell surface, the method comprising introducing a plurality of vectors into a population of host cells, wherein the host cell displays a first binding partner on the cell surface, wherein each vector comprises a gene encoding a unique engineered protein, wherein the engineered protein has affinity to a target molecule, coupling the target molecule to the first binding partner on the cell surface, thereby immobilizing the target molecule on the cell surface, inducing secretion of the engineered proteins, and, binding the engineered protein to the target molecule, thereby generation of a library of engineered proteins displayed on a cell surface.

In some embodiments, the invention provides a method for evaluating if an engineered protein has a predetermined function, the method comprising inducing expression of an engineered protein in a host cell, wherein the host cell displays a first binding partner on the cell surface, and wherein a) the engineered protein comprises a modification motif; b) a second binding partner is coupled to the modification motif; c) the engineered protein is secreted; and, d) the second binding partner is bound to the first binding partner on the cell surface, thereby displaying the engineered protein on the host cell surface, and evaluating if the engineered protein has the predetermined function.

In some embodiments, the invention provides a method for assaying the activity of an engineered protein, the method comprising inducing expression of an engineered protein in a host cell, wherein the host cell displays a first binding partner on the cell surface, and wherein a) the engineered protein comprises a modification motif; b) a second binding partner is coupled to the modification motif; c) the engineered protein is secreted; and, d) the second binding partner is bound to the first binding partner on the cell surface, thereby displaying the engineered protein on the host cell surface, and assaying the activity of the engineered protein.

In some embodiments, the invention provides a method for evaluating if a protein complex of engineered proteins has a predetermined function, the method comprising inducing expression of two or more engineered proteins in a host cell, wherein the host cell displays a first binding partner on the cell surface, and wherein a) the engineered protein comprises a modification motif; b) a second binding partner is coupled to the modification motif; c) the engineered protein is secreted; and d) the second binding partner is bound to the first binding partner on the cell surface, thereby displaying the engineered protein on the host cell surface, wherein the two or more engineered proteins interact to form a protein complex of engineered proteins, and evaluating if the protein complex of engineered proteins has the predetermined function.

In some embodiments, the invention provides a method for assaying the activity of a protein complex of engineered proteins, the method comprising inducing expression of two or more engineered proteins in a host cell, wherein the host cell displays a first binding partner on the cell surface, and wherein a) the engineered protein comprises a modification motif; b) a second binding partner is coupled to the modification motif; c) the engineered protein is secreted; and, d) the second binding partner is bound to the first binding partner on the cell surface, thereby displaying the engineered protein on the host cell surface, wherein the two or more engineered proteins interact to form a protein complex of engineered proteins, and assaying the activity of the protein complex of engineered proteins.

In some embodiments, the invention provides a method for evaluating if an engineered protein can process a substrate, the method comprising inducing expression of an engineered protein in a host cell, wherein the host cell displays a first binding partner on the cell surface, and wherein a) the engineered protein comprises a modification motif; b) a second binding partner is coupled to the modification motif; c) the engineered protein is secreted; and, d) the second binding partner is bound to the first binding partner on the cell surface, thereby displaying the engineered protein on the host cell surface; and contacting the engineered protein with a substrate, wherein if the engineered protein interacts with the substrate, the engineered protein can process the substrate.

In some embodiments, the invention provides a method for assaying the activity of an engineered protein, the method comprising inducing expression of an engineered protein in a host cell, wherein the host cell displays a first binding partner on the cell surface, and wherein a) the engineered protein comprises a modification motif; b) a second binding partner is coupled to the modification motif; c) the engineered protein is secreted; and, d) the second binding partner is bound to the first binding partner on the cell surface, thereby displaying the engineered protein on the host cell surface; contacting the engineered protein with a substrate, and assaying the activity of the engineered protein.

In some embodiments, the invention provides a method for evaluating if a protein complex of engineered proteins can process a substrate, the method comprising inducing expression of two or more engineered proteins in a host cell, wherein the host cell displays a first binding partner on the cell surface, and wherein a) the engineered protein comprises a modification motif; b) a second binding partner is coupled to the modification motif; c) the engineered protein is secreted; and, d) the second binding partner is bound to the first binding partner on the cell surface, thereby displaying the engineered protein on the host cell surface, wherein the two or more engineered proteins interact to form a protein complex of engineered proteins, and contacting the protein complex of engineered proteins with a substrate, wherein if the protein complex of engineered proteins interacts with the substrate, the protein complex of engineered proteins can process the substrate.

In some embodiments, the invention provides a method for assaying the activity of a protein complex of engineered proteins, the method comprising inducing expression of two or more engineered proteins in a host cell, wherein the host cell displays a first binding partner on the cell surface, and wherein a) the engineered protein comprises a modification motif; b) a second binding partner is coupled to the modification motif; c) the engineered protein is secreted; and, d) the second binding partner is bound to the first binding partner on the cell surface, thereby displaying the engineered protein on the host cell surface, wherein the two or more engineered proteins interact to form a protein complex of engineered proteins, contacting the protein complex of engineered proteins with a substrate; and, assaying the activity of the protein complex of engineered proteins.

In some embodiments, the invention provides a method for evaluating if an engineered protein can process a substrate, the method comprising inducing expression of an engineered protein in a host cell, and measuring the level of a detectable signal generated by the engineered protein processing a substrate, wherein, a) the engineered protein is secreted, and b) the substrate is coupled to the host cell surface.

In some embodiments, the invention provides a method for screening candidate engineered proteins, the method comprising introducing a plurality of vectors into a population of host cells, wherein the host cell displays a first binding partner on the cell surface, wherein each vector comprises a gene encoding a unique engineered protein, inducing expression of the engineered proteins in host cells, and wherein a) the engineered protein comprises a modification motif; b) a second binding partner is coupled to the modification motif; c) the engineered protein is secreted; and d) the second binding partner is bound to the first binding partner on the cell surface, thereby displaying the engineered protein on the host cell surface, and determining if the engineered proteins have a predetermined function, wherein if the engineered protein has the predetermined function, the engineered protein is identified as a candidate engineered protein.

In some embodiments, the invention provides a method for screening candidate engineered proteins, the method comprising introducing a plurality of vectors into a population of host cells, wherein the host cell displays a first binding partner on the cell surface, wherein each vector comprises a gene encoding a unique engineered protein, inducing expression of the engineered proteins in host cells, and wherein a) the engineered protein comprises a modification motif; b) a second binding partner is coupled to the modification motif; c) the engineered protein is secreted; and, d) the second binding partner is bound to the first binding partner on the cell surface, thereby displaying the engineered protein on the host cell surface, and contacting the engineered proteins with a substrate, wherein if an engineered protein interacts with the substrate, the engineered protein is identified as a candidate engineered protein.

In some embodiments, the invention provides a method for screening candidate engineered proteins, the method comprising introducing a plurality of vectors into a population of host cells, wherein each vector comprises a gene encoding a unique engineered protein, inducing expression of the engineered proteins in the host cells, wherein a) the engineered proteins are secreted, and b) a substrate is coupled to the host cell surfaces, wherein if the engineered protein processes the substrate a detectable signal is generated, and wherein if a detectable signal is generated the engineered protein is identified as a candidate engineered protein.

In some embodiments, the invention provides a method for producing an engineered protein having a predetermined affinity for a target molecule, the method comprising introducing a plurality of vectors into a population of host cells, wherein the host cell displays a first binding partner on the cell surface, wherein each vector comprises a gene encoding a unique engineered protein, coupling a target molecule to the first binding partner, thereby immobilizing the target molecule on the cell surface, inducing secretion of the engineered proteins, binding the engineered proteins to the target molecule on the host cell surface resulting in the generation of a library of engineered proteins on the host cell surfaces, selecting a subpopulation of host cells secreting an engineered protein of interest having a predetermined affinity for the target molecule, and producing the engineered protein from the selected subpopulation of host cells.

In some embodiments, the invention provides a library of host cells, wherein each host cell comprises a vector encoding a gene for a unique engineered protein and wherein the host cell also comprises a substrate, and wherein the substrate is coupled to the host cell surface. In some embodiments, the invention provides a library of host cells, wherein each host cell expresses a unique engineered protein and comprises a substrate, wherein the substrate is coupled to the host cell surface. In some embodiments, the invention provides a library of host cells, wherein each host cell expresses a unique engineered protein and wherein each engineered protein comprises a unique polypeptide coupled to an immobilization peptide. In some embodiments, the invention provides a library of host cells, wherein each host cell displays on its surface an engineered protein and wherein each engineered protein comprises a unique polypeptide coupled to an immobilization peptide. In some embodiments, the invention provides a library of vectors, wherein each vector comprises a nucleic acid encoding a unique engineered protein and wherein each engineered protein comprises a unique polypeptide coupled to an immobilization peptide. In some embodiments, the invention provides a library of engineered proteins, wherein each engineered protein comprises a unique polypeptide coupled to an immobilization peptide.

It should be appreciated that in any of the embodiments the immobilization peptide can be linked to the C-terminus or the N-terminus of the engineered protein. It should be appreciated that in any of the embodiments the immobilization peptide can be linked to the N-terminus of the engineered protein. It should be appreciated that in any of the embodiments the engineered protein can comprise a secretion peptide. It should be appreciated that in any of the embodiments the gene encoding the engineered protein may be integrated in the genome of the cell.

It should be appreciated that in any of the embodiments the engineered protein can comprise a therapeutic polypeptide, polymerase, ligase, restriction enzyme, topoisomerase, kinase, phosphatase, metabolic enzyme, catalytic enzyme, therapeutic enzyme, pharmaceutical enzyme, environmental enzyme, industrial enzyme, pharmaceutical polypeptide, environmental polypeptide, industrial polypeptide, binding protein, antibody, antibody fragment, signaling molecule, cytokine or a receptor. It should be appreciated that in any of the embodiments the engineered protein can comprise a polymerase. It should be appreciated that in any of the embodiments the polymerase can be a phi 29 polymerase.

It should be appreciated that in any of the embodiments the engineered protein can be a scaffold protein. It should be appreciated that in any of the embodiments the engineered protein can comprise a reporter moiety.

It should be appreciated that in any of the embodiments the immobilization peptide can be a transmembrane polypeptide. It should be appreciated that in any of the embodiments the immobilization peptide can be a polypeptide membrane anchor. It should be appreciated that in any of the embodiments the immobilization peptide can be a GPI-linked polypeptide. It should be appreciated that in any of the embodiments the immobilization peptide can be a natural surface polypeptide. It should be appreciated that in any of the embodiments the natural surface polypeptide can be Aga2.

It should be appreciated that in any of the embodiments the coupling the second binding partner can be done in vivo by a coupling enzyme. It should be appreciated that in any of the embodiments the coupling the second binding partner can be catalyzed in vivo by a coupling enzyme. It should be appreciated that in any of the embodiments the method can further comprise expressing a coupling enzyme. It should be appreciated that in any of the embodiments the coupling enzyme can be expressed from a vector. It should be appreciated that in any of the embodiments the gene encoding the coupling enzyme can be integrated in the genome of the cell. It should be appreciated that in any of the embodiments the coupling enzyme can be biotin ligase. It should be appreciated that in any of the embodiments the coupling enzyme can be BirA. It should be appreciated that in any of the embodiments the coupling enzyme can be Bpl1.

It should be appreciated that in any of the embodiments the modification motif can be a biotinylation peptide. It should be appreciated that in any of the embodiments the biotinylation peptide can have a sequence recognized by BirA. It should be appreciated that in any of the embodiments the second binding partner can be biotin.

It should be appreciated that in any of the embodiments the second binding partner can be a carbohydrate binding domain. It should be appreciated that in any of the embodiments the carbohydrate binding domain can be a lectin. It should be appreciated that in any of the embodiments the lectin can be concanavalin A. It should be appreciated that in any of the embodiments the lectin can be Phytohemaglutinin. It should be appreciated that in any of the embodiments the carbohydrate binding domain can be the sugar-binding domain of a flocculation protein. It should be appreciated that in any of the embodiments the flocculation protein can be selected from the group consisting of Flo1, Flo5 and Flo11. It should be appreciated that in any of the embodiments the carbohydrate binding domain can be a carbohydrate binding module. It should be appreciated that in any of the embodiments the carbohydrate binding module can be a cellulose binding domain.

It should be appreciated that in any of the embodiments the method can further comprise introducing a vector comprising a gene encoding the first binding partner in the host cells, and incubating the host cells under conditions sufficient for expressing the first binding partner on the host cell surface. It should be appreciated that in any of the embodiments the first binding partner can be avidin, streptavidin or neutravidin. It should be appreciated that in any of the embodiments the first binding partner can comprise at least one monomer of an avidin or avidin like protein. It should be appreciated that in any of the embodiments the first binding partner can be a fusion protein. It should be appreciated that in any of the embodiments the fusion protein can comprise an anchoring motif. It should be appreciated that in any of the embodiments the anchoring motif can be selected from the group consisting of GPI anchor, modified GPI anchor, α-agglutinin, α-agglutinin, flocculation protein, major cell wall proteins, CCW14, CIS3, CWP1, PIR1, and PIR3. It should be appreciated that in any of the embodiments the fusion protein can comprise a secretion peptide. It should be appreciated that in any of the embodiments the first binding partner can be expressed as a single polypeptide. It should be appreciated that in any of the embodiments the first binding partner can be connected to the cell surface through a biotin spacer. It should be appreciated that in any of the embodiments the biotin spacer can comprise a PEG moiety. It should be appreciated that in any of the embodiments the first binding partner can be biotin. It should be appreciated that in any of the embodiments in the first binding partner can be a biotin binding protein or portion thereof.

It should be appreciated that in any of the embodiments the conditions for expressing the engineered protein and the first binding partner can be different. It should be appreciated that in any of the embodiments the conditions for expressing the engineered protein and the first binding partner can be the same. It should be appreciated that in any of the embodiments the condition can comprise the addition of an agent to the environment of the host cell. It should be appreciated that in any of the embodiments the condition can comprise a change in temperature of the environment of the host cell. It should be appreciated that in any of the embodiments the condition can comprise a change in carbon source of the host cell. It should be appreciated that in any of the embodiments the first binding partner can be covalently conjugated to the cell surface. It should be appreciated that in any of the embodiments the method can further comprise the expression of a chaperone polypeptide.

It should be appreciated that in any of the embodiments the cell can be a mammalian cell. It should be appreciated that in any of the embodiments the cell can be a yeast cell. It should be appreciated that in any of the embodiments the cell can be *S. cerevisiae*. It should be appreciated that in any of the embodiments the cell can be a bacterial cell. It should be appreciated that in any of the embodiments the cell can be *E. coli*. It should be appreciated that in any of the embodiments the cell can be a cell that has a reduced level of protease activity. It should be appreciated that in any of the embodiments the cell can be expressing a chaperone protein.

It should be appreciated that in any of the embodiments the substrate can be coupled to the cell surface. It should be appreciated that in any of the embodiments the substrate can be a polypeptide, nucleic acid, lipid, polysaccharide, synthetic polymer or synthetic compound. It should be appreciated that in any of the embodiments the substrate can be coupled to the cell prior to inducing expression. It should be appreciated that in any of the embodiments the substrate can be coupled to the cell after expression has been induced. It should be appreciated that in any of the embodiments the substrate can be a moiety not naturally present on the host cell surface. It should be appreciated that in any of the embodiments the substrate can be coupled to a moiety naturally present on the host cell surface. It should be appreciated that in any of the embodiments the substrate can be coupled to an amino acid side chain of a polypeptide. It should be appreciated that in any of the embodiments the substrate can comprises biotin. It should be appreciated that in any of the embodiments the substrate can be immobilized on the cell surface through binding of the biotin to a binding moiety. It should be appreciated that in any of the embodiments the substrate can comprise a nucleic acid. It should be appreciated that in any of the embodiments the substrate can comprise a template and a primer.

It should be appreciated that in any of the embodiments processing of the substrate can comprise binding to the substrate, dissociating the substrate, nicking the substrate, cutting the substrate, activating the substrate, deactivating the substrate, charging the substrate, decharging the substrate, changing substrate conformation, copying the substrate, replicating the substrate, conjugating molecules to the substrate, conjugating peptides to the substrate or modifying the substrate. It should be appreciated that in any of the embodiments the threshold level can be the level of signal of a control polypeptide. It should be appreciated that in any of the embodiments the method can further comprise contacting the engineered proteins with a substrate results in a signal, and wherein if the level of the signal is above a threshold level, the engineered protein is identified as a candidate engineered protein.

It should be appreciated that in any of the embodiments the control polypeptide or control protein can be a polypeptide with random coil structure. It should be appreciated that in any of the embodiments the control polypeptide or protein can be a wild type polypeptide. It should be appreciated that in any of the embodiments the control polypeptide or control protein can be a commercially available polypeptide. It should be appreciated that in any of the embodiments substrate processing can comprise adding one or more nucleotides to a primer. It should be appreciated that in any of the embodiments substrate processing can comprise adding one or more nucleotide comprising a fluorescent moiety to a primer. It should be appreciated that in any of the embodiments the method can further comprise comparing the detectable signal to a signal of a control protein. It should be appreciated that in any of the embodiments the act of isolating the candidate engineered polypeptide can be based on identifying a detectable signal above a threshold level. It should be appreciated that in any of the embodiments the detectable signal can be generated by the engineered protein.

It should be appreciated that in any of the embodiments the detectable signal can be generated by processing the substrate. It should be appreciated that in any of the embodiments the detectable signal can be generated both by the engineered protein and by processing the substrate. It should be appreciated that in any of the embodiments the detectable signal can be a fluorescent signal. It should be appreciated that in any of the embodiments the act of isolating the candidate engineered polypeptide can comprise a fluorescence activated cell sorting act.

It should be appreciated that the invention also comprises the candidate engineered proteins identified by any of the embodiments of the invention.

It should be appreciated that in any of the embodiments the engineered protein can be an antibody or an antibody fragment and the target molecule can be an antigen. It should be appreciated that in any of the embodiments the engineered protein can be an antigen and the target molecule can be an antibody or antibody fragment. It should be appreciated that in any of the embodiments the engineered protein can be an antigen. It should be appreciated that in any of the embodiments the engineered protein can be an antibody or antibody fragments. It should be appreciated that in any of the embodiments the engineered protein can be a receptor and the target molecule can be a ligand.

It should be appreciated that in any of the embodiments the library can have at least 2, at least 5, at least 10, at least 50, at least 100, at least 1000, at least 10,000, at least 100,000, at least 1,000,000, at least $10^7$, at least $10^8$, at least $10^9$, at least $10^{10}$ or at least $10^{11}$ members. It should be appreciated that in any of the embodiments the host cell can displays at least $10^4$ engineered proteins per cell. It should be appreciated that in any of the embodiments the immobilization peptide can be a biotinylation peptide. It should be appreciated that in any of the embodiments the immobilization peptide can be a transmembrane polypeptide. It should be appreciated that in any of the embodiments the immobilization peptide can be a polypeptide membrane anchor. It should be appreciated that in any of the embodiments the immobilization peptide can be a GPI polypeptide. It should be appreciated that in any of the embodiments the immobilization peptide can be a natural surface polypeptide.

It should be appreciated that in any of the embodiments the reporter moiety can be a fluorescent protein. It should be appreciated that in any of the embodiments the method can further comprise binding of a detectable agent to the reporter moiety. It should be appreciated that in any of the embodiments the detectable agent can be an antibody. It should be appreciated that in any of the embodiments the antibody can comprise a fluorescent moiety.

Each of the limitations of the invention can encompass various embodiments of the invention. It is, therefore, anticipated that each of the limitations of the invention involving any one element or combinations of elements can be included in each aspect of the invention. This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including," "comprising," or "having," "containing", "involving", and variations thereof herein, is meant to encompass the items listed thereafter and equivalents thereof as well as additional items.

BRIEF DESCRIPTION OF THE DRAWINGS

FIG. 3A shows a negative control of labeling with biotinylated fluorescence. FIG. 3B shows the conjugation with avidin through labeling with biotinylated fluorescence. FIG. 3C shows the stability of the avidin-cell connection over time.

FIG. 4A shows a biotinylated engineered cell wall protein expressed at the cell surface. FIG. 4B shows the avidin binding to the biotinylated cell wall protein. FIG. 4C shows the binding of avidin-fluorescein to populations of cells expressing or not expressing the biotinylated engineered cell wall protein. FIG. 4D shows the binding of biotin-fluorescein to the avidin bound to the biotinylated engineered cell wall protein.

FIGS. 5A-5F illustrate an embodiment of the expression and display of a protein of interest at a cell surface. FIG. 5A illustrates a cell transformed with a vector encoding an engineered protein comprising a protein of interest fused to biotin acceptor protein (BAP) and to an epitope tag. FIG. 5B illustrates biotinylation of the cell surface. FIG. 5C illustrates the binding of avidin to the biotin at the cell surface. FIG. 5D illustrates the expression of the protein of interest fused to the BAP and the epitope-tag (FLAG) and the expression of the biotin ligase. FIG. 5E illustrates the in vivo biotinylation of the engineered protein. FIG. 5F illustrates the secretion of the engineered biotinylated protein and its binding to the avidin displayed at the cell surface.

FIG. 6A illustrates the binding of an antigen to an antibody (a target molecule) displayed at the cell surface through its binding to avidin, which in turn is bound to the biotin at the cell surface. FIG. 6B illustrates the labeling of the antigen. FIG. 6C illustrates the labeling of both the antigen and the displayed antibody.

FIG. 7A illustrates the constructs encoding an scFv protein comprising a promoter, a secretory leader sequence (SL), an epitope-Tag, the ORF encoding the scFv protein, a biotin acceptor peptide (BAP) and a mating factor alpha terminator sequence. FIG. 7B illustrates the constructs encoding an scFv protein comprising a promoter, a secretory leader sequence (SL), a biotin acceptor peptide (BAP), the ORF encoding the scFv protein, an epitope-Tag, and a mating factor alpha terminator sequence. FIG. 7C illustrates the scFv protein with a BAP at its C-terminus and a FLAG epitope at its N-terminus FIG. 7D illustrates the scFv protein with a FLAG epitope at its C-terminus and a BAP at its N-terminus.

FIG. 8A illustrates the expression of the scFv protein and the labeling with an antibody recognizing the FLAG epitope and the HIS6 of the antigen. FIG. 8B shows an assay for the enrichment of a population of cells expressing the antigen-binding scFv protein. FIG. 8C shows an assay for the enrichment of a population of cells expressing the antigen-binding scFv protein. FIG. 8D is a diagram showing the enrichment of a sample.

FIG. 9A shows an embodiment where the antibody is expressed at the cell surface. FIG. 9B shows an assay for the enrichment of a population of cells expressing the antibody through antigen binding.

FIG. 12A shows binding of biotin-fluorescein to avidin bound to a biotinylated cell wall protein in the absence of nocodazole. FIG. 12B shows labeling with the antigen and anti-FLAG antibody in the absence of nocodazole. FIG. 12 C shows binding of biotin-fluorescein to avidin bound to a biotinylated cell wall protein in the presence of nocodazole. FIG. 12 D shows labeling with the antigen and anti-FLAG antibody in the presence of nocodazole.

FIG. 14A shows a non-limiting embodiment of a fluorescent signal of an assay comprising a single-stranded oligonucleotide immobilized on the surface of yeast with an avidin sandwich. A FAM labeled non-complementary oligonucleotide was added to the cells. Specific binding of the complementary oligonucleotide is shown by FITC fluorescence. FIG. 14B shows a non-limiting embodiment of a fluorescent signal of an assay comprising a single-stranded oligonucleotide immobilized on the surface of yeast with an avidin sandwich. A FAM labeled complementary oligonucleotide was added to the cells. Specific binding of the complementary oligonucleotide is shown by FITC fluorescence.

DETAILED DESCRIPTION

Figure 1:
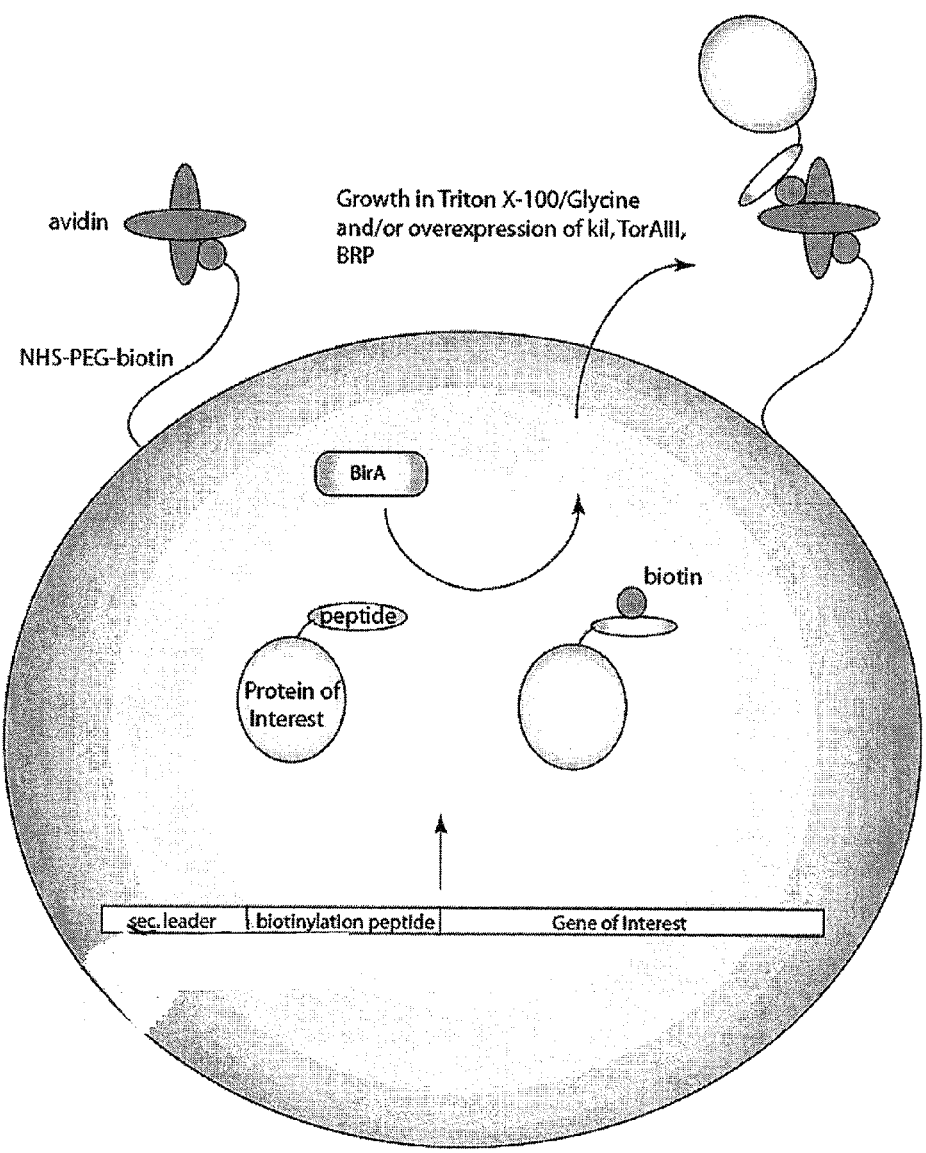
FIG. 1 illustrates a non-limiting overview of the expression of an engineered protein comprising a protein of interest linked to a biotinylation peptide (a second binding partner) wherein avidin (the first binding partner) is linked to the cell surface by a linker.

Aspects of the invention relate to methods and compositions for displaying one or more cellularly expressed molecules on a cell surface. In some embodiments, the molecules (e.g., engineered proteins) are expressed in host cells under conditions resulting in their immobilization (e.g., the immobilization of the engineered proteins) on the cell surface. Aspects of the invention are useful to immobilize one or more proteins on a cell in which they are synthesized, thereby associating each of the one or more proteins with their genotype. The displayed protein(s) may be interrogated using any suitable assay or experimental system to evaluate one or more properties or functions of the protein (e.g., binding properties, enzymatic activity, stability, etc., or any combination thereof). Preferred assays maintain the integrity of the host cell so that the genotype of a protein being evaluated can be retrieved (e.g., by characterizing the nucleic acid that encoded the protein) if desired. In some embodiments, a single protein of interest may be displayed and evaluated using compositions and methods of the invention. In certain embodiments, a library of different proteins may be evaluated. Each different protein may be encoded by a different nucleic acid in a different host cell of the library. The different proteins may be variants that are being evaluated to identify or select for novel and/or improved properties (e.g., increased activity, increased stability, increased binding affinity, etc., or any combination thereof). In some embodiments, the variants share a common amino acid sequence for much of the protein, but differ in amino acid sequence in areas that are suspected of being structurally and/or functionally important. For example, antibody variants may share one or more common framework sequences, but have different variable sequences (e.g., with different CDR sequences). Receptor libraries may include receptor variants with different amino acid sequences in their ligand binding domains. Similarly, enzyme libraries may include enzyme variants with different sequences in their active site regions. Aspects of the invention may be used to display and evaluate large numbers of variants so that a large sequence space may be sampled and tested. In some embodiments, each host cell expresses and displays only one type of protein variant to be evaluated. However, aspects of the invention may be useful to express and display many copies of the protein on the cell surface. The high capacity of display systems of the invention is useful to effectively and efficiently assay the displayed protein (e.g., in high throughput assays). In certain embodiments, a single host cell may express and display two or more (e.g., 2, 3, 4, 5, 6, 7, 8, 9, 10, or more) different protein variants (e.g., for evaluating pools of proteins).

Other aspects of the invention relate to methods and compositions for producing a molecule of interest in a cell. In a preferred embodiment, the molecule of interest is a protein or a polypeptide. As used herein, the terms "protein" and "polypeptide" are used interchangeably. The term "engineered protein" encompasses naturally occurring proteins and synthetic polypeptides and protein constructs that comprise a synthetic polypeptide or naturally occurring protein linked to additional polypeptide elements, like, for instance, an immobilization peptide, reporter peptide or secretion peptide. Proteins may or may not be made up entirely of amino acids. Examples of classes of proteins that include other non amino acid constituents include, but are not limited to, glycoproteins, lipoproteins and proteoglycans. According to aspects of the invention, engineered proteins are encoded and/or expressed from a recombinant nucleic acid that may be engineered to include sequence variants, recombinant promoters, transcriptional control elements, fusion peptides, other modifications, or any combination of two or more thereof. In some embodiments proteins are displayed on the cell surface by immobilization of the protein. In some embodiments of the invention, proteins may be immobilized on a cell surface via a peptide that is membrane or surface bound. In certain embodiments, immobilization may involve specific interactions between binding partners. For example, a protein of interest is attached to a host cell surface through the interaction between a first and a second binding partner. In some embodiments, a first binding partner may be attached at the host cell surface and an engineered protein may include a second binding partner that interacts specifically with the first binding partner (e.g., with a binding affinity represented by a dissociation constant of about $10^{-7}$ M, about $10^{-8}$ M, about $10^{-9}$ M, about $10^{-10}$ M, about $10^{-11}$ M, about $10^{-12}$ M, about $10^{-13}$ M, about $10^{-14}$ M or about $10^{-15}$ M). In some embodiments, engineered proteins comprise a modification motif that is modified by a coupling enzyme, resulting in the coupling of a second binding partner to the modification motif. In some embodiments, the second binding partner is coupled to the engineered protein intracellularly.

In some embodiments, a target molecule (e.g., a target protein) is attached to the cell surface directly and the expressed engineered protein binds to the target protein, thereby displaying the expressed protein. In some embodiments, the target molecule is not attached directly to the host cell but is attached to a second binding partner that binds a first partner that is attached to the host cell. Non-limiting embodiments of engineered protein and target molecule combinations are, the engineered protein is an antibody and the target molecule an antigen, the engineered protein is an antigen and the target molecule an antibody, the engineered protein is a receptor and the target molecule is a ligand, the engineered protein is an enzyme and the target molecule is a substrate, etc., or any combination thereof.

In some embodiments the host cell is induced to express the engineered protein. In some embodiments, no induction step is necessary and incubating the host cell will result in the expression of the engineered protein. In some embodiments, engineered proteins comprising the second binding partner are secreted and bind to the first binding partner, thereby displaying the engineered protein on the cell surface. In some embodiments, the first binding partner is avidin and the second binding partner is biotin. In some embodiments, avidin is covalently conjugated to the cell surface (e.g., directly or indirectly). Yet in some embodiments, the first binding partner is expressed by the cell and displayed at the host cell surface. For example, one of the binding partners may be expressed by the host cell as a fusion protein such as a cell wall or a membrane fusion protein and displayed at the surface of the host cell.

Immobilization of Proteins

In some embodiments, secreted engineered proteins are immobilized on the cell surface. The invention embraces any method of immobilizing the engineered protein on the cell surface including anchoring of the engineered protein to the cell directly, e.g., if the fusion protein comprises a cell membrane anchor (like a GPI motif), or if the fusion protein is an integral part of a protein anchored to the membrane. The invention also embraces methods of immobilizing the engineered proteins on the cell surface to components that are naturally present on the cell surface, or components that can be introduced on the cell surface through overexpression. The engineered proteins can subsequently be immobilized for instance through sulfide links (as in the case of AGA) or through linking to a sugar residue. The immobilization can be spontaneous (e.g., no change in the condition of the host cell is necessary) or the immobilization of the engineered proteins may require an active step, such as the addition of an agent to the host cell environment, or the triggering of a coupling reaction by temperature or light. Other active coupling steps embraced by the invention are the induction of expression, or regulation of expression, of a protein that can facilitate immobilization of the engineered protein to the cell surface Immobilization may also require the addition of a linker, spacer, or any agent that can link the engineered protein to the cell wall.

In some embodiments, the engineered proteins are immobilized through an amino acid modification. However, the invention is not so limited, and the engineered proteins may be immobilized through any one or more amino acids, amino acid side chains, amino acid backbone, and multiples and combinations thereof. In some embodiments, the engineered proteins are immobilized through an immobilization peptide. In some embodiments, the engineered proteins are immobilized and displayed at the cell surface through the interaction between two binding partners having an affinity to one another, for example avidin-biotin, streptavidin-biotin, neutravidin-biotin, etc., or any combination thereof. In one aspect of the invention, the first binding partner and the engineered protein fused with the second binding partners (e.g., in vivo biotinylated proteins) are co-expressed and secreted by the host cell. Consequently, binding partners may associate intracellularly or at the cell surface. In one embodiment, the two binding partners associate intracellularly and are exported and displayed at the cell surface as a complex. In another aspect of the invention, the first binding partner and the engineered protein fused with the second binding partner are secreted separately. If the two binding partners are expressed separately, the expression of the first binding partner may be regulated such that the first binding partner is expressed in sufficient amount to bind the majority of the engineered protein fused to the second binding partner, or the expression of the fusion protein is regulated such that the fusion protein is expressed in sufficient amount to be displayed at the cell surface of the secreting cell but in insufficient amount to bind to other cells in a cell population (at least not at detectable levels).

In some embodiments, the host cells are incubated in presence of a substance slowing down the cell expression product diffusion in the media. One should appreciate that by increasing the viscosity of the liquid medium, the protein expressed by the host cell will be more likely to be captured by the secreting cell than by a non-secreting cell. Methods to slow down the diffusion of protein in a liquid are known in the art and include for example PEG, gelatin etc., or any combination thereof.

Display and Screening

Aspects of the invention provide compositions and methods for displaying molecules (e.g., proteins) on a cell surface. In some embodiments, compositions and methods are provided for the display of high molecular weight proteins on a cell surface.

Aspects of the invention may be useful to identify one or more molecules having a predetermined function of interest. By providing a system that displays a cellularly expressed protein on the surface of the cell in which it is expressed, cells that express proteins of interest can be identified using any assay that can be performed on a cell surface (e.g., performed on a cellular preparation to detect one or more molecules that are displayed on the cell surface). Aspects of the invention can be used to screen libraries expressing protein variants to identify one or more proteins of interest. As used herein a "variant" may refer to a polypeptide or polynucleotide that differs from a reference polypeptide or polynucleotide, but retains essential properties. A typical variant of a polypeptide differs in amino acid sequence from another reference polypeptide. Generally, differences are limited so that the sequences of the reference polypeptide and the variant are closely similar overall and, in many regions, identical. A variant and reference polypeptide may differ in amino acid sequence by one or more modifications (e.g., substitutions, additions, and/or deletions). A variant of a polypeptide may be a conservatively modified variant. A substituted or inserted amino acid residue may or may not be one encoded by the genetic code (e.g., a non-natural amino acid). A variant of a polypeptide may be naturally occurring, such as an allelic variant, or it may be a variant that is not known to occur naturally.

Aspects of the invention provide optimized methods for identifying a genotype coding for a protein of interest. By identifying proteins of interest with a reporter moiety (e.g., directly or indirectly coupled with a fluorescent moiety) or through a functional assay, cells expressing the protein of interest can be isolated easily. Aspects of the invention provide methods for identifying proteins of interest through the amount of protein expressed on the cell surface. Aspects of the invention provide opportunities for performing a broad range of assays on cell surfaces, because of the high number and/or high concentration of cellularly expressed molecules that can be displayed on a cell surface. Cells expressing a protein of interest may be selected based on their affinity to a target molecule, antigen, ligand, substrate etc., or any combination thereof. Aspects of the invention provide methods for the co-immobilization of expressed proteins and their substrates or potential substrates on a cell surface. Cells expressing a protein of interest may be isolated using Fluorescence Activated Cell Sorting (FACS), or any other suitable cell sorting method, or any other high throughput cell screening and/or isolation method.

One aspect of the present invention provides a method for selecting host cells displaying proteins with desirable affinity or specificity for a target molecule (e.g., ligand or antigen) and secreting high levels of protein of interest. In an exemplary embodiment, in vivo or in vitro biotinylated host cells are first incubated in the presence of soluble avidin and with a biotinylated ligand or antigen. The engineered protein of interest having an affinity for the ligand or antigen can be expressed in host cells. The expression of the engineered protein results in the immobilization of engineered proteins having an affinity for the target molecule on the cell surface. Cells expressing the protein of interest bound to the target molecule can be detected based on a reporter moiety of the secreted protein or with a labeled antibody against the protein of interest. Host cells displaying proteins having desirable affinity or selectivity for the target molecule or host cells expressing a desirable level of the protein of interest can be selected based on the intensity of the detectable label. Selected host cells may then be incubated in absence of the biotinylated antigen and under conditions favorable for the expression and secretion of the engineered protein comprising a modification motif. In a preferred embodiment, the modification motif is a biotin acceptor peptide and the engineered protein is biotinylated in vivo. The expression of the engineered protein results in the immobilization of the protein on the host cell surface through the binding of the biotinylated protein to an avidin-like protein on the cell surface. On should appreciate that if high secretor host cells were selected during the first selection process, host cells displaying the protein of interest on their cell surface can then be incubated with a labeled target molecule (e.g., epitope tag antigen or ligand). Host cells can subsequently be screened and selected based, for example, on the affinity or specificity for a target molecule as discussed above. Yet in another embodiment, host cells are first selected during the first selection process for displaying protein with a desirable range of affinity or specificity for a target molecule, and can be subsequently screened and selected based on the expression level of the engineered protein. The expression level can be determined by quantitation of a detectable label associated to the engineered protein of interest (e.g., labeled antibody against the protein of interest, or if the protein of interest is fused with an epitope, detectable anti-epitope antibody).

In Vitro Protein Evolution

In vitro protein evolution allows for a large number of protein functions and characteristics to be investigated. In some aspects, in vitro protein evolution comprises two general steps: diversification and selection. Diversification relies on the ability to generate highly diverse libraries of nucleic acids coding for proteins. Selection can be achieved by screening the libraries for a desired phenotype and linking the phenotype to the genotype, e.g., by identifying the member of the library that comprises the genotype that is responsible for the observed phenotype. Nucleic acid libraries can be generated through a variety of methods including through the introduction of mutations such as point mutations, deletions, and insertions, or through recombination events. Methods for the generation of libraries of variants are known in the art and include error-prone PCR, synthesis of DNA in DNA repair compromised bacteria, and chemical modification of DNA. Methods for the generation of libraries through recombination are known in the art and include gene shuffling, assembly of DNA in highly recombinogenic bacteria, synthetic nucleic acid library assembly, etc., or any combination thereof.

In some embodiments, the second step of in vitro protein evolution is selection. For a candidate protein to be selected, the variant library, or components of the variant library, and the desired functions and characteristics of the library members have to be evaluated. In an ideal case, each component of the library is available for evaluation. Protein libraries may be encoded by nucleic acid libraries, and the nucleic acids thus have to be expressed and the proteins secreted and/or displayed to be available for evaluation of a specific phenotype (e.g., using an assay that interrogates cell surface or extracellular properties). In in vitro display systems, proteins are expressed and presented, thereby making them available for evaluation by linking them to a component of the expression system. In in vivo display systems, the proteins are expressed in an organism and displayed on the surface of that organism. For an overview of certain protein display technologies see Sergeeva et al. (2006, Advanced Drug Delivery Reviews 58: 1622-1654).

A library of nucleic acids can be introduced into a plurality of host cells resulting in the expression of a member of the library in each of the host cells. In addition to being expressed, the proteins have to be presented to evaluate their function or characteristic. While the proteins can be evaluated after they are secreted from the host cell into the supernatant, it is easier to evaluate proteins if they are immobilized. In addition, immobilization makes it easier to identify the host cell that expresses a protein of interest. A variety of techniques have been developed for protein expression and display. Examples of these systems are ribosome display, mRNA display, DNA display, phage display and cell surface display. These displays are based on the ability to physically link the polypeptide produced by a library member to its corresponding genotype.

Aspects of the invention further relate to methods and compositions for linking a polypeptide produced by a library member for its corresponding genotype.

Immobilizing Engineered Proteins on Cell Surfaces

In one aspect, the invention provides methods for immobilizing engineered proteins on a cell surface. In some embodiments, the engineered proteins of the invention minimally comprise a polypeptide of interest and an immobilization peptide. In some embodiments, the engineered protein comprises a fusion protein. In some embodiments, the engineered proteins are immobilized on the cell surface through the introduction of an amino acid modification on the engineered protein. In some embodiments, the amino acid modification is done in vivo (e.g., intracellularly). In some embodiments, the modification is performed extracellularly, for instance, immediately after the engineered protein traverses the cell membrane. In some embodiments, the amino acid to be modified is part of a modification motif. It should be appreciated that the modification motif can be an integral part of the engineered protein or it can be located on a peptide sequence that is linked to the N-terminus or C-terminus of the protein of interest, or any combination thereof. In some embodiments, the peptide sequence that comprises the modification motif is an immobilization peptide. In some embodiments, the immobilization peptide is not directly fused to the protein of interest, but a spacer sequence is incorporated between the immobilization peptide and the protein of interest. In some embodiments, a spacer sequence is a sequence of amino acid that inserted between the protein of interest and the immobilization to allow for folding of the protein of interest and/or modification of the immobilization peptide. In some embodiments, the spacer peptide is 5, 10, 15, 20, 50, 100 or up to 1000 amino acid residues.

In some embodiments, the engineered protein further comprises a leader peptide. As used herein, the term leader peptide or secretion peptide or secretion leader peptide refers to any signaling sequence that directs a synthesized fusion protein away from the translation site, including signaling sequences that will result in the fusion peptide crossing the cell membrane and being secreted. The leader peptide or secretion peptide may be proteolytically removed from the mature protein concomitant or immediately following export of the protein into the lumen of intracellular compartment along the secretory pathway. The leader peptide may be a naturally occurring sequence or a synthetic sequence. In some embodiments, the leader peptide comprises the modification motif. It should be appreciated that the invention embraces any sequence order of protein of interest, immobilization peptide and leader peptide and that these elements may be separated by spacer sequence, for instance an engineered protein can be characterized by leader sequence—protein of interest—spacer immobilization peptide, or protein of interest—leader peptide—immobilization peptide. However, other sequence orders may be used as the invention is not limited in this respect.

In some aspects of the invention, the engineered protein is immobilized through the interaction with a target molecule on the cell surface. For the purpose of the invention, the term target molecule refers to a molecule that binds with a binding specificity to a protein such as an antibody, an antibody fragment, or an antibody-like polypeptide, a receptor, an antigen, an enzyme etc., or any combination thereof. The target molecule can be for example an antigen, an epitope, a ligand, a substrate, etc., or any combination thereof. It should be appreciated that the term "target molecule" can be used to refer to a substrate such as an enzymatic substrate or a molecule that is being evaluated for binding (e.g., a ligand, eptiope, antigen, multimerization partner such as a homo or hetero dimeric partner, etc., or any combination thereof). Accordingly, general descriptions herein related to "target molecule" may be applied to embodiments relating to substrates and/or binding molecules.

In some embodiments, the target molecule is attached to the cell surface directly. In some embodiments, the expressed engineered protein binds to the target molecule, thereby displaying the engineered protein on the cell surface. However, in some embodiments where the target molecule is a substrate, the engineered protein may no bind with sufficient affinity to be immobilized or displayed on the surface of the host cell. In these embodiments, an enzymatic reaction may be catalyzed on the cell surface by the engineered protein. In some embodiments, a product (e.g., a detectable product) may be immobilized on the cell surface. In some embodiments, a product (e.g., a detectable product) may be released from the cell surface. In some embodiments, a cell displaying a first binding partner at its surface binds a soluble target molecule linked to a second binding partner thereby immobilizing the target molecule on its surface. One should appreciate that the target or substrate molecule linked to a second binding partner may be immobilized on the host cell surface through binding of the second binding partner to a suitable first binding partner attached to the cell surface. For example, a substrate may comprise (e.g., may be linked to) biotin and may be immobilized on the host cell surface through its interaction with for example avidin, Neutravidin, streptavidin or any other suitable binding moiety, or any combination thereof, acting as a first binding partner. The first binding partner may be directly or indirectly displayed, attached, coupled to the host cell surface. For example, avidin or an avidin-like protein may be the first binding partner and may be linked to the cell surface by a variety of methods described herein. For example, biotin may be chemically coupled to the cell surface and soluble avidin or avidin-like protein may be added extracellularly, or biotin may be chemically attached to the cell surface via a suitable linker and soluble avidin or avidin-like protein may be added extracellularly, or a cell surface protein (e.g., a cell wall protein or membrane protein) may be expressed as a biotinylated protein (e.g., via in vivo biotinylation) and avidin or an avidin-like protein may be added extracellularly. Alternatively, a cell surface fusion protein comprising avidin may be expressed, for instance, or avidin may be conjugated to the cell wall and soluble biotin may be added.

It should be appreciated that the invention embraces any first binding partner and/or second binding partner. As used herein, binding partners refer to molecules that bind to each other with sufficient affinity for immobilizing a protein or other molecule on a cell surface under conditions suitable for aspects of the invention. Although many examples are described in the context of biotin and avidin, it should be appreciated that any suitable binding partners may be used. For instance, a cyclic peptide motif has been shown to bind to Neutravidin and avidin (Meyer et al., 2006, Chem. Biol. Drug Des. 68: 3-10; Gaj et al., 2007, Protein Expr. Pur. 56(1):54-61). In another exemplary embodiment, the first binding partner is a six-residue cyclic peptide including a DXaAXbPXc wherein Xa is R or L, Xb is S or T and Xc is Y or W (SEQ ID NO: 12) and the second binding partner is avidin, neutravidin, or any other suitable binding moiety. However, in some embodiments, the identity of the first and second binding partners may be swapped as described herein.

In some embodiments, the engineered protein is a fusion protein that can bind to the cell wall directly. In some embodiments, the fusion protein is a cell surface protein. In some embodiments, the engineered protein is expressed and displayed on the cell surface through binding to the cell surface directly. In some embodiments, the engineered protein is displayed on the cell surface because the cell surface protein binds to the cell surface.

In another aspect, the invention provides for methods for displaying a first binding partner on a cell surface by expressing a cell surface protein coupled with a second binding partner and binding a first binding partner to the second binding partner.

Vectors

One or more engineered proteins of the invention may be encoded by nucleotide sequences. In some embodiments, the nucleotide sequences are located on a nucleic acid vector (e.g., containing one or more additional sequences useful for replication, selection, etc., or any combination thereof). It should be appreciated that the invention covers any vector comprising nucleic acids including plasmid, phage, viruses, etc., or any other suitable nucleic acid vector. The vectors can be introduced into a host cell prior to expression of the engineered protein. The vectors can be introduced by any means including transfection, electroporation, infection, active protein transport or through any other means of introducing a nucleic acid into a cell. The vectors can be introduced immediately prior to expression, or the vectors can be introduced many cell divisions prior to expression. The vectors can be integrated into the genome of the host cell. The vectors can also be maintained as independent entities within the cells. The vectors may be replicating or non-replicating vectors. The invention also embraces collections or libraries of vectors and libraries of cells that have taken up the vectors. In some embodiments, one or more nucleic acids encoding engineered protein(s) may be integrated into the genome of a host cell without any additional vector sequences.

The vector may contain a variety of regulatory elements for maintenance of the cell or expression of the engineered protein. Regulatory elements include promoters and markers that allow for positive identification of cells that have take up the vector. The regulatory elements may be species specific. Regulatory elements are known in the art and the invention embraces any single or combination of regulatory elements needed or desired to express the engineered proteins.

Proteins

The invention embraces any engineered protein, protein domain, or functional part thereof. Engineered proteins that are particularly embraced by the invention are engineered proteins that are functional proteins, binding proteins, antibodies, scaffold proteins or enzymes. However, in some embodiments, an engineered protein of the invention may be a structural protein, a storage protein, or any other protein of interest. A protein or enzyme of the invention may be, but is not limited to, a therapeutic polypeptide, polymerase, ligase, restriction enzyme, topoisomerase, kinase, phosphatase, metabolic enzyme, catalytic enzyme, therapeutic enzyme, pharmaceutical enzyme, environmental enzyme, industrial enzyme, pharmaceutical polypeptide, environmental polypeptide, industrial polypeptide, binding protein, antibody, antibody fragment, single antibody chain, chimeric antibody, scaffold protein, immunotoxin, antibody-like polypeptide, signaling molecule, cytokine or a receptor. In some embodiments, an engineered protein is a polymerase.

Antibodies

In some embodiments, engineered proteins are antibodies, antibody chains or antibody fragments. In some embodiments, the engineered proteins include a protein of interest that is an antibody, antibody chain or antibody fragment. Typical antibodies have a tetrameric structure with two identical pairs of light and heavy chains. Both light and heavy chains have, at their amino-terminus, a variable region responsible for the specific binding to a target antigen. The carboxy-terminal region of each chain defines a constant region. The antibodies or fragments thereof may be selected for their ability to bind a specific antigen. In some embodiments, the antibody or fragment thereof is an IgG1, IgG2, IgG3, IgG4, IgM, IgA1, IgA2, IgAsec, IgD, IgE or has an immunoglobulin constant and/or variable domain of IgG1, IgG2, IgG3, IgG4, IgM, IgA1, IgA2, IgAsec, IgD or IgE. In other embodiments, the antibody is a bispecific or multispecific antibody. In still other embodiments, the antibody is a recombinant antibody, a polyclonal antibody, a monoclonal antibody, a humanized antibody, a single chain antibody, or a chimeric antibody, or a combination of two or more thereof. In some embodiments, the antibody is a human antibody. An antibody fragment of the invention may be, but is not limited to, a Fab fragment, a F(ab')$_2$ fragment, a scF$_V$ fragment, a single-chain antibody, a single-domain (V$_H$ or V$_L$) antibody, a camel antibody domain, a humanized camel antibody domain, an antibody region (including one or more framework regions, one or more constant regions, one or more variable regions, one or more CDR regions), etc., or any combination thereof.

In one aspect of the invention, the antibodies or antibody fragments are expressed as a fusion protein comprising from the N-terminus to the C-terminus a leader peptide (e.g., secretory signal), a first chain or fragment of a chain and a second chain or fragment of a chain (e.g., $V_L$ and $V_H$; $V_L$-$C_L$ and $V_H$-$C_H$). In eukaryotic cells, the leader peptide directs the fusion proteins from the endoplasmic reticulum to the Golgi apparatus to the cellular membrane. In some exemplary embodiments, the V domains of the heavy and light chains can be expressed on the same polypeptide joined by a flexible linker (e.g., [Gly$_4$-Ser]$_3$ linker, SEQ ID NO: 13) to form a single chain FV fragment (scFv) (see e.g., McCafferty et al., Nature, 1990, 348: 552-554).

Scaffold Proteins

In some embodiments, the engineered protein or the protein of interest is a scaffold protein. In some embodiments, the scaffold protein can bind to an antigen. In some embodiments, the engineered protein is an antibody-mimic or antibody-like polypeptide that provides a non-antibody scaffold and one or more variable regions forming an antigen-binding site that interacts with the ligand or antigen molecule. Some of the possible advantages of non-antibody scaffold include ease of selection, expression and purification, biochemical and biological properties more specifically tailored to the physiological application and favorable pharmacokinetics. For example, a fibronectin type III domain has been used to create an antibody-like polypeptide (see for example Parker et al., Protein Engineering Design and Selection, 2005, 18(9):435-444).

In some embodiments, the scaffold protein is the human vitamin D-binding protein or a modified version of the vitamin-D binding protein. Some of the advantages of the vitamin D-binding protein are (1) its high concentration in human plasma (0.5 mg/l) which suggests that the protein is non-immunogenic; (2) its combination of high molecular weight (52 kD) and low pI (5.0) which lead to a long residence in the plasma; (3) an extensive disulfide cross-linking which provides a high thermodynamic stability; (4) the existence of a natural actin-binding site, which can be modified to accommodate other protein binding partners; and (5) the existence of a natural vitamin-D binding site which can be modified to accommodate other small molecule binding partners. The vitamin D-binding protein binding site can be engineered to generate a library of protein variants that can bind a variety of target molecules.

In another embodiment, a non-antibody scaffold protein is a Cu, Zn superoxide dismutase (SOD) or a modified version thereof. The SOD protein is an essential enzyme that protects cells from scavenging superoxide radical. The human form of the protein (HSOD) adopts a beta-barrel fold and forms an homodimer. Mutations at the two free cysteine residues C6A and C111S result in a thermostable version of the protein (HSOD-AS). The HSOD-AS variant retains the wild type-fold and activity. The advantages of the HSOD protein and the HSOD-AS variant include high stability, relatively small size (154 amino acids monomer) and human origin. In some embodiments, the enzymatic activity is removed through mutation of one or more active-site catalytic residues. In some embodiments, the designed scaffold operates as a homodimer, in some embodiments the designed scaffold is redesigned as a stable monomer. A library of variants can be generated and screened for binding to a specific target or substrate. For example, the amino acid sequence can be varied within the loop connecting the beta-sheet elements (for example, loops 23-28; 63-82, 102-114, 11-14; 37-40; 90-93; 120-123; and 141-144).

In some embodiments the scaffold protein is human serum albumin or a modified version of human serum albumin.

Expression Systems and Host Cells

In some embodiments, the engineered proteins are expressed in vitro. In vitro expression systems are known in the art and include expression using cell extracts and expression systems using a mixture of protein expression and translation enzymes.

In some embodiments, the engineered proteins are expressed in vivo. The engineered proteins of the invention can be expressed in any host cell and the invention embraces any prokaryotic or eukaryotic cell, including bacterial cells, yeast cells (e.g., *Saccharomyces* and/or *Picchia* species), insect cells, *Xenopus* cells, and mammalian cells. Cells that are particularly suited for expression of the fusion proteins of the invention are *E. Coli.*, *S. cerevisiae*, CHO and 293T cells. The cells may be 'wild type' cells or the cells may be optimized for a particular characteristic or for a particular enzyme function that may aid in protein expression. These cells include cells that have an optimized capability to take up and maintain nucleic acids, cells that have increased protein synthesis capability and/or cells that have increased protein secretion capability. Cells that can maintain the integrity of the nucleic acid and the synthesized proteins are particularly embraced, including cells with increased DNA repair capacity, decreased recombination capacity, increased protein folding capacity and/or decreased protein degradation (e.g., protease) capacity.

In some embodiments, cells may be selected or engineered to have one or more protease deficiencies (e.g., they lack one or more protease enzymes and/or they lack one or more protease targeting proteins) so that expressed proteins of interest are not degraded.

In some aspects, cells for bacterial or yeast display may be used. In some embodiments, cell display systems feature transfection of cells with DNA libraries and expression of library encoded polypeptides or proteins as fusions with extra-cellular receptors. Bacterial cells, yeast cells and mammalian cells can all be used for cell surface display.

It should be appreciated that any of these cellular expression and/or secretion and/or immobilization techniques may be used in combination with display techniques of the invention.

Bacterial Fusion Proteins

In one aspect, the invention provides methods for the immobilization of one or more engineered proteins, binding partners, molecular targets, substrates, etc., or any combination thereof, on a cell surface by providing fusion proteins for display on a cell surface.

In one aspect, the invention provides methods for the immobilization of one or more engineered proteins, binding partners, molecular targets, substrates, etc., or any combination thereof, on a cell surface by providing fusion proteins for display on a bacterial cell surface. In some embodiments, the bacterial fusion proteins are based on bacterial surface proteins, which may be used for display of one or more engineered proteins, binding partners, molecular targets, substrates, etc., or any combination thereof, on bacteria. In bacterial cell display, foreign gene products have been fused to surface-accessible regions of proteins and outer membrane proteins such as OmpA, OmpC, PhoE, LamB, FhuA, and BtuB (Lang, Int. J. Med. Microbiol. 2000, 290: 579-585; Etz et al., J. Bacteriol 2001, 183: 6924-6935). Insertions of polypeptides of more than 100 amino acids residues can be tolerated in certain cases.

Another class of bacterial surface proteins for display are transporter proteins, which contain the translocator domain mediating the outer membrane trafficking of a passenger protein. Replacement of the neutral passenger domain of these transporters with an alternative polypeptide (e.g., one or more engineered proteins, binding partners, molecular targets, substrates, etc., or any combination thereof) leads to the display of this polypeptide on the bacterial surface in the translocator domain. A related method for displaying proteins on the surface of bacteria is through the use of lipoproteins, like TraT, and peptidoglycan-associated lipoproteins (PAL), which through their C-terminus are covalently attached to the peptidoglycan layer, but have a free N-terminus for the fusion of a polypeptide of interest (Dhillon et al., Lett. Appl. Microbiology (1999); 28: 350-354).

In one aspect, the invention provides methods for novel fusion proteins for bacterial surface display. A list of bacterial fusion anchoring motifs for display of proteins of interest is provided in Table 1. The anchoring motifs of Table 1 are selected based on their ability to present polypeptides of interest on the bacterial cell wall.

TABLE 1

Fusion partners for bacterial surface display

| Fusion partner | Protein characteristics |
|---|---|
| tolC, Q, R, A | Membrane spanning complex |
| OmpW | Outer membrane protein, |
| tonB, ExbB, ExbD | Membrane spanning complex |
| nfrA | Phage receptor, outer membrane subunit |
| csgG | Outer membrane lipoprotein |
| slyB | Outer membrane lipoprotein |
| yfiO | Outer membrane lipoprotein |
| Slp | Outer membrane lipoprotein |
| Blc | Outer membrane lipoprotein |
| Hyf (B, C, D, E, F) | Hydrogenase subunit |
| Frd (D, C) | Fumarate reductase, membrane anchor subunit |
| osmC | Osmotically inducible membrane protein |
| ynfH | Oxidoreductase, membrane subunit |
| glpB | Dehydrogenase, membrane anchor subunit |
| Nuo (N, M, L, K, J, H, A) | NADH::ubiquinone oxidoreductase |
| hokC | Toxic membrane protein |
| OmpX permutant | |

Yeast Surface Display

In one aspect, the invention provides methods for the immobilization of one or more engineered proteins, binding partners, molecular targets, substrates, etc., or any combination thereof, on a cell surface by providing fusion proteins for display of one or more engineered proteins, binding partners, molecular targets, substrates, etc., or any combination thereof, on a yeast cell surface. In one embodiment, the invention provides for methods for displaying a first binding partner on a cell surface by expressing a cell surface protein coupled with a second binding partner and binding a first binding partner to the second binding partner. A commonly used organism for protein display is yeast. Yeast display offers the advantage over bacteria-based technologies in that yeast can process proteins that require endoplasmatic reticulum (ER)-specific post-translational processing for efficient folding and activity. While mammalian cell display also facilitates post-translational processing, yeast offers the advantage of ease of generation of nucleic acid libraries, because the vectors can be simpler, and an easier introduction of the libraries into the host cells. Most yeast expression fusion proteins are based on GPI (Glycosyl-Phosphatidyl-Inositol) anchor proteins which play important roles in the surface expression of cell-surface proteins and are essential for the viability of the yeast. One such protein, alpha-agglutinin consists of a core subunit encoded by AGA1 and is linked through disulfide bridges to a small binding subunit encoded by AGA2. Proteins encoded by the nucleic acid library can be introduced on the N-terminal region of AGA1 or on the C terminal or N-terminal region of AGA2. Both fusion patterns will result in the display of the polypeptide on the yeast cell surface.

In some embodiments, fusion proteins for yeast display include an engineered protein fused to the N-terminal or C-terminal part of a protein capable of anchoring in a eukaryotic cell wall (e.g., α-agglutinin, AGA1, Flo1 or major cell wall protein of lower eukaryotes, see U.S. Pat. Nos. 6,027,910 and 6,114,147 which are hereby incorporated by reference), for example, proteins fused with the GPI fragment of Flo1 or to the Flo1 functional domain (Kondo et al., Appl. MicroBiol. Biotechn., 2004, 64: 28-40).

In addition to surface display methods based on established fusion proteins comprising a GPI anchor motif, the invention also embraces display methods based on novel fusion proteins comprising a modified GPI anchor motif. Fusion proteins of the invention may comprise a protein to be displayed (e.g., one or more engineered proteins, binding partners, molecular targets, substrates, etc., or any combination thereof), a GPI anchor and appropriate signaling sequences, which may be post-translationally modified when the fusion protein is expressed in yeast. As a protein containing the GPI anchor and C-terminal signaling sequence is trafficked through the ER, a hydrophobic region on the C-terminal signal sequence adjacent to the GPI anchor becomes embedded in the ER membrane, where it is cleaved by an ER protease. As the ER protease cleaves this C-terminal signal sequence, it simultaneously attaches a preformed GPI anchor to the new C-terminus of the engineered protein (e.g., binding partner, molecular target, substrate, etc., or any combination thereof) ultimately resulting in the display of the protein (e.g., binding partner, molecular target, substrate, etc., or any combination thereof) on the cell surface (See, e.g., Kondo et al. Appl. MicroBiol. Biotechn. 2004, 64: 28-40). The invention embraces C-terminal sequences with improved processing properties resulting in the improved display of fusion proteins comprising the GPI-anchor proteins. Improved display comprises an increase in the number of displayed proteins and/or an increase in the number of correctly expressed proteins. In some embodiments, C-terminal sequences with improved processing properties are evolved by screening libraries containing variant C-terminal sequences according to techniques known in the art.

In one aspect, the invention provides methods for the display of engineered proteins (one or more engineered proteins, binding partners, molecular targets, substrates, etc., or any combination thereof) comprising a fusion protein comprising a yeast display anchoring motif, wherein the anchoring motif does not comprise a GPI anchor. A yeast anchoring motif may be a cell surface protein that is partially exposed to the extracellular environment at one of its termini, and may have a high copy number. A protein of interest (e.g., an engineered protein, binding partner, molecular target, substrate, etc., or any combination thereof) to be immobilized may be fused to the exposed terminus. Proteins of interest to be displayed can be fused both through their N- or C-terminus to the display fusion partner. Anchoring motifs can be expressed with their own secretory leader sequence, or anchoring motifs can be outfitted with leader sequences that result in improved expression and/or secretion. A non-limiting overview of yeast anchoring motifs is presented in Table 2.

TABLE 2

Anchoring motifs for yeast display proteins

| Protein | Size (kDa) | Copy number* | Protein characteristics |
|---|---|---|---|
| CCW14 | 23.3 | 42,000 | Covalently linked cell wall protein, inner layer of cell wall |
| CIS3 | 23.2 | 12,500 | Mannoprotein, internal repeat protein |
| CWP1 | 24 | 2,060 | Mannoprotein linked through phosphodiester bond to beta-1,3- and beta 1,6-glucan |
| PIR1 | 34.6 | 1,170 | Required for cell wall stability, mediates mitochondrial translocation of Apn1, expression regulated by cell integrity pathway |
| PIR3 | 33 | | Required for cell wall stability, expression is cell cycle regulated |
| SAG1 | 70 | | Alpha-agglutinin of alpha-cells, binds to Aga1p during agglutination, N-terminal half is homologous to the immunoglobulin superfamily and contains binding site for a-agglutinin, C-terminal half is highly glycosylated and or contains GPI anchor |
| CWP2 | 9 | 1590000 | Covalently linked cell wall mannoprotein, major constituent of the cell wall; plays a role in stabilizing the cell wall; involved in low pH resistance; precursor is GPI-anchored |
| STE2 | 48 | | Receptor for alpha-factor pheromone; seven transmembrane-domains |
| STE3 | 53 | | Receptor for a-type mating factor |

*Copy Number based on Ghaemmaghami S, et al. (2003) Global analysis of protein expression in yeast. *Nature* 425(6959): 737-41

In some embodiments, the yeast fusion proteins used for display include a cell-surface display system based on fusing an engineered protein to be displayed to the flocculation domain of a GPI anchor protein without the C-terminal portion of the GPI anchor protein (e.g., Flo1, Flo2, Flo3, Flo4, Flo5, Flo9, Flo10 or Flo11 as described in U.S. Pat. No. 7,192,764 which is hereby incorporated by reference). The sugar chains of the flocculation domain bind to the sugar chains of the cell wall, thereby displaying the engineered protein (e.g., an engineered protein, binding partner, molecular target, substrate, etc., or any combination thereof) on the cell surface.

Carbohydrate Binding

One aspect of the invention embraces non-covalent attachment of an engineered protein (e.g., an engineered protein, binding partner, molecular target, substrate, etc., or any combination thereof) to one or more components of the cell surface. In some embodiments, the cell surface is the yeast cell wall. In some embodiments, the engineered protein comprises a protein of interest (e.g., an engineered protein, binding partner, molecular target, substrate, etc., or any combination thereof) fused to a peptide comprising a carbohydrate binding domain. In some embodiments, the secreted protein is attached non-covalently to the carbohydrates present at the cell surface. In some embodiments, the secreted protein is attached non-covalently to surface proteins on the cell surface. In some embodiments, a carbohydrate binding domain of the fusion protein may interact intracellularly with cell wall components being exported at the cell surface. In some embodiments, the carbohydrate binding domains are fused with the C-terminus of the protein of interest or to the N-terminus of the protein of interest or both to the C- and the N-terminus of the protein of interest (e.g., an engineered protein, binding partner, molecular target, substrate, etc., or any combination thereof). In some embodiments, the engineered protein comprises multiple carbohydrate binding domains. One skilled in the art would recognize that any carbohydrate or molecule present at the surface of the cell can be used to attach and immobilize the fusion protein at the cell surface. However, it is preferable to attach the fusion protein (e.g., an engineered protein, binding partner, molecular target, substrate, etc., or any combination thereof) to molecules present in high copy number at the cell surface (e.g., at least 100, 1,000, 10,000 copies). Carbohydrates are a major component of the yeast cell surface. Surface carbohydrates include mannoproteins, 1,3-β-glucans, 1,6-β-glucan and chitins. Mannoproteins form 30 to 50% of the cell wall mass, where proteins account for only 4-5% of the mass and protein-linked mannose containing carbohydrate side chains account for the remaining mass. 1,3-β-glucans compose 30-45% of the cell wall mass, forming a continuous network stabilized by inter-chain hydrogen bonding. 1,6-β-glucans compose 5-10% of the cell wall mass, forming a network with other cell wall proteins or carbohydrates. Chitin composed 1.5 to 6% of the cell wall mass, being mostly present on the intracellular side of the cell wall. Any domain known to those skilled in the art to bind molecules of the carbohydrate family may be fused to a protein to be immobilized at the cell surface. For example lectins are known carbohydrate-binding proteins or glycoproteins which are highly specific for their sugar moieties. Examples of lectins comprise concanavalin A (ConA) which binds internal and non-reducing terminal alpha-mannosyl groups, phytohemagglutinin (PHA) which consists of two closely related proteins PHA-L and PHA-E and mannose-binding lectin (MBL). Additional classes of carbohydrate binding domains are the carbohydrate binding modules (CBM). These modules were originally classified as cellulose binding domains (CBDs), but binding to carbohydrates other than cellulose has been found. CBMs are naturally found appended to catalytic modules, promoting the association of the catalytic domain of the enzyme with its substrate. Examples include:

| Family | Protein | PDB code |
|---|---|---|
| CBM4 | Laminarinase 16A (*Thermotoga maritima*) | 1GUI |
| CBM6 | Xylanase 11A (*Clostridium thermocellum*) | 1UXX |
| CBM9 | Xylanase 10A (*Thermotoga maritima*) | 1I8A |
| CBM13 | Xylanase 10A (*Streptomyces olivaceoviridis*) | 1XYF |
| CBM15 | Xylanase 10C (*Cellvibrio japonicus*) | 1GNY |
| CBM17 | Cellulase 5A (*Clostridium cellulovorans*) | 1J83 |
| CBM18 | Agglutinin (*Triticum aestivum*) | 1WGC |
| CBM20 | Glucoamylase (*Aspergillus niger*) | 1AC0 |
| CBM27 | Mannanase 5A (*Thermotoga maritima*) | 1OF4 |
| CBM29 | Non-catalytic protein 1 (*Pyromyces equi*) | 1GWK |
| CBM32 | Sialidase 33A (*Micromonospora viridifaciens*) | 1EUU |
| CBM34 | α-Amylase 13A (*Thermoactinomyces vulgaris*) | 1UH2 |
| CBM36 | Xylanase 43A (*Paenibacillus polymyxa*) | 1UX7 |

There are more than 300 putative CBM sequences in more than 50 different species, classified into 43 families. CBMs exhibit a variety of interaction specificities, with different CBMs known to bind cellulose, chitin, β-1,3-glucans and β-1,3-1,4-mixed linkage glucans, xylan, mannan, galactan and starch, or 'lectin-like' specificity with binding to a variety of cell-surface glycans. Crystal structures are available for members of at least 22 CBM families, including structures of 15 CBMs from 10 different families in complex with their oligosaccharide ligands.

Known or existing carbohydrate-binding proteins, such as those identified above, may be used directly as the carbohydrate binding domain. In some embodiments, improved carbohydrate binding domains characterized by a higher binding affinity, a more specific binding, a higher stability, an increased surface expression, and/or improved oligomeric properties are used. Further, the oligomeric structure of a known carbohydrate-binding protein may be changed. For example, a single-chain form of a higher-order oligomer may be created in order to make a single polypeptide fusion of carbohydrate binding domain and protein of interest (binding partner, molecular target etc.).

Flo1, Flo5 and Flo10 comprise three domains: a mannose-binding domain, an intermediate repeating trans cell wall domain and a C-terminal GPI anchor signal sequence and motif (Teunissen and Steensma, 1995, Yeast, Vol. 11, pp 1001-1003). It has been demonstrated that overexpression of the wild-type flocculins tends to result in an increased tendency for the cells to form flocs (Guo et al., 2001, PNAS Early Edition, (2001). However, this tendency can be somewhat mitigated by expressing a truncated version containing only the N-terminal functional domain as a fusion to a target protein as has been done in earlier attempts at FLO1-mediated display systems (Matsumoto et al., 2002, Applied and Environmental Microbiology, 68:9 4517-4522). In one aspect of the invention, the N-terminal functional domain of Flo1 or Flo1 homolog protein comprising the mannose binding domain is expressed in a yeast cell. The expressed truncated protein does not contain the GPI anchor motif nor the cell wall domain but comprises the mannose binding domain allowing it to bind mannose residues in the cell wall or on the cell surface.

In some embodiments, the carbohydrate binding domain is derived from a protein without particular carbohydrate-binding properties. For example, the carbohydrate binding domain may be derived from a general protein-binding platform such as single-chain antibodies, other antibody formats, designed ankyrin repeat proteins (DARPins), leucine-rich repeat (LRR) proteins, tetratricopeptide repeat (TPR) proteins, armadillo repeat (ARM) proteins, avimers, lipocalcins, Fn3s (including 10Fn3s, or AdNectins), linear peptides, disulfide-constrained peptides, small modular immunopharmaceuticals (SMIPs), tetranectins, T-cell receptors, PDZ domains, or A-domain proteins, etc., or any combination thereof. Further scaffolds include cytotoxic T-lymphocyte-associated antigen 4 (CTLA-4), tendamistat, neocarzinostatin, carbohydrate-binding module 4 of family 2 of xylanase from *Rhodothermus marinus* (CBM4-2), immunity protein 9 (Im9), zinc finger, protein VIII of filamentous bacteriophage (pVIII), GCN4, WW domain, src homology domain 3 (SH3) domains, src homology domain 2 (SH2) domains, TEM-1 β-lactamase, green fluorescent protein, thioredoxin, staphylococcal nuclease, plant homeodomain finger (PHD finger), chymotrypsin inhibitor 2 (C12), bovine pancreatic trypsin inhibitor (BPTI), Alzheimer's amyloid β-protein precursor inhibitor (APPI), human pancreatic secretory trypsin inhibitor (hPSTI), Ecotin, human lipoprotein-associated coagulation inhibitor domain 1 (LACI-D1), leech-derived trypsin inhibitor (LDTI), mustard trypsin inhibitor 2 (MTI II), scorpion toxins, insect defensin A, Ecballium elaterium trypsin inhibitor II (EETI II), and cellulose binding domain (CBD).

In some embodiments, the carbohydrate binding domain is composed of multiple interaction domains in order to decrease the overall dissociation rate through avidity effects or to increase the binding affinity of the fusion protein to the carbohydrates. Each domain may be identical, similar, or may have a different protein sequence. Each domain may bind the same or different carbohydrate epitopes.

Mammalian Fusion Proteins

Mammalian cells also can be used to display one or more proteins (e.g., an engineered protein, binding partner, molecular target, substrate, etc., or any combination thereof). For example, you can use a mammalian cell protein, cell membrane protein, cell membrane binding protein, or domain thereof to display an engineered protein (e.g., an engineered protein, binding partner, molecular target, substrate, etc., or any combination thereof) on the cell surface. Mammalian cell display has the advantage of expressing human proteins with correct post translational modifications such as glycosylation and phosphorylation. For instance, Chinese Hamster Ovary cell lines or derived cell lines have been successfully developed to express valuable therapeutic proteins such as antibodies, and 293T cells have been used for the expression and display of single-chain $F_v$s (Ho et al., PNAS 2006, 103: 9637-9642).

Expression

Proteins can be expressed from nucleic acids using methods known in the art. In some embodiments, protein expression is constitutive. Constitutive expression covers both expression from nucleic acids that have been integrated in the genome and expression from nucleic acids that are located on non-integrated vectors. In some embodiments, expression is initiated by an activation event. Expression can be initiated upon introduction of the nucleic acid into the cell. The invention particularly embraces embodiments where the protein is expressed upon the initiation of a signal. In some embodiments, nucleic acids that encode the engineered proteins are operably connected to an initiator sequence that regulates expression of the engineered protein. Initiator sequences that can induce expression are known in the art and include inducible promoters. In some embodiments protein expression is induced. Methods of initiating protein expression are known in the art and include the addition of an activating agent (e.g., IPTG), an increase in temperature, change in nutrient composition, change in carbon source (such as addition of sugar, methanol or glycerol), or withdrawal of an agent from the host cell environment. In some embodiments, host cells comprising the nucleic acids encoding the fusion proteins are incubated using conditions that will result in the expression of the protein. The conditions may be created when a cell is already dividing, or the conditions may already be in place when the nucleic acid is introduced in the cell or when culturing of the cell is initiated. In some embodiments protein expression is induced.

In some embodiments, protein expression occurs when the host cell comprising a nucleic acid encoding the protein is incubated and no separate induction step is required.

In some embodiments, two proteins are co-expressed by two expression constructs and secreted by the host cell simultaneously. For example, the two engineered proteins may be expressed and secreted under the same culture conditions. In some embodiments, the two proteins are expressed sequentially. If the two engineered proteins are expressed sequentially, the host cells may be co-transfected simultaneously with two expression constructs under the control of two inducible promoters (e.g., two different inducible promoters). Expression of the first protein is initiated by incubating the host cells under conditions sufficient to induce expression of the first protein and expression of the second protein is initiated under conditions sufficient to induce the expression of the second protein. Alternatively, the host cells may be transfected with a first expression vector encoding a first protein and then transfected with a second expression vector encoding a second protein. Alternatively, host cells may constitutively express the first protein and subsequently be transfected or transformed with a vector encoding a second protein.

Display of the First Binding Partner

In some embodiments, secreted engineered proteins are bound to a first binding partner through a modification of the engineered protein. In some embodiments the immobilization peptide is modified. In some embodiments, the secreted engineered proteins are bound to the first binding partner through a second binding partner attached to the engineered protein (e.g., immobilization peptide). In one embodiment, the first binding partner is a biotin binding partner and the second binding partner is biotin or biotin analog. In another embodiment, the first binding partner is an avidin or avidin-like binding peptide and the second binding partner is avidin or an avidin-like protein or variations thereof. Yet, in another embodiment, the first binding partner is a biotin or biotin analog and the second binding partner is avidin or an avidin-like protein or variations thereof. Avidin-like proteins are defined as proteins that have a strong affinity for biotin. Non-limiting examples of avidin-like proteins are avidin, streptavidin, Neutravidin and modifications thereof.

In some embodiments, the secreted engineered proteins are bound to a first binding partner, whereby the first binding partner is displayed on the cell surface. It should be appreciated that the first binding partner may be attached to cell surface either in vitro or in vivo, directly or indirectly, by a variety of methods. Suitable in vitro methods include but are not limited to direct coupling to amino groups or coupling to thiols or indirect coupling (through for example biotin or an antibody). Alternatively, the first binding partner may be expressed and secreted by the host cell. In some embodiments, the first binding partner is fused to an anchoring motif and displayed at the cell surface.

In some embodiments the first binding protein is attached to the cell surface through a set of binding partners. In some embodiment the cell surface displays a third binding partner. In some embodiments the first binding partner is linked to a fourth binding partner, which can bind to the third binding partner, thereby displaying the first binding partner on the cell surface. In some embodiments, the third and fourth binding partner relate to the display of a first binding partner, target molecule or substrate on the cell surface. It should be appreciated that the third and fourth binding partners can be the same physical entities as the first and second binding partners. For instance, in one embodiment of the invention both the first and a third binding partner are biotin, while and both the second and fourth binding partner are streptavidin. In another embodiment of the invention the first and fourth binding partner are biotin, while the second and third binding partner are avidin.

The display of biotin on the cell surface can be established for instance by biotinylation of the cell surface proteins in vitro by, for example the use of sulpho-NHS-biotin (Pierce Chemical Co.) or biotin-sulfosuccinimidyl ester (Invitrogen). However, one should appreciate that as cells divide, the daughters cells do not retain biotin. In some embodiments, biotinylation of the cell surface proteins may be accomplished in vivo. In some aspects of the invention, a biotin acceptor peptide (i.e., an immobilization peptide comprising a modification motif) may be fused to an anchoring cell surface protein or cell wall protein, in vivo biotinylated (e.g., with biotin ligase), and the fusion protein comprising the surface protein or cell wall protein and biotinylated acceptor peptide may be displayed at the cell surface of the host cell. In some embodiments, the cell surface protein may be engineered to include one or more biotin acceptor peptides. For example, the cell surface protein may be engineered to comprise an anchoring domain or motif, extracellular domains and a biotin acceptor peptide fused to extracellular domains or the cell surface protein may be engineered to include more than one biotin acceptor peptide to its extracellular terminus and to the extracellular domains. The expression of the resulting biotinylated cell surface protein may be constitutive or inducible. The cell surface protein is preferably a protein that is natively localized in the cell membrane or the cell wall. Such proteins may be chosen based, for example, on their expression levels, their size, and their structural features and any combination thereof. For instance, preferred cell surface proteins have a high native expression level. In a preferred embodiment, proteins have an extracellular N-terminus and/or C-terminus or intra-protein loops with extracellular domains that are amenable to peptide insertion or fusion allowing the second (or fourth) binding partner (e.g., biotin) to freely interact with the first (or third) binding partner at the cell surface (e.g., avidin). In yeast, the cell surface protein includes but is not limited to a natively present cell wall protein such as SAG1, HPS150 (PIR2P), CWP2, BIOS, SAG1, FLO5, FLO1, FIG1, FIG2, STE2, STE3, etc., or variants of the above proteins or any other relevant cell wall proteins.

In a preferred embodiment, the engineered cell surface protein comprising at least one biotin acceptor peptide is co-expressed with a biotin ligase, resulting in the in vivo biotinylation of the biotin acceptor peptide(s), thus displaying biotin at the host cell surface. In some embodiments, the engineered cell surface protein comprising at least one biotin acceptor peptide is co-expressed with a chaperone protein resulting in the in vivo biotinylation of the biotin acceptor peptide(s) and display of biotin at the host cell surface. Chaperone proteins are proteins that facilitate transport and/or folding of the engineered protein. Chaperone proteins are known in the art and non-limiting examples include BiP, GRP94, GRP170, clanexin, calreticulin, HSP47, HSP60, HSP70, HSP90, HSP100, ERp29, ERp57, PDI and PPI. In some embodiments, the chaperone protein is BiP.

In vivo biotinylated cells can be incubated with soluble avidin at any time point over the course of a capture assay or a screening assay. For example, free soluble avidin can be added at any time point during the assay thereby allowing daughters cells to be labeled with avidin or avidin-like protein and to capture biotinylated engineered proteins. Host cell culture conditions can be optimized so that the cells retain the avidin bound to the displayed biotin. Maintaining an optimal number of avidin on the surface of the cells displaying biotin may be achieved by, for example, incubating the cells with an increased avidin concentration (e.g., 2 mg/ml, 5 mg/ml, 10 mg/ml, etc.), lowering the cell culture temperature (for example to 20° C. for yeast); increasing the viscosity of the medium (e.g., by addition of PEG) or any combination thereof.

In yet another embodiment, cell division is inhibited to maximize the percentage of avidin-labeled cells present in the display assay. One should appreciate that if after biotinylation of the cell surface protein cell division is inhibited, the "parent" cells will not divide and no daughters cells are generated, and the majority of the cells will possess avidin on their surface (see FIG. 12). Strategies for slowing cell division include, but are not limited to, temperature change, chemical treatment, or alteration of assay time scale. Chemicals used to slow cell division include, but are not limited to, hydroxyurea, nocodozole, farnesol, a-mating factor, α-mating factor, leflunomide, calcium-deprived media, EGRA, lithium, mimosine, lovastatin, aphidicolin, and thymidine.

Biotin binding moieties (e.g., avidin and avidin-like proteins) are known in the art and include avidin and variations thereof, such as streptavidin and neutravidin. Avidin (from egg-white), streptavidin (from *Streptomyces avidinii*) and Neutravidin are related proteins that bind biotin with similar dissociation constants of about $10^{-15}$ M (Green, 1975, Adv. Protein Chem., vol. 29, pp. 85-133). NeutrAvidin protein is a deglycosylated version of avidin and binds to a lesser extent to lectins. Avidin and avidin like proteins are constructed of four non-covalently attached identical subunits, each of which bears a single biotin-binding site and exhibit the same three dimensional fold. Each protein functions as a homo-tetramer, where four identical copies of the monomer associate into the native quaternary structure, each monomer binding one molecule of biotin. Two monomers associate to form a primary or structural dimer, two of which then combine to form a tetramer (for review, see e.g., Laitinen et al., *Trends Biotech.*, Vol. 25, No 8, pp 269-277, 2007). The unique feature of the binding of avidin to biotin is the strength and specificity of formation of the avidin-biotin complex. The resultant affinity constant, estimated at $1.6\times10^{-15}$ M for avidin and $2.5\times10^{-13}$ M for streptavidin, is the highest known for a protein and an organic ligand. The strong affinity of avidin or streptavidin to biotin is dependent on the tetrameric configuration of the protein. Avidin monomer shows a highly reduced affinity constant ($10^{-7}$ M, Laitinen et al., 2003, *J. Biol. Chem. Vol.* 278, pp 4010-4014). In some embodiments, avidin is expressed by the cell together with the engineered protein to be displayed. Recombinant forms of avidin and streptavidin have been engineered and produced in eukaryotic and prokaryotic expression systems with modified properties of charge, oligomerization and ligand specificity.

It should be appreciated that the methods described herein may be implemented with any avidin, avidin-variant or avidin-like protein described herein.

Oligomeric proteins have been successfully displayed at the cell surface by expressing one subunit fused with an anchoring motif and secreting the remaining subunits. For example, hetero-oligomeric functional antibody's Fab fragment has been successfully displayed on the yeast cell surface by expressing the light chain Fab fragment as a fusion Fab-α-agglutinin protein and a fragment of the Fab heavy chain as a secretion protein (Lin Y. et al., 2003, Appl. Microbiol. Biotechnol., Vol. 62, pp 226-236). Moreover, Furukawa et al., were able to display streptavidin on a yeast cell surface by co-expressing native subunits and anchored subunits fused with the C-terminus of 318 amino acids of Flo1p (2006, Biotechnol. Prog., Vol. 22, pp 994-997). In some embodiments, an avidin monomer fused with an anchoring motif is displayed on the cell-surface. In some embodiments, additional copies of avidin are expressed and secreted by the host-cell. In some embodiments, the displayed avidin monomer fused with an anchoring motif binds to additional avidin proteins secreted by the host cell.

It should be appreciated that avidin and avidin-like proteins can also be expressed as two polypeptide dimer chains (Nordlund et al., 2004, J. Biol. Chem., Vol. 279, pp 36715-36719 and WO05047317) or as a single tetrameric polypeptide chain (Nordlund et al., Biochem. J., 2005, Vol. 392, pp 485-491). In one embodiment, avidin or avidin-like protein is expressed as two single chain avidin dimers wherein one single chain dimer is expressed as a protein fused to an anchoring motif and the second single chain dimer is expressed and secreted by the host cell. In another embodiment, avidin or avidin-like proteins are expressed and secreted as single chain tetramers fused to an anchoring motif. In yet other embodiments, the different subunits of the avidin or avidin like protein are co-expressed and secreted as a single-chain dimeric avidin, a monomeric avidin and a monomeric avidin subunit fused to anchoring motif. In another embodiment, avidin is displayed at the surface of the host cell as a fusion of a monomeric or dimeric avidin-anchoring motif protein. Anchoring motifs include, but are not limited to, any known cell wall proteins (e.g., α-agglutinin, Flo1p), GPI anchors, modified GPI anchors, AGA2, etc., or any other anchoring motif described herein or known to one of skill in the art. Engineered tetrameric, dimeric, and monomeric avidin may be design to bind biotin with an affinity represented by a dissociation constant of about $10^{-7}$ M, about $10^{-8}$ M, about $10^{-9}$ M, about $10^{-10}$ M, about $10^{-11}$ M, about $10^{-12}$ M, about $10^{-13}$ M, about $10^{-14}$ M or about $10^{-15}$ M.

Figure 2:
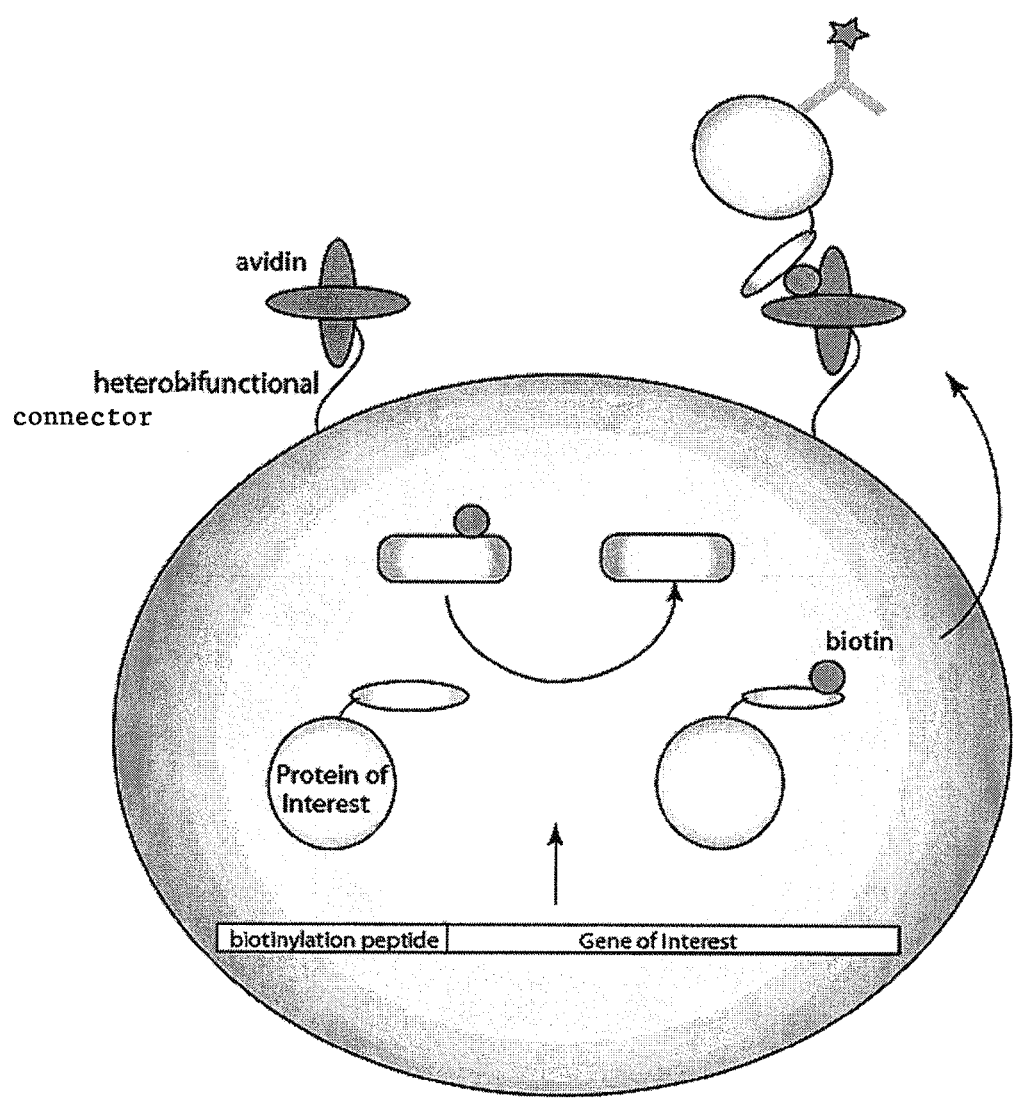
FIG. 2 illustrates a non-limiting overview of the expression of an engineered protein comprising a protein of interest linked to a biotinylation peptide (a second binding partner) wherein avidin (the first binding partner) is linked to the cell surface directly.

In some embodiments, a first binding partner such as avidin, streptavidin or avidin-like protein is conjugated (also referred to as connected) to cell surface directly (See FIG. 2). The first binding partner can be covalently bound to the cell surface or the first binding partner can be bound to the cell surface through other binding interactions, including binding interactions based on affinity. The covalent conjugation of the first binding partner to the cell surface can be accomplished using a variety of connectors. A connector is any molecule that can covalently conjugate the binding moiety to the cell surface. In some embodiments, a heterobifunctional connector is used. Non-limiting examples of heterobifunctional connectors are C6-succinimidyl 4-hydrazinonicotinate acetone hydrazone (C6-SANH), succinimidyl 4-hydrazinonicotinate acetone hydrazone (SANH), succinimidyl 4-hydrazidoterephthalate hydrochloride (SHTH), succinimidyl 4-formylbenzoate (SFB) and C6-succinimidyl 4-formylbenzoate (C6-SFB). In some embodiments, the connector comprises N-hydroxysuccinimide (NHS; which can react with free amines) and aldehyde-reactive hydrazide functional groups. Non-limiting examples of connectors comprising NHS and hydrazide groups are C6-SANH and SANH.

A non-limiting example of a hetero-bifunctional connector that can be used to conjugate a first binding partner comprising free amines, like avidin, or a carbohydrate containing binding partner, to the cell surface, is C6-succinimidyl 4-hydrazinonicotinate acetone hydrazone (C6-SANH). The first binding partner can be conjugated to the cell surface by labeling the binding partner with C6-SANH. This conjugation occurs by reacting the NHS groups with free amines on the surface of the first binding partner (if the binding moiety is a polypeptide, solvent exposed lysines may provide the free amines). In a subsequent step, the hydrazide moiety may be reacted with the free aldehydes on the cell surface, thereby covalently conjugating the first binding partner to the cell surface. In some embodiments, the cells are pre-treated with periodate to generate free aldehydes on the carbohydrates of the cell surface. Alternatively, if the first binding partner comprises a carbohydrate group, the conjugation can be performed by reacting the cells with C6-SANH to form covalent bonds between free amines on the cell surfaces and the NHS ester moiety of the connector. The cells can then be mixed with periodate-treated binding moiety using the connector's free hydrazide group to create a stable connection between oxidized carbohydrate on the first binding partner and the cell surface. However, it should be appreciated that any other suitable technique may be used to connect the first binding partner to the cell surface as the invention is not limited in this respect.

In some embodiments, a binding partner is connected to the cell surface through a spacer. In some embodiments, the first binding partner is connected to the cell surface through a spacer. The first binding partner can be covalently bound to the spacer or the first binding partner can be bound to the spacer through other binding interactions, including binding interactions based on affinity. In some embodiments, the spacer comprises a biotin moiety and is referred to as a biotin spacer. In some embodiments, the first binding partner is a biotin binding moiety, such as avidin, and the spacer comprises biotin and a linker element. In some embodiments, the linker is attached to the cell surface. In some embodiments a spacer comprises a set of binding proteins. In some embodiments the first binding partner is bound to a fourth binding partner, which is connected to a third binding partner, which is attached to the cell surface.

Spacers are not limited to interactions between binding partners and the invention embraces any moieties that can function as a spacer between the cell wall and the first binding partner. In some embodiments, spacers, including the biotin spacer, can be of any length and comprise any kind of linker, including, alkanes, PEG, etc., or any combination thereof. In some embodiments the linker is attached to the cell surface, through the action of cell wall binding protein. Preferably the spacer is chemically inert and does not react with any other component of the host cell, engineered protein or agent of the cellular environment of the host cell. Molecules that are suitable for linkers in spacers are known in the art. A spacer may be connected to the cell surface and the invention embraces the linking of the spacer to any cell surface moiety, including sugars, amino acids and lipids. In some embodiments, the spacer is linked to an amino acid side chain (e.g., through the action of an N-succimidyl ester).

In some embodiments, the secreted engineered protein and the spacer are bound to the same biotin binding moiety. In some embodiments, the secreted engineered protein is bound through its biotin to avidin, and the avidin is also bound to the biotin moiety of the biotin spacer, thereby immobilizing the engineered protein to the cell surface. In some embodiments, more than one engineered protein is bound to one avidin.

Modification Motif

In some embodiments the coupling of the second binding partner to the modification motif comprises an amino acid modification. In some embodiments, "an amino acid modification" comprises the result of any modifying event that results in the modification of the amino acid, including modifications of the peptide backbone and modifications of the amino acid side chain. In some embodiments, the amino acid side chain is oxidized, reduced or cross-linked. In some embodiments, an agent is coupled to the amino acid. In some embodiments, modification of an amino acid comprises coupling of a second binding partner. In some embodiments, the second binding partner is coupled to the amino acid modification motif by a coupling enzyme. In some embodiments, the modification is produced intracellularly. For example, the amino acid modification may be a post-translational modification of the engineered protein. Aspects of the invention also incorporate secondary modification, for example, modification of a first amino acid or amino acid sequence which in turn induces modification of a second amino acid or amino acid sequence of the fusion protein.

In some embodiments, a modification motif is a sequence of amino acids that directs a certain modification event. In some embodiments, a modification motif is a sequence of amino acids that acts as a substrate for a certain modification event. Modification motifs also may be sequences that can undergo a chemical reaction, for instance, the sequence may comprise one or more cysteines, which can form di-sulfur bridges, one or more aromatic rings, which can form cross-links, or one or more side chains that can participate in chemical reactions. In some embodiments, the sequence can function as a substrate for an enzymatic modification event. Non-limiting examples of enzymatic modification events are phosphorylation, glycosylation, ubiquitination, acetylation, or other side-chain modifying event. Enzymatic modifications also may be the coupling of peptides, proteins or other biomolecules like cholesterol, and coenzymes like biotin, or other biomolecules.

Coupling of the second binding partner also may involve the addition of non-biomolecules (e.g., molecules that are not naturally present in the cell). The invention embraces both one-step and multi-step modifications. In some embodiments, a first modification is produced, which can undergo a second modification, resulting ion the coupling of the second binding partner. In some embodiments, the second binding partner is coupled extracellularly.

It should be appreciated that the modification motif may be created by mutation a protein of interest, or fusing a peptide sequence that includes a modification motif to the protein of interest.

In Vivo Biotinylation

In some embodiments, the modification motif may be a sequence that undergoes coupling of a second binding partner. In a preferred embodiment, the modification motif is a biotin acceptor peptide and the binding partner is biotin. One should appreciate that modification can be produced intracellularly or extracellularly. For example, an engineered protein comprising a biotin acceptor peptide may be expressed in a host cell and secreted at the host cell surface at its cell surface. Biotin may then be supplied extracellularly in the culture medium.

In one aspect the invention provides methods for the in vivo biotinylation of engineered proteins. Biotin is an essential coenzyme synthesized by plants, most bacteria and some fungi. Biotin is biologically active only when protein-bound and intracellular biotin is covalently attached to a class of metabolic enzymes, the biotin carboxylases and decarboxylases. These enzymes catalyze the transfer of $CO_2$ to and between metabolites, by use of the biotin cofactor as a mobile carboxyl carrier, and are key enzymes of gluconeogenesis, lipogenesis, amino acid degradation and energy transduction. Biotin protein ligase (BPL) is an enzyme responsible for attaching biotin to biotin carboxylases and decarboxylases. BPL catalyses the post-translational formation of an amide-linkage between the carboxyl group of biotin and the $\epsilon$-amino group of a specific lysine residue of the carboxylase and decarboxylase (Chapman-Smith et al., Biomol. Engineering, 1999, 16: 119-125). The invention covers any enzyme that catalyzes coupling of biotin to a protein or polypeptide. In some embodiments, the coupling enzyme is a biotin protein ligase (BPL). In some embodiments, the BPL is BirA (the *E. Coli* BPL). Bir A polypeptides and nucleic acids encoding BirA are described in U.S. Pat. No. 6,255,075 and U.S. Pat. No. 5,723,584 which are hereby incorporated by reference. A humanized version of BirA is also known in the art (J. Biotechnol. 2005, 0: 245-249). Sequences of BirA and BPL proteins are shown in Table 3. However, all BPLs are covered by the invention including BPL from *S. cerevisiae* (Cronan et al. FEMS Kett 1995, 130: 221) and human BPL (Suzuki et al. Nat. Genetics 1994, 8: 122-128). The invention covers the use of any BPL, including modified and mutated forms of BPL, in any host cell (e.g., the use of *E. Coli* BPL (BirA) in *S. cerevisiae*). In some embodiments, BPL is a temperature sensitive BPL, which can be activated by lowering or increasing the temperature to a specific level. BPL requires both ATP and biotin to couple biotin to a polypeptide. In some embodiments, host cells are grown under conditions sufficient for coupling biotin to a polypeptide. In some embodiments, the conditions are a high enough concentration of ATP and a high enough concentration of biotin. In some embodiments, ATP and/or biotin are added to the host cell environment to initiate or accelerate coupling of biotin to a polypeptide. Each BPL has a natural polypeptide substrate sequence to which biotin is coupled (the biotinylation sequence) and the invention embraces using biotinylation sequences from any BPL, synthetic biotinylation sequences or any combination thereof. Examples of BPL substrate sequences can be found in Chapman et al. (Biomol. Engineering, 1999, 16: 119-125). Examples of commercially available BPL substrate peptides are the Bioease™Tag of Invitrogen, which comprises a 72 amino acid peptide derived from *Klebsiella pneumoniae*, AviTag™ of Avidity™, which comprises a peptide of 15 amino acids and PinPoint™ of Promega which comprises a 128 amino acid peptide. Biotinylation sequences are also described in U.S. Pat. No. 5,723,584, U.S. Pat. No. 5,252,466, U.S. Pat. No. 5,874,239, U.S. Pat. No. 6,265,552 which are hereby incorporated by reference. Cell that overexpress BirA and plasmids coding for BirA are commercially available from Avidity (Denver, Colo.) and include *E. Coli* strains AVB 99, AVB 100 and AVB 101. In some embodiments, the modification motif comprises a biotinylation sequence. A peptide comprising a biotinylation motif is also referred to as a biotinylation peptide or a biotin acceptor peptide. In some embodiments, the modification motif comprises a biotinylation peptide and the amino acid modification comprises coupling biotin to the biotinylation peptide.

In some embodiments, the coupling enzyme is expressed simultaneously with the engineered protein. In some embodiments, the coupling enzyme is expressed from a vector. In some embodiments, the gene coding for the coupling enzyme is integrated into the genome of the host cell. In some embodiments, the gene for the coupling enzyme is located on the same vector as the gene for the engineered protein.

It should be appreciated that the biotinylation methods may be used to biotinylate any protein of interest or cell bound protein described herein.

TABLE 3

Sequences of BirA and BPL proteins

SEQ ID NO: 1 E. coli BirAWT
MKDNTVPLKLIALLANGEFHSGEQLGETLGMSRAAINKHIQTLRDWGV
DVFTVPGKGYSLPEPIQLLNAKQILGQLDGGSVAVLPVIDSTNQYLLD
RIGELKSGDACIAEYQQAGRGRRGRKWFSPFGANLYLSMFWRLEQGPA
AAIGLSLVIGIVMAEVLRKLGADKVRVKWPNDLYLQDRKLAGILVELT
GKTGDAAQIVIGAGINMAMRQVEESVVNQGWITLQEAGINLDRNTLAA
MLIRELRAALELFEQEGLAPYLSRWEKLDNFINRPVKLIIGDKEIFGI
SRGIDKQGALLLEQDGIIKPWMGGEISLRSAEK SEQ ID NO: 2 BirAv1
MKDNTVPLKLIALLANGEFHSGEQLGETLGMSRAAINKHIQTLRDWGV
DVFTVPGKGYSLPEPIQLLNAKQILGQLDGGSVAVLPVIDSTNQYLLD
RIGELKSGDACIAEYQQAGRGRRGRKWFSPFGANLYLSMFWRLEQGPA
AAIGLSLVIGIVMAEVLRKLGADKVRVKWPNDLYLQDRKLAGILVELT
GKTGDAAQIVIGAGINMAMRQVEESVVNQGWITLQEAGINLDRNTLAA TABLE 3-continued Sequences of BirA and BPL proteins MLIRELRAALELFEQEGLAPYLSRWEKLDNFINRPVKLIIGDKEIFGI
SRGIDKQGALLLEQDGIIKPWMGGEISLRSAEK SEQ ID NO: 3 BirAv2
MKDNTVPLKLIALLANGEFHSGEQLGETLGMSRAAINKHIQTLRDWGV
DVFTVPGKGYSLPEPIQLLNAKQILGQLDGGSVAVLPVIDSTNQYLLD
RIGELKSGDACIAEYQQAGRGRQGRKWFSPFGANLYLSMFWRLEQGPA
AAIGLSLVIGIVMAEVLRKLGADKVRVKWPNDLYLQDRKLAGILVELT
GKTGDAAQIVIGAGINMAMRQVEESVVNQGWITLQEAGINLDRNTLAA
MLIRELRAALELFEQEGLAPYLSRWEKLDNFINRPVKLIIGDKEIFGI
SRGIDKQGALLLEQDGIIKPWMGGEISLRSAEK SEQ ID NO: 4 E. coli BirAWTS
MKDNTVPLKLIALLANGEFHSGEQLGETLGMSRAAINKHIQTLRDWGV
DVFTVPGKGYSLPEPIQLLNAKQILGQLDGGSVAVLPVIDSTNQYLLD
RIGELKSGDASIAEYQQAGRGRRGRKWFSPFGANLYLSMFWRLEQGPA
AAIGLSLVIGIVMAEVLRKLGADKVRVKWPNDLYLQDRKLAGILVELT
GKTGDAAQIVIGAGINMAMRRVEESVVNQGWITLQEAGINLDRNTLAA
MLIRELRAALELFEQEGLAPYLSRWEKLDNFINRPVKLIIGDKEIFGI
SRGIDKQGALLLEQDGIIKPWMGGEISLRSAEK SEQ ID NO: 5 BirAv1S
MKDNTVPLKLIALLANGEFHSGEQLGETLGMSRAAINKHIQTLRDWGV
DVFTVPGKGYSLPEPIQLLNAKQILGQLDGGSVAVLPVIDSTNQYLLD
RIGELKSGDASIAEYQQAGRGRRGRKWFSPFGANLYLSMFWRLEQGPA
AAIGLSLVIGIVMAEVLRKLGADKVRVKWPNDLYLQDRKLAGILVELT
GKTGDAAQIVIGAGINMAMRQVEESVVNQGWITLQEAGINLDRNTLAA
MLIRELRAALELFEQEGLAPYLSRWEKLDNFINRPVKLIIGDKEIFGI
SRGIDKQGALLLEQDGIIKPWMGGEISLRSAEK SEQ ID NO: 6 BirAv2S
MKDNTVPLKLIALLANGEFHSGEQLGETLGMSRAAINKHIQTLRDWGV
DVFTVPGKGYSLPEPIQLLNAKQILGQLDGGSVAVLPVIDSTNQYLLD
RIGELKSGDASIAEYQQAGRGRQGRKWFSPFGANLYLSMFWRLEQGPA
AAIGLSLVIGIVMAEVLRKLGADKVRVKWPNDLYLQDRKLAGILVELT
GKTGDAAQIVIGAGINMAMRQVEESVVNQGWITLQEAGINLDRNTLAA
MLIRELRAALELFEQEGLAPYLSRWEKLDNFINRPVKLIIGDKEIFGI
SRGIDKQGALLLEQDGIIKPWMGGEISLRSAEK SEQ ID NO: 7 S. cerevisiae BPL1 WT
MNVLVYNGPGTTPGSVKHAVESLRDFLEPYYAVSTVNVKVLQTEPWM
SKTSAVVFPGGADLPYVQACQPIISRLKHFVSKQGGVFIGFCAGGYF
GTSRVEFAQGDPTMEVSGSRDLRFFPGTSRGPAYNGFQYNSEAGARA
VKLNLPDGSQFSTYFNGGAVFVDADKFDNVEILATYAEHPDVPSSDS
GKGQSENPAAVVLCTVGRGKVLLTGPHPEFNVRFMRKSTDKHFLETV
VENLKAQEIMRLKFMRTVLTKTGLNCNNDFNYVRAPNLTPLFMASAP
NKRNYLQEMENNLAHHGMHANNVELCSELNAETDSFQFYRGYRASYD
AASSSLLHKEPDEVPKTVIFPGVDEDIPPFQYTPNFDMKEYFKYLNV
QNTIGSLLLYGEVVTSTSTILNNNKSLLSSIPESTLLHVGTIQVSGR
GRGGNTWINPKGVCASTAVVTMPLQSPVTNRNISVVFVQYLSMLAYC
KAILSYAPGFSDIPVRIKWPNDLYALSPTYYKRKNLKLVNTGFEHTK
LPLGDIEPAYLKISGLLVNTHFINNKYCLLLGCGINLTSDGPTTSLQ
TWIDILNEERQQLHLDLLPAIKAEKLQALYMNNLEVILKQFINYGAA
EILPSYYELWLHSNQIVTLPDHGNTQAMITGITEDYGLLIAKELVSG
SSTQFTGNVYNLQPDGNTFDIFKSLIAKKVQS SEQ ID NO: 8
S. cerevisiae BPL1 variant 1 (KR to KK)
MNVLVYNGPGTTPGSVKHAVESLRDFLEPYYAVSTVNVKVLQTEPW
MSKTSAVVFPGGADLPYVQACQPIISRLKHFVSKQGGVFIGFCAGG
YFGTSRVEFAQGDPTMEVSGSRDLRFFPGTSRGPAYNGFQYNSEAG
ARAVKLNLPDGSQFSTYFNGGAVFVDADKFDNVEILATYAEHPDVP
SSDSGKGQSENPAAVVLCTVGRGKVLLTGPHPEFNVRFMRKSTDKH
FLETVVENLKAQEIMRLKFMRTVLTKTGLNCNNDFNYVRAPNLTPL
FMASAPNKKNYLQEMENNLAHHGMHANNVELCSELNAETDSFQFYR
GYRASYDAASSSLLHKEPDEVPKTVIFPGVDEDIPPFQYTPNFDMK
EYFKYLNVQNTIGSLLLYGEVVTSTSTILNNNKSLLSSIPESTLLH
VGTIQVSGRGRGGNTWINPKGVCASTAVVTMPLQSPVTNRNISVVF
VQYLSMLAYCKAILSYAPGFSDIPVRIKWPNDLYALSPTYYKKKNL
KLVNTGFEHTKLPLGDIEPAYLKISGLLVNTHFINNKYCLLLGCGI
NLTSDGPTTSLQTWIDILNEERQQLHLDLLPAIKAEKLQALYMNNL
EVILKQFINYGAAEILPSYYELWLHSNQIVTLPDHGNTQAMITGIT
EDYGLLIAKELVSGSSTQFTGNVYNLQPDGNTFDIFKSLIAKKVQS SEQ ID NO: 9
S. cerevisiae BPL1 variant 2 (KR to KK, aglyco)
MNVLVYNGPGTTPGSVKHAVESLRDFLEPYYAVSTVNVKVLQTEPW
MSKTSAVVFPGGADLPYVQACQPIISRLKHFVSKQGGVFIGFCAGG TABLE 3-continued Sequences of BirA and BPL proteins YFGTSRVEFAQGDPTMEVSGSRDLRFFPGTSRGPAYNGFQYNSEAG
ARAVKLNLPDGSQFSTYFNGGAVFVDADKFDNVEILATYAEHPDVP
SSDSGKGQSENPAAVVLCTVGRGKVLLTGPHPEFNVRFMRKSTDKH
FLETVVENLKAQEIMRLKFMRTVLTKTGLNCNNDFNYVRAPSLTPL
FMASAPNKKNYLQEMENNLAHHGMHANNVELCSELNAETDSFQFYR
GYRASYDAASSSLLHKEPDEVPKTVIFPGVDEDIPPFQYTPNFDMK
EYFKYLNVQNTIGSLLLYGEVVTSTSTILNNNKALLSSIPESTLLH
VGTIQVSGRGRGGNTWINPKGVCASTAVVTMPLQSPVTNRAISVVF
VQYLSMLAYCKAILSYAPGFSDIPVRIKWPNDLYALSPTYYKKKNL
KLVNTGFEHTKLPLGDIEPAYLKISGLLVNTHFINNKYCLLLGCGI
SLTSDGPTTSLQTWIDILNEERQQLHLDLLPAIKAEKLQALYMNNL
EVILKQFINYGAAEILPSYYELWLHSNQIVTLPDHGNTQAMITGIT
EDYGLLIAKELVSGSSTQFTGNVYNLQPDGNTFDIFKSLIAKKVQS SEQ ID NO: 10
S. cerevisiae BPL1 variant 3 (aglyco)
MNVLVYNGPGTTPGSVKHAVESLRDFLEPYYAVSTVNVKVLQTE
PWMSKTSAVVFPGGADLPYVQACQPIISRLKHFVSKQGGVFIGF
CAGGYFGTSRVEFAQGDPTMEVSGSRDLRFFPGTSRGPAYNGFQ
YNSEAGARAVKLNLPDGSQFSTYFNGGAVFVDADKFDNVEILAT
YAEHPDVPSSDSGKGQSENPAAVVLCTVGRGKVLLTGPHPEFNV
RFMRKSTDKHFLETVVENLKAQEIMRLKFMRTVLTKTGLNCNND
FNYVRAPSLTPLFMASAPNKRNYLQEMENNLAHHGMHANNVELC
SELNAETDSFQFYRGYRASYDAASSSLLHKEPDEVPKTVIFPGV
DEDIPPFQYTPNFDMKEYFKYLNVQNTIGSLLLYGEVVTSTSTI
LNNNKALLSSIPESTLLHVGTIQVSGRGRGGNTWINPKGVCAST
AVVTMPLQSPVTNRAISVVFVQYLSMLAYCKAILSYAPGFSDIP
VRIKWPNDLYALSPTYYKRKNLKLVNTGFEHTKLPLGDIEPAYL
KISGLLVNTHFINNKYCLLLGCGISLTSDGPTTSLQTWIDILNE
ERQQLHLDLLPAIKAEKLQALYMNNLEVILKQFINYGAAEILPS
YYELWLHSNQIVTLPDHGNTQAMITGITEDYGLLIAKELVSGSS
TQFTGNVYNLQPDGNTFDIFKSLIAKKVQS SEQ ID NO: 11, Streptococcus pneumonia birA
MKSYQAVYQILSKETDYISGEKIAEKLSLSRTSIWKAIKRLEQEG
IEIDSIKNRGYKLMNGDLILPEILEENLPIKVSFKPETKSTQLDA
KEAIDLGHEANTLYLASYQTAGRGRFQRSFYSPQGGIYMTLHLKP
NLPYDKLPSYTLLVAGAVYKAIKNLTLIDVDIKWVNDIYLNNHKI
GGILTEAMTSVETGLVTDIIIGVGINFTIKDFPQELKEKAASLFK
ATAPITRNELIIEIWRAFFETPAEELLYLYKKQSFILGKEVTFTL
EQKDYKGLAKDISENGKLLVQCDNGKEIWLNSGEISLNSWK Secretion In some embodiments, an engineered protein comprising a modification motif and a secretion leader peptide is secreted from the host cell. In some embodiments, cells are grown under conditions that result in secretion of the engineered fusion proteins. Secretion may occur without further induction and may be a continuous process started by the induction of expression of the protein, or secretion may be induced by changing one or more conditions in the cellular environment, independent from the induction of expression. In some embodiments, secretion of the engineered proteins is directed by a secretion peptide that is a part of the engineered protein. In addition, secretion may be facilitated by chaperone proteins (e.g., PDI, BiP etc.), that confer better folding of the engineered protein or protein complex, reduce aggregation propensity to the engineered protein (into for example non-functional structures) or confer better secretory trafficking, proteins that can transport the engineered proteins, or through proteins that can facilitate vesicle formation. In some embodiments, vectors comprising a nucleic acid encoding the chaperone proteins are transfected into the host cell under the control of the constitutive or inducible promoter. In some embodiment, the host cells are overexpressing chaperone proteins. In some embodiments, the nucleic acid encoding the chaperone proteins are integrated in the genome of the host cell. Other proteins that play a role in protein secretion may also be used (e.g., expressed along with a protein of interest). It should be appreciated that one or more chaperone proteins or other proteins may be encoded on and expressed from the genome of the host cell. In some embodiments, the host cells are optimized for secretion. For example, cell lines with increased expression of proteins that aid in secretion of the engineered proteins may be used, and host cells with optimized cell membrane characteristics, such as permeability, facilitating crossing of the membrane by the engineered proteins may be used.

In some embodiments, a first binding partner or an engineered protein comprising a first binding partner and an engineered protein comprising a second binding partner are co-expressed in a host cell and secreted by the host cell simultaneously. For example, the two engineered proteins may be expressed and secreted under the same culture conditions. If the two engineered proteins are expressed sequentially, the host cells may be co-transfected simultaneously with two expression constructs, one expression construct comprising the nucleic acid sequences encoding a first binding partner or a first engineered protein comprising a first binding partner under the control of a first constitutive or inducible promoter and a second expression construct comprising nucleic acid sequences encoding a second engineered protein comprising a second binding partner under the control of a second inducible promoter, the first binding partner being constitutively expressed or expressed after induction of the first promoter at the surface of the cell, the second binding partner being expressed and secreted by the cell after induction of the second promoter.

Alternatively, the host cells may be transfected with a vector encoding an engineered protein comprising a first binding partner under conditions such that the first binding partner is expressed at the surface of the host cells. The cultured cells may then be transfected with a vector encoding a second engineered protein comprising a second binding partner under conditions such that the second binding partner is expressed and secreted by the host cells. Alternatively, host cells may constitutively express an engineered protein comprising a first binding partner and subsequently a vector encoding the engineered protein comprising a second binding partner is introduced into the host cells.

In another aspect of the invention, the host cells may be transfected with a vector encoding an engineered cell surface protein comprising a second binding partner and incubated under conditions that the second binding partner is expressed at the surface of the host cells. The cultured cells may then be incubated with a soluble first binding partner, resulting in the display of the first binding partner. The cells may subsequently be transfected with a vector encoding an engineered protein, to which a second binding partner can be coupled in vivo or an engineered protein comprising a second binding partner under conditions such that the engineered protein comprising the second binding partner is expressed and secreted by the host cells.

In another embodiment, host cells may constitutively express the engineered cell surface protein comprising the second binding partner and/or the engineered protein of interest comprising the second binding partner. Alternatively, the host cells may express constitutively or may be induced to express a soluble first binding partner (e.g., avidin). The first binding partner may be directly or indirectly attached or coupled to the host cell surface as described above. For example, the first binding partner (e.g., avidin) may be linked to the cell surface via a second binding partner (e.g., biotin) that has been chemically coupled to the cell surface or chemically attached to the cell surface via a suitable linker. Host cells may be co-transfected or transfected subsequently with a vector encoding an engineered protein comprising a second binding partner under the control of a constitutive or inducible promoter.

It should be appreciated that the proteins described herein also may be encoded on the genome of the host cell in addition to, or instead of, the vectors.

Display of Target Molecule

In some embodiments a target molecule is expressed on the cell surface. In some embodiment an engineered protein is expressed with affinity for the target molecule. The expressed engineered protein can bind to the target molecule resulting in the display of the engineered protein.

In another aspect of the invention, host cells may be co-transfected with a vector encoding an engineered cell surface protein comprising a first binding partner and a vector encoding an engineered protein of interest having an affinity for a target molecule. The cultured cells may then be incubated under conditions that the first binding partner is expressed at the surface of the host cells. Cells displaying the first binding partner are incubated in presence of a soluble target molecule coupled with a second binding partner, wherein binding of the second binding partner to the first binding partner results in display of the target molecule at the surface. The cells may then be incubated under conditions that the engineered protein of interest is expressed and secreted by the cell and under conditions favorable for the binding of the engineered protein of interest to the target molecule displayed at the surface of the host cells. Alternatively, the host cells may constitutively express the engineered cell surface protein comprising the second binding partner and/or the engineered protein of interest.

In some embodiments a soluble second binding partner is added to cells displaying a third binding partner, resulting in binding of the second binding partner and display of the second binding partner. It should be appreciated that the third binding partner can be a moiety similar or the same as a first binding partner, and a cell displaying a third binding partner an be generated in the same way as a cell displaying a third binding partner is generated. Once a cell displaying a third binding partner is generated a soluble second binding partner can be added resulting in the display of the second binding partner. As a next step a target molecule attached to a first binding partner can be added resulting in the display of the target molecule.

In some embodiments, the first or third binding partner is avidin, neutravidin, streptavidin, avidin-like protein or any biotin-binding protein and the second binding partner is biotin or avidin-binding peptide.

In some embodiments, host cells may be transfected with a vector encoding a first binding protein (e.g., avidin), a vector encoding an engineered protein of interest having an affinity for a target molecule and a vector encoding a construct comprising a target molecule and a second binding partner. One should appreciate that in this manner all three of the principle components may be expressed, processed, and secreted in vivo. The three components may be expressed in a host cell and secreted by the host cell simultaneously or sequentially, resulting in the display of the target molecule and the binding of the engineered protein to the target molecule.

Reporter Moiety

In some embodiments, an engineered protein comprises a reporter moiety. In some embodiments, an engineered protein comprises a first reporter moiety and/or a target molecule comprises a different second reporter moiety. The reporter moiety can be N-terminally or C-terminally linked to the protein of interest of the engineered protein and/or the target molecule, or the reporter moiety can be linked to the immobilization peptide and/or the secretion peptide. The invention embraces any configuration of an operably linked engineered protein comprising an immobilization peptide (comprising the immobilization motif) and optionally a secretion peptide, and optionally a reporter moiety, or any combination thereof. In some embodiments, the reporter moiety is a fluorescent protein.

Fluorescent proteins are known in the art and include Green Fluorescent Protein (GFP) and color variants thereof like YFP (Yellow Fluorescent Protein) and DsRed. Reporter moieties also include proteins or polypeptides that can process a substrate that can readily be detected by an assay. For example, proteins in this group include peroxidases. Reporter moieties further include polypeptides that can be detected by binding the polypeptide to a labeled antibody, including the FLAG® peptide and the His6 affinity tag. The reporter moieties allow for the selection of cells that have secreted an engineered protein. In some embodiments, FACS (Fluorescence Activated Cell Sorting) can be used to identify and isolate host cells that secrete an engineered protein. However, other fluorescence based techniques may be used (e.g., a fluorescence-aware colony picker, for example available from Genetix).

Screening of Antigen or Ligand Binding Proteins

Some aspects of the invention are related to the display and screening of proteins that bind to a target protein, such as an antigen or a ligand. Some aspects of the invention are related to the display and screening of antigen binding proteins including antibodies, antibody fragments and scaffold proteins. In some embodiments, the antigen binding proteins are displayed on the host cell surface using any of the cell display methods of the invention. In some embodiments the antigen binding proteins are coupled to a second binding partner and displayed on the cell surface by binding to a first binding partner. In some embodiments, the antigen binding fragments are displayed by binding to a target molecule (e.g., an antigen) bound to the cell surface. In some embodiments, the antigen binding proteins including, antibodies, antibodies fragments, antibodies chains or scaffold proteins are expressed as fusion proteins comprising a secretion leader peptide, a biotin acceptor peptide (comprising the modifications motif) and optionally a FLAG epitope. The biotin acceptor peptide can be fused at the N-terminus of the protein and the Flag epitope can be fused to the C-terminus of the protein or the biotinylation acceptor peptide can be fused to the N-terminus of the protein and the Flag epitope to the C-terminus of the protein.

In some embodiments, genes encoding the antibody heavy and light chains are under the control of the same promoter. In some embodiments, genes encoding the antibody heavy and light chains are under the control of different promoters. For example, genes encoding the heavy and light chains may be cloned respectively under the control of GAL1 and GAL10 or GAL10 and GAL1 promoters in opposite direction for expression of the antibodies in yeast. Yeast expression vectors are known in the art and are commercially available. Exemplary vectors include the pESC vectors from Stratagene.

In one aspect, libraries of promoters are provided to optimize the ratio of light and heavy chain expression. In some embodiments, the libraries comprise mutations within the promoter's consensus sequence. In eukaryotic cells, the TATA box (or Goldberg-Hogness box) is a DNA sequence found in the promoter region of most genes. The TATA box has a core 5'-TATAAA-3' DNA sequence. Sequence analysis reveals that the nucleotide at the second position, e.g., nucleotide A, is highly conserved in yeast. In some embodiments, a mutated-TATA box library of NANNNN sequences is generated. In some embodiments, a mutated-TATA box library of NANNNN sequences is generated for each one of the promoters controlling the heavy chain and the light chain expression. As an example, when one position is conserved and five positions are non-conserved, the combinatorial library includes $10^5$ TATA box sequences for each promoter (e.g., NANNNN). In some embodiments, a library of TATA sequences is generated by random mutagenesis. In some embodiments, the library is screened to identify the TATA boxes variants having a desired property. For example, the TATA box library may be screened to identify the TATA boxes having increased antibody or antibody fragment expression over a wild type TATA box. Expression of the antibody or antibody fragment under the control of TATA box variants may be increased at least 2 times, at least 5 times, at least 10 times compared to the expression of the antibody or antibody fragment under the control of the wild type TATA box.

Screening of Host Cells

In one aspect of the invention, the host cells displaying the secreted engineered protein may be screened and selected for the expression level of the engineered protein, the stability of the engineered protein and/or the affinity to a target molecule of the engineered protein.

Some aspects of the invention relate to methods for screening for cells expressing high levels of a protein of interest. In an exemplary embodiment, in vivo or in vitro biotinylated cells are incubated with soluble avidin and under conditions to allow secretion of the biotinylated engineered protein comprising a protein of interest. Cells that display the engineered protein are detected by labeling the engineered protein. In some embodiments the cells that display the engineered protein are detected by binding to a labeled antibody against the protein of interest or using a detectable anti-class antibody. In some embodiments, the protein of interest is fused with an epitope-tag (e.g., FLAG peptide from Sigma-Aldrich), and the cells secreting the protein of interest may be labeled using a detectable anti-epitope antibody (for example a monoclonal anti-FLAG antibody). Selection of cells expressing high levels of protein of interest can be carried out using multiple rounds of cell sorting and amplification by cell culture growth. Each round of selection involves the sorting of cells on the basis of the intensity of a detectable label such as fluorescence. Separation may be done by any of the methods known in the art including the fluorescence activated cell sorting (FACS) system, the magnetic cell sorting system (MACS), or any other suitable cell separation or sorting technique.

Some aspects of the invention relate to methods to screen for cells expressing a protein of interest (e.g., antibody, antibody-mimic proteins, scaffold proteins, receptors) that can interact with a specific target molecule (e.g., antigen or ligand) with a desired specificity. Other aspects of the invention relate to the enrichment for a protein of interest having a high (e.g., highest or optimized) specificity for a target molecule (e.g., antibodies having a high, for example highest or optimized, affinity for an antigen).

In an exemplary embodiment, in vivo or in vitro biotinylated host cells are first incubated in the presence of soluble avidin and with a biotinylated ligand or antigen. In some embodiments, the ligand or antigen is labeled using an epitope-tag (e.g., His6 tag). The cells displaying the antigen at their surface are then incubated to allow secretion of a protein of interest (e.g., receptor, antibody, enzyme, scaffold protein or any other protein of interest) having an affinity for the ligand or antigen. Cells expressing the protein of interest bound to the antigen can be detected based on the reporter moiety of the secreted protein, the ligand or both, and can be isolated by various methods. In some embodiments the secreted proteins or ligand are not biotinylated. In some embodiments, cells are labeled with a labeled antibody against the protein of interest or with a detectable anti-class antibody to detect the protein of interest and with a labeled antibody against the antigen or with antibody recognizing a tag epitope on the antigen. Alternatively, if the protein of interest is fused with an epitope-tag (e.g., the FLAG peptide from Sigma Aldrich), the cells secreting the protein of interest may be labeled using a detectable anti-epitope antibody (for example a monoclonal anti-FLAG antibody).

Selection of host cells displaying, for example, a high affinity or specificity (e.g., extraordinarily high affinity or specificity) for the ligand or antigen of host cells secreting high levels of protein of interest may be carried out using multiple rounds of cell sorting and amplification by cell culture growth. Each round of selection involves the sorting of cells on the basis of the detectable label such as fluorescence. In some embodiments, libraries of candidate proteins are screened for their ability to bind a surface displayed antigen. A range of ligand or antigen concentration may be used for different rounds of sorting depending on the desired affinity of a displayed protein for its ligand or antigen. Separation may be done by any of the methods known in the art including the fluorescence activated cell sorting (FACS) system, the magnetic cell sorting system (MACS), or any other suitable cell separation or sorting technique.

It should be appreciated that techniques described herein may be used for sorting, screening, selecting, and/or isolating cells on the basis of two or more properties (e.g., two or more of expression, display, affinity, activity, etc.). In some embodiments, cells that are isolated on the basis of one or more properties may be further evaluated (e.g., the encoded engineered proteins may be assayed for one or more functions or properties of interest). For example, cells may be isolated based on the level of expression and/or binding properties and/or enzymatic properties of displayed engineered protein variants encoded by the cells. The encoded proteins subsequently may be assayed (e.g., in the context of a cellular display system, or after isolation and/or purification from the host cell) for one or more similar or additional properties (e.g., in an in vitro assay, in a non-cellular environment, and/or when administered as a research or pharmaceutical preparation to a subject such as a mammal, e.g., a human).

Evaluation of Engineered Proteins

In one aspect, the invention provides methods for evaluating if an engineered protein has a predetermined function or property. In one aspect, the invention provides methods for assaying for a predetermined function or property of an engineered protein. It should be appreciated that property and function can be used interchangeably and include an amount and/or level of any of the following: protein expression, secretion, display, enzymatic activity, binding affinity (e.g., antigen and/or ligand binding), stability, etc., or any combination thereof. Accordingly, a predetermined function or property may be any physical, chemical or biological characteristic of a protein, including but not limited to, stability, size, structure, resistance towards proteases, enzymatic properties including substrate specificity, binding properties including antigen or ligand binding etc., or any combination thereof. Predetermined protein functions are protein functions that may be desired for a specific protein, e.g., increased stability or increased resistance to proteases.

In addition, a predetermined function may be evaluated through comparison to a threshold level of the functionality. In some embodiments, proteins with a certain level of predetermined functionality or property may be selected. In some embodiments the level of engineered protein that is displayed is assayed by detecting a level of a reporter molecule, epitope tag, antigen, or ligand that is attached to the engineered protein. In some embodiments the protein property can be evaluated by challenging the protein to a specific condition. For instance, if the predetermined property is protein stability, proteins above a certain resistance towards a chaotropic reagent can be selected. The selected proteins may subsequently be analyzed. Methods of analysis may include the determination of the primary and secondary sequence. In some embodiments, the selected proteins may be pooled and subjected to one or more rounds of selection. In some embodiments, the selected proteins may be subjected to one or more additional structural or functional assays.

To evaluate whether an engineered protein has a predetermined function, the engineered protein can be expressed in a host cell. In some embodiments, expression is induced by the addition of an agent to the environment of the host-cell. The expression of the engineered protein results in the immobilization of the engineered protein on the cell surface through binding of the engineered protein to a first binding partner. Any of the embodiments described herein can be used to arrive at an engineered protein bound to a first binding partner or target molecule, wherein the first binding partner or target molecule is connected to the cell surface, thereby resulting in the immobilization of the engineered polypeptide. Once immobilized, the engineered protein can be evaluated for the predetermined protein function.

In some embodiments, libraries of nucleic acids encoding protein of interest variants can be expressed and screened for the predetermined function. In some embodiments, libraries of cells comprising nucleic acids encoding the protein of interest variants can be expressed and screened for the predetermined function or property. It should be appreciated that libraries of nucleic acids encoding the protein of interest variants can be screened for multiple properties or functions. In addition, the libraries can be subjected to multiple rounds of screening for one or more properties resulting in an enrichment of the library for that one or more properties.

Methods for evaluating protein functions are known in the art. In some embodiments, the engineered protein will comprise a reporter moiety, such as a fluorescent moiety, and the signal of the reporter moiety can be used to evaluate a specific protein function. The specific assay used to evaluate a protein function depends on the particular protein function being evaluated. For instance, if the predetermined function is protein stability, an immobilized engineered protein can be challenged with chaotropic reagents or to increased temperature, and changes in the physical structure of the protein (e.g., protein folding) can be observed, wherein a higher stability is correlated with the capacity to maintain protein folding at higher chaotropic concentrations.

Stability of a protein or a protein variant may be critical for the function of expressed proteins (e.g., single chain antibody, see e.g., Worn et al., J. Biol. Chem., 2000, 275: 2795-2803). Standard approaches to evaluate the stability of a protein include measuring the melting temperature of the protein ($T_m$) using for example scanning calorimetry and/or the free energy of unfolding ($\Delta G$) at a specific temperature (e.g., 25° C.) using, for example, guanidium hydrochloride or urea denaturation followed by tryptophan intrinsic tryptophan fluorescence or circular dichroism. Thermal stability has been shown to be correlated to the secretion and the yeast cell surface display of single chain T cell receptor (Shusta et al. J. Mol. Biol., 1999, 292: 949-956 and U.S. Pat. No. 6,300,065). In some embodiments, a measure of the expression levels of the proteins or protein variants may be used to select for more stable proteins. According to aspects of the invention, more stable proteins have higher expression levels and can be identified by isolating highly expressed proteins (e.g., proteins that are expressed at higher levels than an initial or reference protein). In some embodiments, the expression level is determined by labeling the protein using a reporter moiety to determine the amount of expressed protein per cell or per cell surface area. Populations of cells expressing a more stable variant may be identified and isolated by fluorescence activated cell sorting (FACS). The highest expressing populations may be collected by FACS and subjected to a subsequent round of sorting, thereby enriching the population with cells expressing the more stable protein variant. In some embodiments, a library of protein variants may be screened for protein expression to select for protein variants with improved biophysical properties (e.g., stability). In one embodiment, protein variants showing an expression level of at least 5, 10, 20, 40 or 50 fold higher than the corresponding wild type protein are selected.

If the desired predetermined function to be evaluated is insensitivity towards proteases, the immobilized protein can be challenged with increasing concentrations of one or more proteases, and the integrity of the engineered protein monitored. If the predetermined function is a biological function, such as a specific enzymatic activity, an assay appropriate to that particular enzymatic function can be performed. Enzymatic assays are performed routinely art and a person of ordinary skill in the art will know what enzymatic assay to use to evaluate a specific enzymatic function.

Evaluation of Protein Complexes

In one aspect, the invention provides methods for evaluating whether a protein complex has a predetermined function or property. In one aspect, the invention provides methods for assaying the predetermined function of a protein complex. A protein complex comprises two or more engineered proteins that interact with each other. To evaluate whether a protein complex has a predetermined function, a protein complex comprising one or more engineered proteins is produced and evaluated for a predetermined function (e.g., one or more engineered proteins may be expressed under conditions that allow them to interact and form a protein complex that can be evaluated in vivo or in vitro). Engineered proteins of a protein complex can interact with each other when one or more of the engineered proteins are expressed and immobilized on a host cell surface. Embodiments of methods for expressing and immobilizing engineered proteins on a cell surface have been described above. In some embodiments, the immobilized protein complex can be evaluated for a predetermined function. Techniques that are used to evaluate a predetermined function of a protein complex may be the same techniques as those that are used to evaluate embodiments of engineered proteins.

It should be appreciated that the engineered proteins of the protein complex do not have to be processed in the same way. For instance a first engineered protein of a protein complex can be expressed from a vector which is transiently present in a host cell, while the second engineered protein of the protein complex is expressed from a gene integrated in the genome of the cell. Two engineered proteins can be expressed simultaneously, or a first protein can be expressed and immobilized on the cell surface prior to expression and immobilization of a second engineered protein. In some embodiments, a first engineered protein is immobilized on the cell surface and a second protein is added to the environment of the host cell, after which it interacts with the first engineered protein to form a protein complex. In some embodiments, one of the engineered proteins of the protein complex is a component of a library while the second engineered protein is not part of a library. This last embodiment allows for the evaluation of the components of a library of first engineered protein for the ability to form a protein complex or to have a particular function or level of activity with a second engineered protein. It should be appreciated that in some embodiments, only one protein of a protein complex is engineered to be secreted and anchored to a cell surface. The presence of at least one member of a protein complex anchored on a cell surface may be used to immobilize other members of the protein complex (e.g., engineered or non-engineered proteins) that interact with the anchored protein.

It should be appreciated that techniques described herein may be used for evaluating, sorting, screening, selecting, and/or isolating proteins or protein complexes on the basis of two or more properties (e.g., two or more of expression, display, affinity, activity, etc.).

It should be appreciated that any of the assays for cellular, protein, protein complex, and/or substrate analysis described herein may be based on standard binding, detection, and/or enzymatic assays. For example, display levels may be based on detecting a reporter molecule (e.g., an antigen and/or epitope, an enzymatic reporter that produces a detectable product, a functional reporter, or any other detectable or selectable reporter that allows quantification and/or selection based on predetermined levels of expression and/or activity, or any combination thereof).

Evaluation of Substrate Processing by an Engineered Protein

In one aspect, the invention provides methods for evaluating whether an engineered protein can process a substrate. In one aspect, the invention provides methods for assaying if an engineered protein can process a substrate. In another aspect, the invention provides methods for selecting an engineered protein capable of processing a substrate with a desired processing activity. In some embodiments, engineered proteins are screened for specific enzymatic activity. Enzymes of interest include, but are not limited to, polymerase, ligase, restriction enzyme, topoisomerase, kinase, phosphatase, metabolic enzyme, industrial enzymes etc, or any combination thereof. Processing a substrate may involve the modification of a substrate by an engineered protein or an interaction of the engineered protein with the substrate. Any substrate is embraced by the invention including polypeptides, nucleic acids, lipids, polysaccharides, synthetic polymers or synthetic compounds. Processing a substrate or interacting with a substrate may involve, but is not limited to one or more of the following processes: binding to the substrate, dissociating from the substrate, nicking the substrate, cutting the substrate, activating the substrate, deactivating the substrate, charging the substrate, decharging the substrate, changing substrate conformation, copying the substrate, replicating the substrate, conjugating molecules to the substrate, conjugating peptides to the substrate or modifying the substrate. In one embodiment, to evaluate whether an engineered protein can process a substrate, the engineered protein is expressed in a host cell, as described herein, resulting in the immobilization of the engineered protein on the cell surface through binding of the engineered protein to a binding partner Immobilized engineered proteins can subsequently be evaluated for the ability to process a substrate. The particular assay used to evaluate whether an engineered protein can process a substrate will depend on the specific processing event and/or substrate being evaluated. Assays to evaluate whether an engineered protein can process a substrate are known to people of ordinary skill in the art. The assays of the invention can be used to screen libraries of nucleic aids or libraries of host cells comprising nucleic acids encoding variants of proteins of interest.

Substrate Coupled to Cell Surface

In some embodiments, the substrate is coupled to a cell surface. Any method for coupling the substrate to a cell surface is embraced by the invention. Coupling the substrate to a cell surface may comprise the direct coupling of the substrate to the cell surface (e.g., to the surface carbohydrates or surface protein) or coupling the substrate to cell surface may comprise coupling the substrate to a linker which is connected to the cell surface. In some embodiments, the substrate is coupled to a binding partner that is connected to the cell surface. In some embodiments, the substrate binding partner is the same substrate binding partner to which the secreted engineered polypeptide is bound. In some embodiments, the substrate comprises a biotin moiety and the binding partner is a biotin binding partner, such as avidin. In some embodiments, the biotin binding moiety is bound to a biotin spacer, thereby connecting the biotin binding moiety to the cell surface. In some embodiments, the biotin spacer, the substrate comprising biotin and the engineered polypeptide are all bound to the same biotin binding agent. In some embodiments, the substrate and the engineered polypeptide are bound to different biotin binding agents. In some embodiments, multiple substrates and/or multiple engineered polypeptides are bound to an immobilized binding partner. Immobilizing both the substrate and the engineered protein may bring them into close proximity, thereby allowing for optimized assays to evaluate whether an engineered protein can process a substrate. However, it should be appreciated that the engineered proteins can still be evaluated for their ability to process a substrate even if the substrate is not coupled to the cell surface. For instance, the ability to process a substrate can be evaluated by adding the substrate to the host-cell environment.

In some embodiments, the processing of a substrate generates a detectable signal or a change in the level or type of a signal. The nature of the signal will depend on the specific assay used to evaluate processing of the substrate. In some embodiments, the signal is a fluorescent signal. Fluorescent signals can be generated through a variety of processing methods. Non-limiting examples of the generation of fluorescent signals are the incorporation in, or coupling of, a fluorescent moiety to a substrate. The invention also embraces assays based on the disappearance of a fluorescent signal, for instance the removal of a fluorescent moiety from a substrate by processing of the substrate, and assays based on a change in fluorescent signal. Assays based on a change in fluorescent signal also include FRET (Fluorescence Resonance Transfer), where a change in fluorescent signal is dependent on a change in distance between two fluorescent moieties. Assays based on a fluorescent signal also cover assays based on the generation of a fluorescent signal through a secondary event. For instance, a fluorescently labeled antibody can be added to a substrate that is being processed to monitor for the appearance/disappearance of a particular substrate characteristic.

Evaluation of Substrate Processing by a Protein Complex

In one aspect, the invention provides methods for evaluating whether a protein complex can process a substrate. In one aspect, the invention provides methods for assaying if a protein complex can process a substrate. A protein complex comprises one or more engineered proteins that interact with each other. In some embodiments, the engineered proteins of the protein complex are expressed in the host cell and immobilized on the host cell surface, resulting in an interaction between the engineered proteins of the protein complex. Embodiments for evaluating whether a protein complex can process a substrate are similar to embodiments for evaluating whether an engineered protein can process a substrate, as described herein. In some embodiments, the substrate is coupled to the cell surface.

Screening of Candidate Engineered Proteins

In one aspect, the invention provides methods for screening candidate engineered proteins. In some embodiments, the method comprises the introduction of a library or plurality of vectors into a population of host cells. In some embodiment, the population of host cells displays a first binding partner at its cell surface. Each vector may comprise a gene coding for a unique engineered protein and components to allow for the expression of the gene in the host cell. In addition, each engineered protein may comprise a modification motif. In some embodiments, the modification motif is the same for each engineered protein. The host cells are grown under conditions sufficient to induce expression of the engineered proteins and produce a modification on the modification motif. In some embodiments, the modification motif is an immobilization peptide and the modification comprises coupling of a second binding partner to the modification motif. The modified engineered proteins are secreted and bind to a first binding partner which is connected to the cell surface in vivo or in vitro. In some embodiments, the first binding partner is avidin and the second binding partner is biotin. In yet other embodiments, the first binding partner is biotin and the second binding partner is avidin. Once the engineered proteins are immobilized on the cell surface the proteins can be evaluated for a predetermined function. In some embodiments, the members of the library are compared to each other or to an engineered protein with a known predetermined function.

In some embodiments, the predetermined function comprises the processing of a substrate. In some embodiments, processing of a substrate results in a signal (e.g., change in fluorescence, change in color, or loss of such a signal originally incorporated in the unprocessed substrate, etc.). In some embodiments, the signal generated by processing of the substrate is compared to a threshold level. Comparing the signal level to a threshold level facilitates the identification of engineered proteins with a predetermined function. For instance if the threshold level of a signal for a particular substrate processing event is 10, and the engineered proteins are evaluated for the ability in that particular processing event, then any engineered protein with a signal higher than 10 is a candidate engineered protein. In contrast, if a desired protein function is to have less activity for a certain process (for instance, an unwanted non-specific side reaction) than an engineered protein with a signal lower than 10 is a candidate engineered protein. In some embodiments, the threshold signal is a signal generated by a polypeptide with random coil structure. In some embodiments, the threshold signal is a signal generated by a wild type version of the engineered candidate protein. In some embodiments, the threshold signal is a signal generated by a commercially available variant of the engineered protein.

It should be appreciated that any of the binding or substrate assays described herein may be used to identify or select protein or target molecule variants that have one or more new or modified properties or functions. For example, polymerases with increased processivity, lower error rates, increased salt and/or thermal stability, etc., or any combination thereof may be identified and/or isolated according to aspects of the invention.

Libraries

It should be appreciated that any of the protein functions or properties described herein may be evaluated, screened for (or against) or selected (or against) in the context of a single type of cell expressing a single type of engineered protein or in the context of a library of cells each expressing a different engineered protein or protein variant. In one aspect, the invention provides methods for generating libraries of engineered proteins or libraries of nucleic acid and/or polypeptide components, such as vectors of nucleic acid coding for the engineered proteins that can be used to generate libraries of engineered proteins. In some embodiments, a library comprises two or more variants of an engineered protein or component thereof, e.g., two or more variants of an engineered protein wherein each variant comprises a unique engineered protein with only a minor change in amino acid composition. In some embodiments, a library comprises two or more unrelated sequences. For instance, to identify a candidate engineered protein that can inhibit an enzyme, a library of engineered proteins with random sequence or pre-determined sequences may be interrogated. A library can have at least 2, at least 5, at least 10, at least 50, at least 100, at least 1000, at least 10,000, at least 100,000, at least 1,000,000, at least $10^7$, at least $10^8$, at least $10^9$, at least $10^{10}$ or at least $10^{11}$ members.

Libraries of the invention include libraries of host cells, wherein each host cell expresses a unique engineered protein and wherein each engineered protein comprises a unique polypeptide linked to an immobilization peptide (e.g., the same immobilization peptide). The vectors can be integrated into the genome of the host cells or the vectors can be freely replicating, e.g., plasmids that have been introduced into the host cell but have not been integrated in the genome of the host cell. The library can also comprise a combination of host cells comprising freely replicating and integrated vectors. Libraries of the invention also may be libraries of host cells, wherein each host cell displays on its surface a unique fusion protein, and wherein each engineered protein comprises a unique polypeptide coupled to an immobilization peptide.

In some embodiments, the library provides host cells with a high density of engineered proteins immobilized on the cell surface. In some embodiments, the high density is accomplished by binding multiple engineered polypeptides to one binding partner. In some embodiments, the number of engineered proteins per cell is greater than $10^3$, greater than $10^4$, greater than $10^5$, greater than $10^6$, greater than $10^7$, or greater than $10^8$ engineered proteins per cell. In some embodiments, the immobilization peptide is a biotinylation peptide. In some embodiments, the immobilization peptide is a transmembrane protein. In some embodiments, the immobilization peptide comprises a GPI anchor. In some embodiments, the immobilization peptide is a peptide that is naturally present on the cell surface. In some embodiments, the immobilization peptide is a peptide that binds one or more molecules naturally present on the cell surface (e.g., surface carbohydrates or proteins on the cell surface).

The invention also embraces libraries of vectors, wherein each vector comprises a nucleic acid encoding a unique engineered protein and wherein each engineered protein comprises a unique polypeptide coupled to an immobilization peptide and/or comprises a mobilization motif.

The invention also embraces libraries of engineered proteins, wherein each engineered protein comprises a unique polypeptide coupled to an immobilization peptide.

In any of the libraries of the invention, the engineered protein can comprise a therapeutic polypeptide, polymerase, ligase, restriction enzyme, topoisomerase, kinase, phosphatase, metabolic enzyme, catalytic enzyme, therapeutic enzyme, pharmaceutical enzyme, environmental enzyme, industrial enzyme, pharmaceutical polypeptide, environmental polypeptide, industrial polypeptide, binding protein, antibody, antibody fragment, signaling molecule, cytokine, receptor, or any combination of two or more thereof.

In some embodiments, libraries of antibodies or other binding proteins (e.g., single chain antibodies, scaffold proteins, etc.) may be evaluated or screened to identify and/or isolate variants that i) bind to a chosen antigen and/or epitope and/or other target molecule (e.g., a novel antigen and/or epitope) and/or ii) have high (e.g., increased) affinity for a particular antigen and/or epitope and/or other target molecule. Methods of the invention may be designed to identify antibodies or other binding proteins that have affinities, for a particular antigen and/or epitope and/or other target molecule, greater than a binding affinity represented by a dissociation constant of about $10^{-7}$ M, about $10^{-8}$ M, about $10^{-9}$ M, about $10^{-10}$ M, about $10^{-11}$ M, about $10^{-12}$ M, about $10^{-13}$ M, about $10^{-14}$ M or about $10^{-15}$ M. In some embodiments, a single antibody or other binding protein may be assayed to against a library of target molecules to identify one or more target peptide sequences (e.g., novel or modified ligand, antigen, epitope, receptor, dimerization, mulitmerization, or other binding motifs or proteins) that bind to the antibody or other binding protein. Similarly, methods of the invention may be designed to identify target peptide sequences that have affinities, for a particular antibody or other binding protein, greater than a binding affinity represented by a dissociation constant of about $10^{-7}$ M, about $10^{-8}$ M, about $10^{-9}$ M, about $10^{-10}$ M, about $10^{-11}$ M, about $10^{-12}$ M, about $10^{-13}$ M, about $10^{-14}$ M or about $10^{-15}$ M.

Production of Proteins

In order to be able to produce proteins of interest, the nucleic acid of the selected host cell is traditionally recovered, amplified and cloned into an expression vector. For example, the DNA of a selected antibody, or protein of interest producing cell can be extracted from the host cell, amplified, cloned, and expressed to produce proteins with desired antigen specificity or other characteristic.

One aspect of the invention relates to the display, screening and production of a protein of interest in a host cell. In one embodiment, the host cell displaying a protein of interest is selected and may be switched from a displaying mode to a producing mode. In a display mode, a library of proteins variants is expressed by a population of host cells and immobilized at the cell surface. As described above, the display mode allows for the screening of a library of proteins variants and sorting of the proteins variants based on their expression level, stability or affinity for a target molecule. In the production mode, cells expressing protein variants that have been selected in the display mode, secrete the protein of interest in the extracellular medium. One should appreciate that depending on the mode of display, omitting one step involving the expression/display/addition of one of the binding partner of the display system can lead to the secretion of the protein of interest from the cell. For example, if a protein of interest needs to undergo in vivo biotinylation to be displayed at the cell surface, non-expression of the BirA gene (by repression, non-induction etc. . . . ) will result in the expression of non-biotinylated cell wall proteins or the expression of non-biotinylated protein of interest and will lead to the secretion of the protein of interest. If the display system involves the step of binding avidin to the biotin on the cell surface, incubation of the cells in an avidin-free medium will result in the secretion of the protein of interest. Alternatively, if the host cells surface proteins are chemically biotinylated in vitro, incubating the cells in a biotin free medium will also result in the secretion of the protein of interest. Any method of switching the cell from display mode to production mode is embraced by the invention.

Figure 5B:
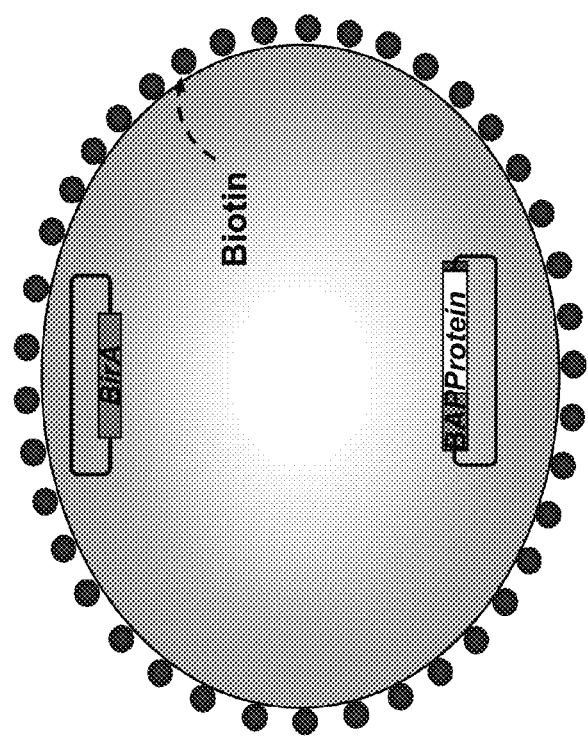
Figure 5A:
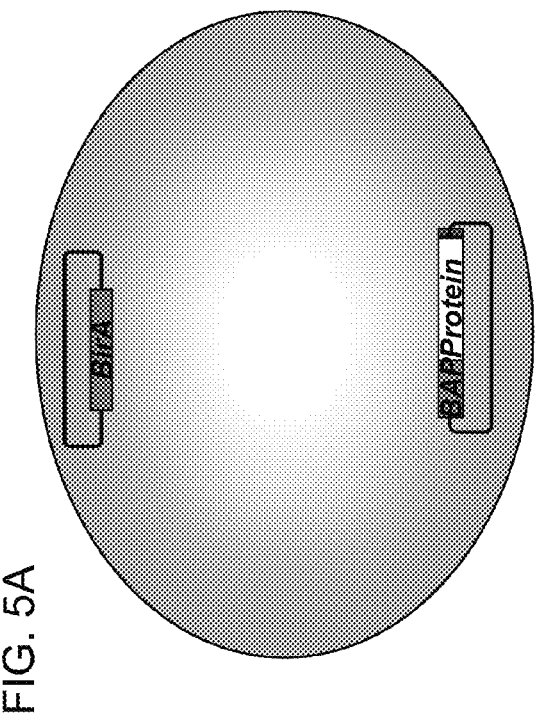
Figure 6A:
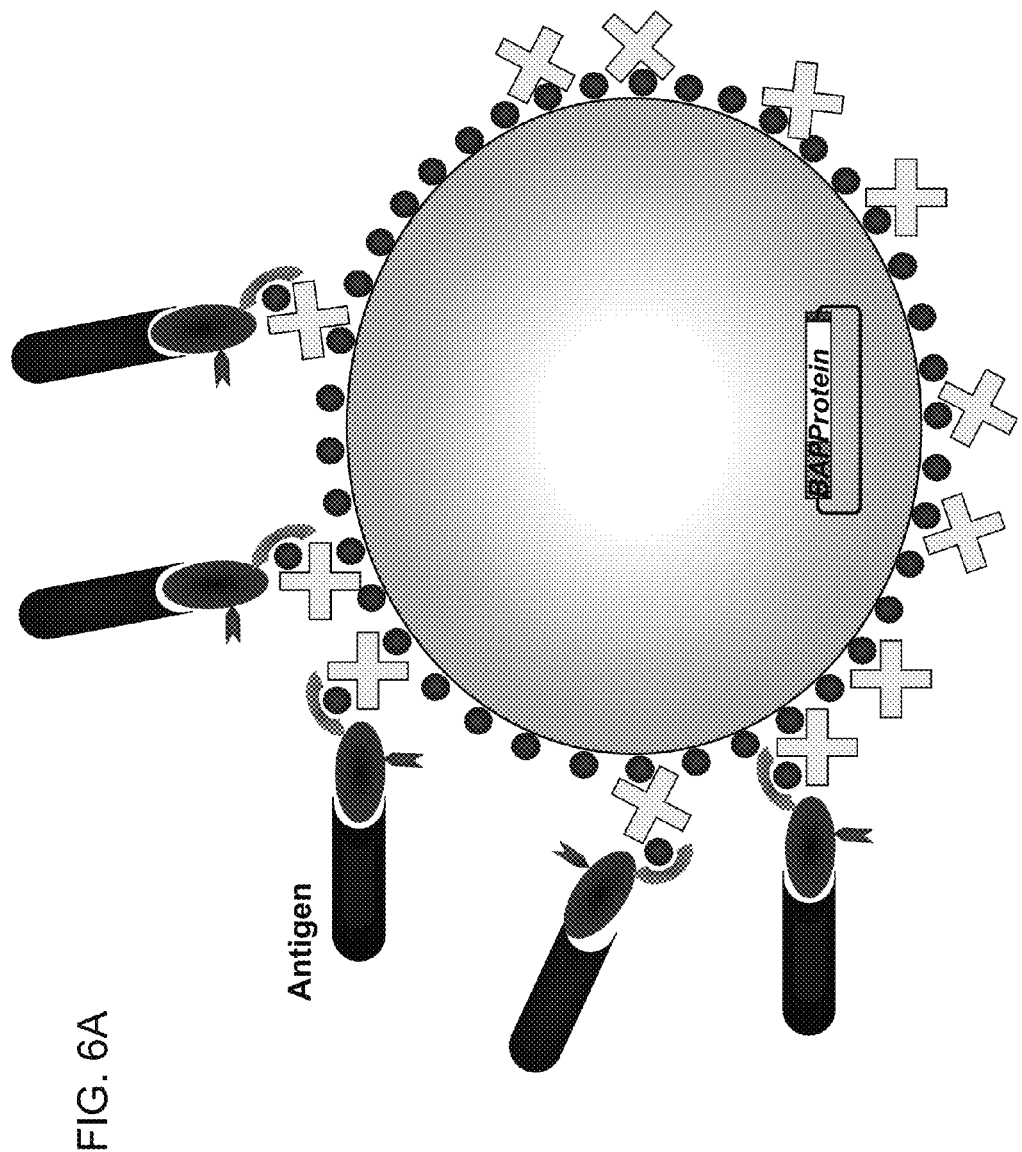
FIGS. 6A-6C illustrate an embodiment of the display of a target molecule on the cell surface.
Figure 6B:
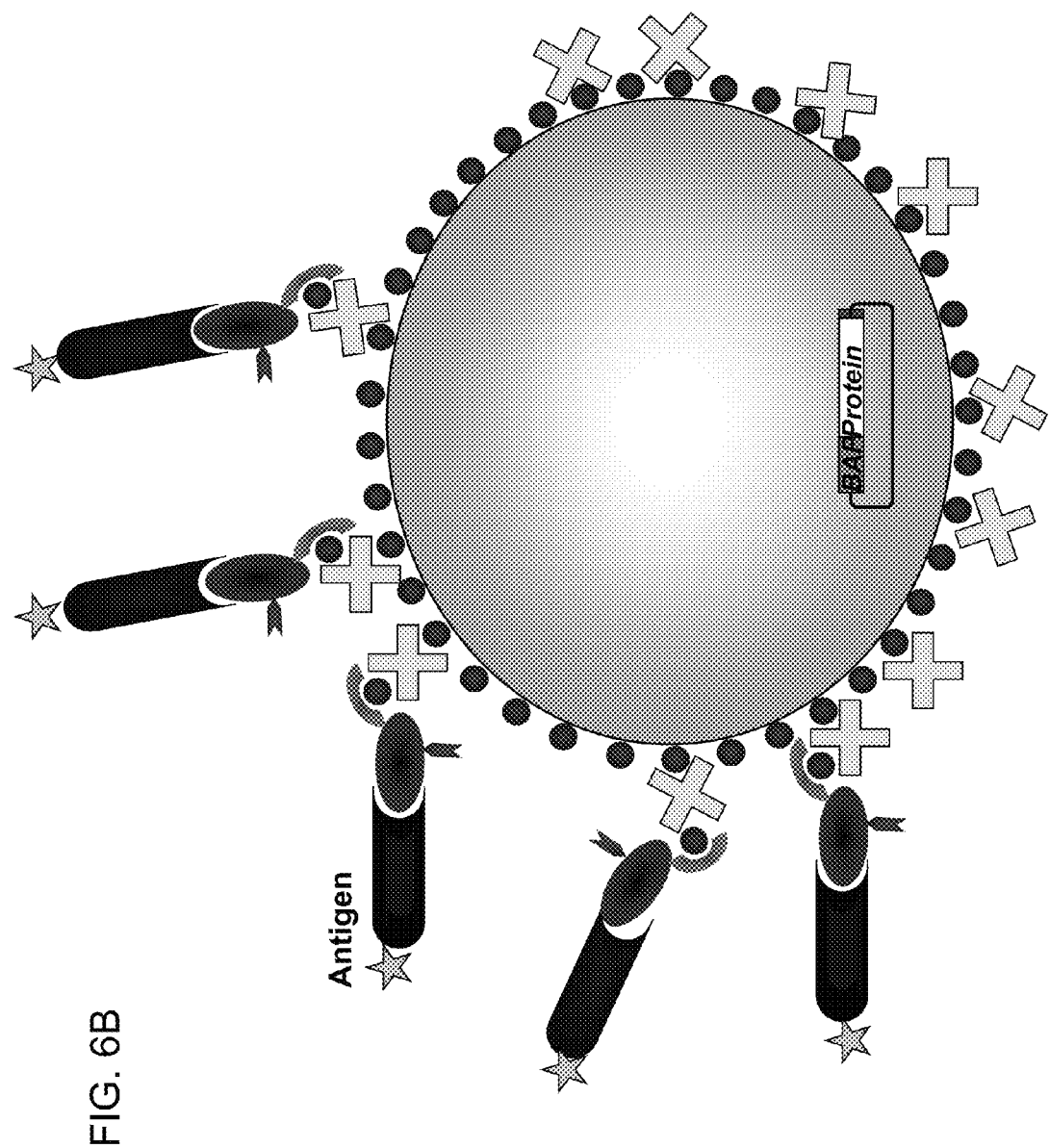
Figure 6C:
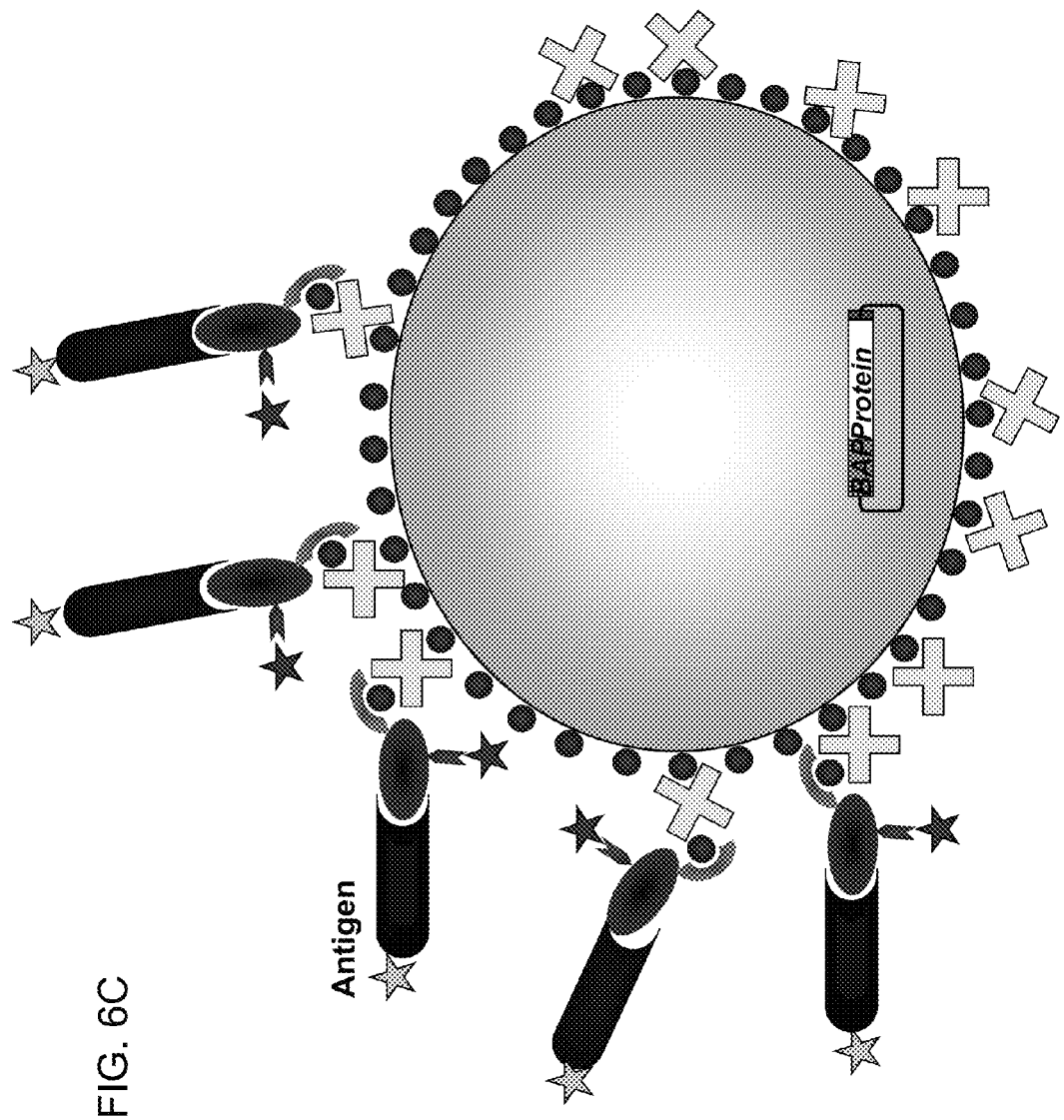
Figure 7A:
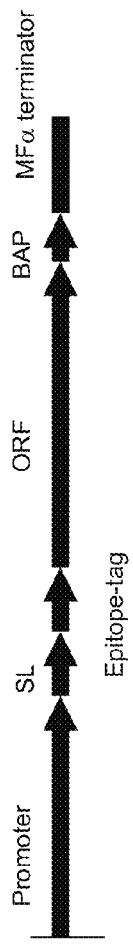
FIGS. 7A-7D show a non-limiting embodiment of the expression of an scFv protein.
Figure 7B:
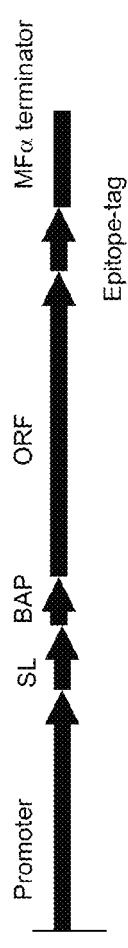
Figure 7D:
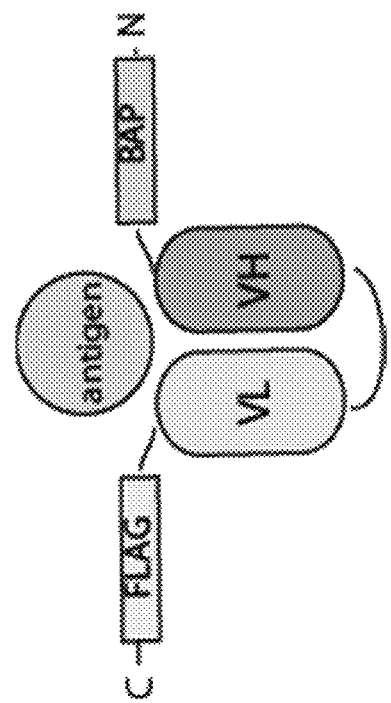
Figure 7C:
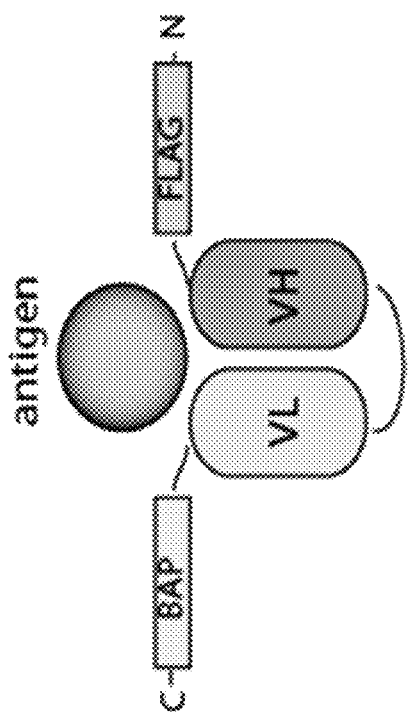
Figure 8A:
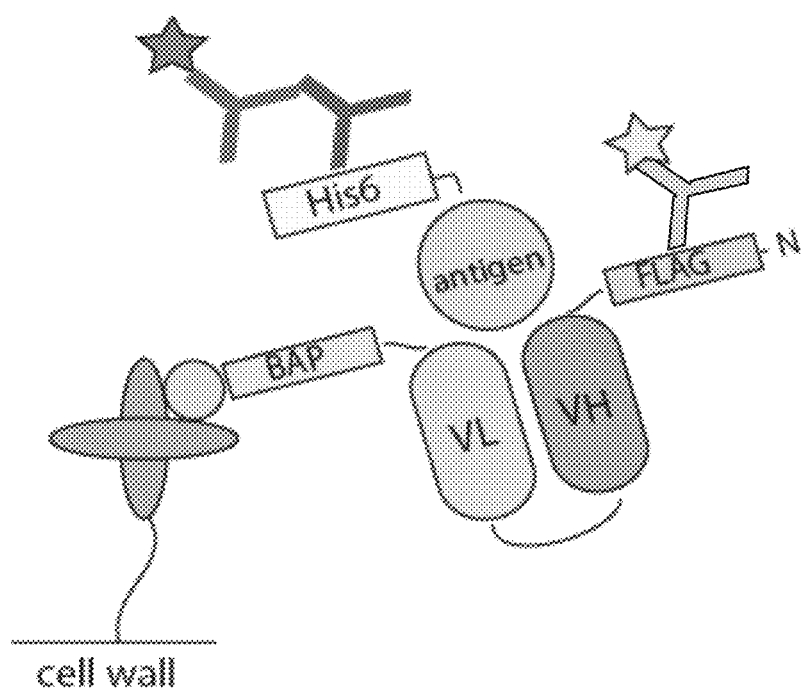
FIGS. 8A-8D show a non-limiting embodiment of the display of the scFv protein at the cell surface and the selection of the cells expressing the scFv protein bound to an antigen.
Figure 8C:
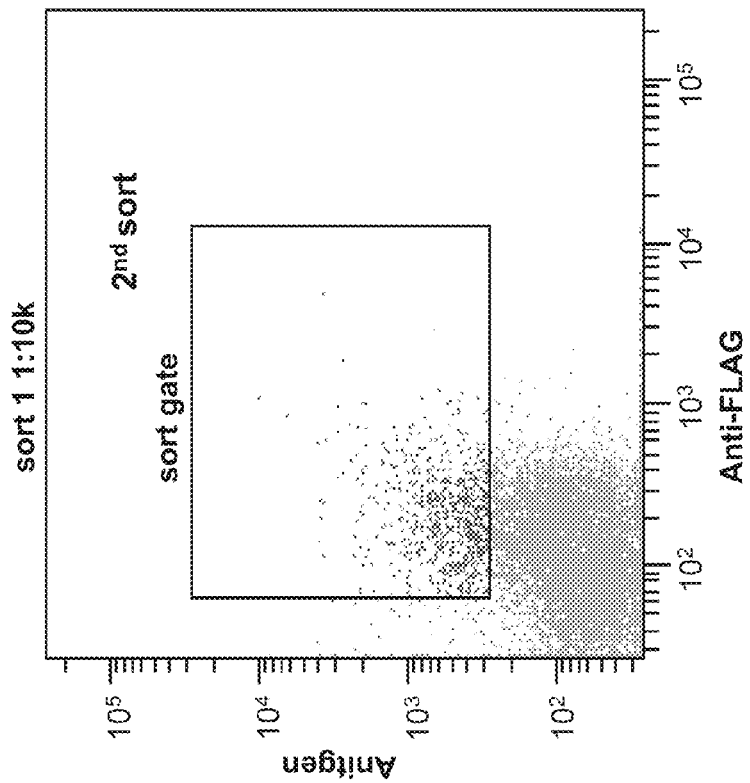
Figure 8B:
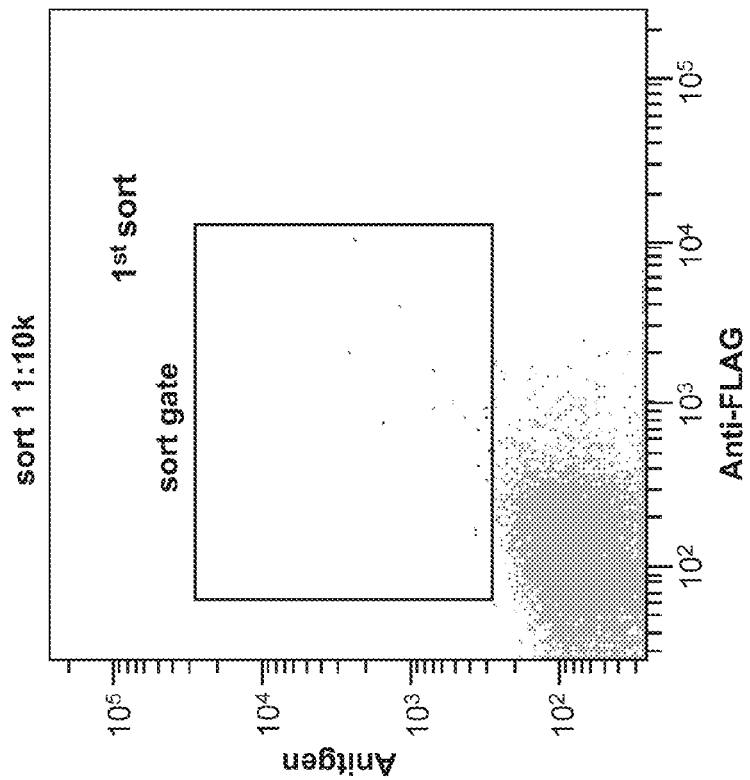
Figure 8D:
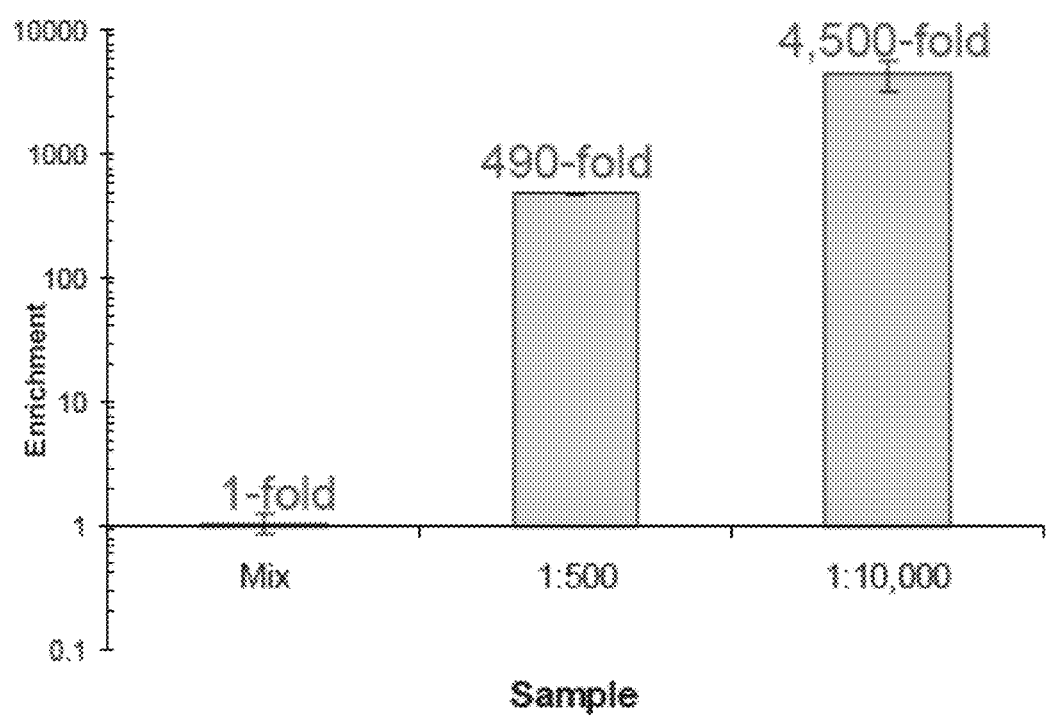
Figure 9B:
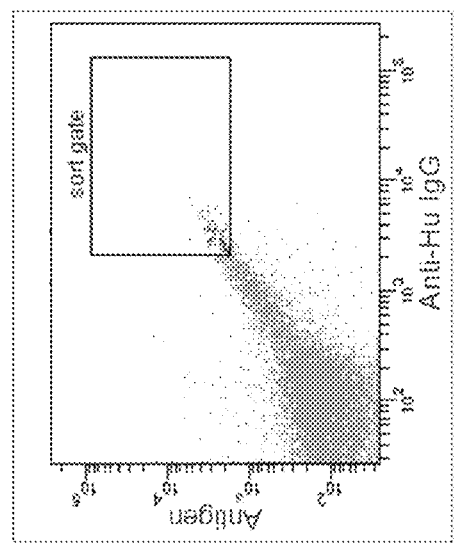
FIGS. 9A-9B show a non-limiting embodiment of a display of an antibody.
Figure 9A:
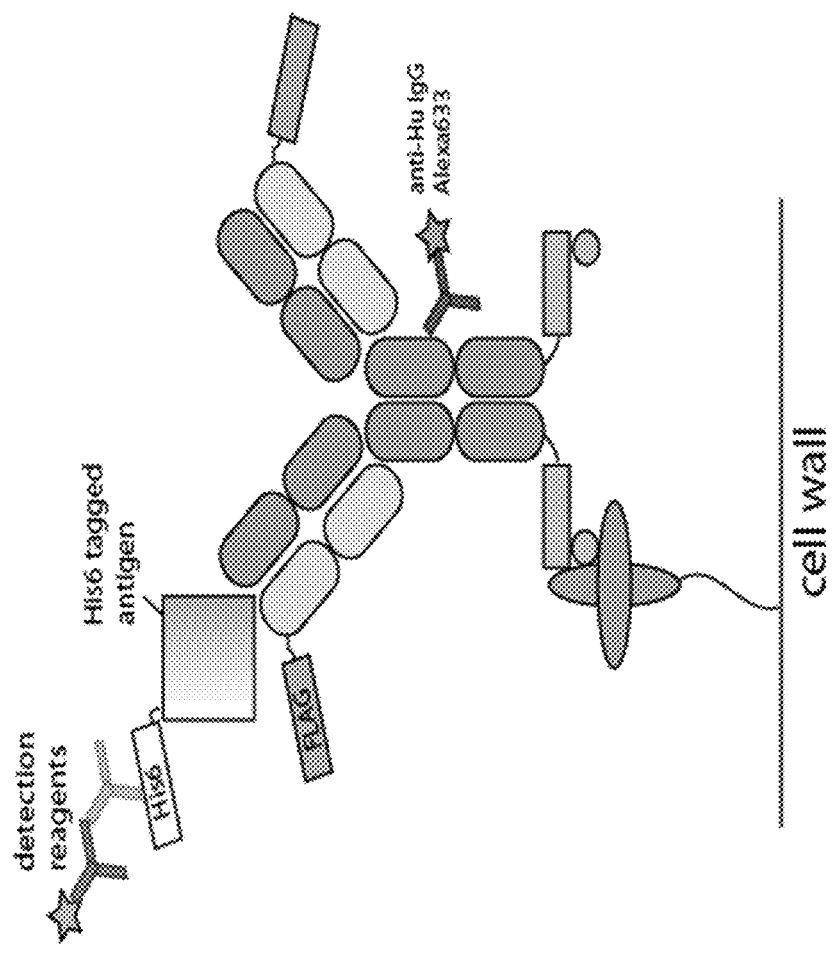

Aspects of the invention are illustrated by the attached figures that relate to non-limiting embodiments of expression and display systems. For example, FIGS. 1-2 illustrate embodiments of an engineered protein that is biotinylated in vivo, secreted, and displayed on the cell surface by binding to avidin attached to the cell surface. FIGS. 3-4 provide experimental results using non-limiting display methods of the invention. FIGS. 5-6 illustrate additional non-limiting examples of protein modification and display using methods and compositions of the invention. FIGS. 7-12 illustrate non-limiting examples of antibody display applications using compositions and methods of the invention. FIGS. 13-16 illustrate non-limiting examples and experimental results of substrate display assays using compositions and methods of the invention. These and other aspects of the present invention are further illustrated by the following Examples, which in no way should be construed as further limiting. The entire contents of all of the references (including literature references, issued patents, published patent applications, and co-pending patent applications) cited throughout this application are hereby expressly incorporated by reference.

EXAMPLES

Example 1: Protein Immobilization Through Intracellular Biotinylation

In vivo protein display methods typically rely on the expression of proteins as fusions to cell wall, cell membrane, or phage particle proteins. As an alternative to these traditional methods, proteins may be expressed from vectors and biotinylated in vivo. The biotinylated proteins may be subsequently secreted or excreted into the supernatant where the biotinylated proteins may bind to avidin that has been attached to the cell surface via a biotin linker. This "biotin-avidin sandwich" immobilizes the biotinylated proteins on the surface of the cell. Proteins immobilized on cells are fluorescently labeled and phenotypic assays are performed to select proteins with desirable phenotypes. Cells with immobilized proteins with desirable phenotypes are isolated by flow cytometry or another form of selection such as panning against immobilized antigen. If desired, multiple rounds of selection and isolation are performed. The isolated cells are expanded in culture and the nucleic acid coding for the protein with the desirable phenotype is identified. Optionally, an N-terminal secretion signal is used for expression in eukaryotic cells. The protein is transcribed and subsequently biotinylated through the overexpression of the BirA biotinylating enzyme. In the next step, the protein is secreted into the supernatant or excreted through mild cell surface permeabilization performed by media supplement addition or the co-expression of permeabilizing proteins. Finally, the biotinylated protein is immobilized on the surface of the cell by avidin, conjugated to the cell surface directly or anchored to the cell surface through a biotin-PEG-NHS linker or biotinylated cell wall protein. A synopsis of an example of a biotinylation protein engineering system is presented in FIG. 1 and FIG. 2.

In Vivo Biotinylation

The method for capturing biotinylated protein on the cell surface can be combined with the method of biotinylating and secreting the protein of interest. Protein biotinylation in vitro is a common molecular biology technique, and can also be performed in vivo (Samols, D., Thornton, C. G., Murtiff, V. L., Kumar, G. K., Haase, F. C., and Wood, H. G. (1998) *J. Biol. Chem,* 263, 6461-6464). Most of the proteins that are naturally biotinylated in vivo act as biotin transporters. One such transporter is the biotin carboxyl carrier protein (BCCP) in *E. coli*. BCCP is biotinylated on lysine side chains by an enzyme called biotin haloenzyme synthetase (BirA) (Fall, R. R. (1979) *Methods in Enzymology,* 62, 390-398; Barker, D. F. and Campbell, A. M. (1981) *J. Molecular Biology,* 146, 469-492; Howard, P. K. Shaw, J., and Otsuka, A. J. (1985) *Gene,* 35, 321-331; Barker, D. F., and Campbell, A. M., (1981b) *J. Molecular Biology,* 146, 451-467). In vivo biotinylation of heterologous proteins (i.e., proteins that are not natural substrates for biotinylation) is accomplished by fusing a BCCP domain or a BCCP domain mimic to the protein of interest and expressing the fusion protein in conjunction with overexpression of the BirA gene (Cronan, J. E. (1990) *J. of Biological Chemistry,* 265, 10327-10333; Yamano, N., Kawata, Y., Kojima, H. Yoda, K., and Yamasaki, M. (1992) Bioscience, *Biotechnology, and Biochemistry,* 56, 1017-1026; Schatz, P. J. (1993) *BioTechnology,* 11, 1138-1143; Tsao, K. L., DeBarbieri, B., Michel, H. and Waugh, D. S. (1996) *Gene,* 169, 59-64). An interesting in vivo biotinylation system is the BIOTRX construct (Smith, P. A., Tripp, B. C., DiBlasio-Smith, E. A., Lu, Z., LaVallie, E. R., McCoy, J. M. (1998) *Nucleic Acids Research,* 36(6), 1414-1420). This construct comprises a small biotin acceptor peptide fused to the N-terminal region of thioredoxin. Thioredoxin is a small protein normally involved in cytosol redox but that can also be used as a fusion partner for heterologous protein production. The BIOTRX construct correctly directs the production of biotinylated IL-12 in vivo.

Secretion/Excretion of Biotinylated Protein

The in vivo biotinylation system is designed to excrete or secrete the biotinylated proteins into the supernatant without irreparably damaging the cell. For eukaryotic systems, such as yeast, the biotinylated protein is expressed and secreted by fusing the protein to an N-terminal secretion signal sequence. Numerous examples of signal sequences exist for *S. cerevisiae* and any one of them can be used to direct secretion. Because the secretory pathway is spatially segregated from the cytosol in eukaryotes, the BirA gene also needs to be directed to the secretory pathway through the N-terminal addition of a secretion signal. The BirA protein can be co-secreted with the engineered protein or retained in the secretory pathway through the C-terminal addition of the HDEL endoplasmic reticulum retrieval sequence. Prokaryotes such as *E. coli* lack an advanced secretory apparatus. The delivery of the biotinylated protein into the supernatant therefore may require adjusted growth conditions or specialized cell lines. Adding supplements, such as glycine, or detergents, such as Triton X-100, to the cell environment can promote cell membrane permeability allowing highly expressed proteins to leave the cell via mildly compromised cell membranes (Jang, K. H., Seo, K. B., Song, K. B., Kim, C. H., Rhee, S. K., (1999), *Bioprocess Engineering,* 21, 453-458; Kaderbhai, M. A., Ugochukwu, C. C., Lamb, D. C., Kelly, S. (2000) *Biochem. Biophys. Res. Comm.* 279, 803-807; Yang, J., Moyana, T., Mackenzie, S., Xiz, Q., and Xiang, J. (1998) *Applied Environmental Microbiology,* 67, 1805-1814). Co-expression of cellular proteins such as kil, TolAIII, and bacteriocin release protein (BRP) can enhance the release of intracellular protein by providing pores through which the protein can traverse the membrane or by increasing the permeability of the cell membrane (Zhou, S., Yomano, L. Pl, Saleh, A. Z., Davis, F. C., Aldrich, H. C., Ingram, L. O. (1999) *Applied Environmental Microbiology,* 65, 2439-2445; Kujau, M. J., Hoischen, C., Riesenberg, D., Gumpert, J. (1998) *Applied Microbial Biotechnology,* 49, 51-58; Van der Wal, F. J., ten Hagen-Jounman, C. M., Oudega, B., Luirink, J., (1995) *Applied Microbial Biotechnology,* 44, 459-465). Cells deficient in cell walls called L-form cells can also be used to secrete intracellular proteins into the supernatant.

Binding of Biotinylated Protein to the Cell Surface

The interaction between biotin and avidin is extremely tight ($K_d \sim 10^{-15}$ M) yielding a covalent-like interaction between the two moieties. A powerful display system for protein engineering is created by connecting avidin to the surface of a cell and binding a biotinylated protein of interest to the avidin. Proteins are immobilized on cell surfaces through avidin in ways that leave them accessible to modification or labeling by antibodies that will be used for selection via flow cytometry or panning against an immobilized antigen. Avidin can be covalently conjugated to the cell surface or avidin can be connected to the cell surface through a spacer.

Connection of Avidin Through a Spacer

In yeast and mammalian cells, a biotin may be attached to the cell surface via a polyethylene glycol linker, facilitated by the presence of an N-succimidyl ester (NHS) functional group. This NHS functional group allows the PEG to covalently attach to free amines present on proteins on the cell surface. On the other end of this PEG linker is the biotin. The free biotin binds avidin which, in turn, binds up to three other biotinylated proteins due to avidin's tetravalent avidity (FIG. 1).

Covalent Conjugation of Avidin to the Cell Surface

Figure 3A:
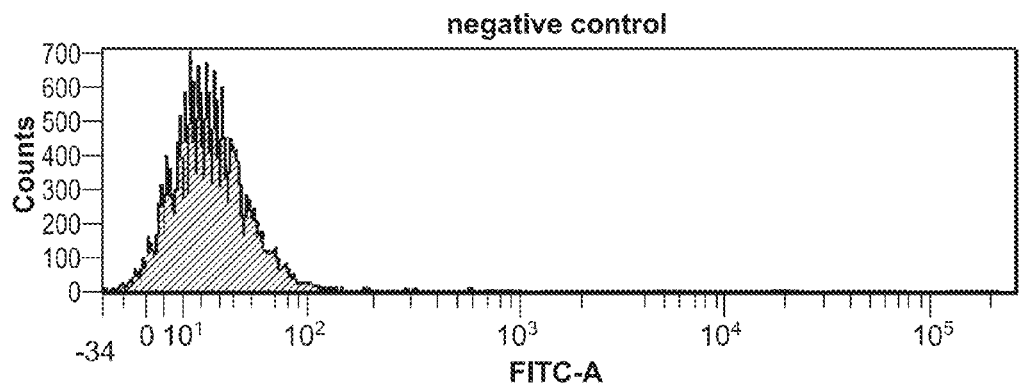
FIGS. 3A-3C show an embodiment where avidin is conjugated covalently to cells.
Figure 3B:
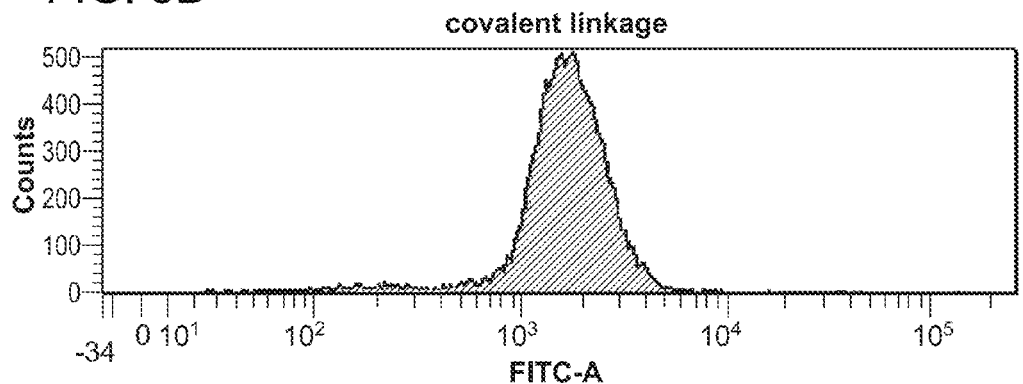
Figure 3C:
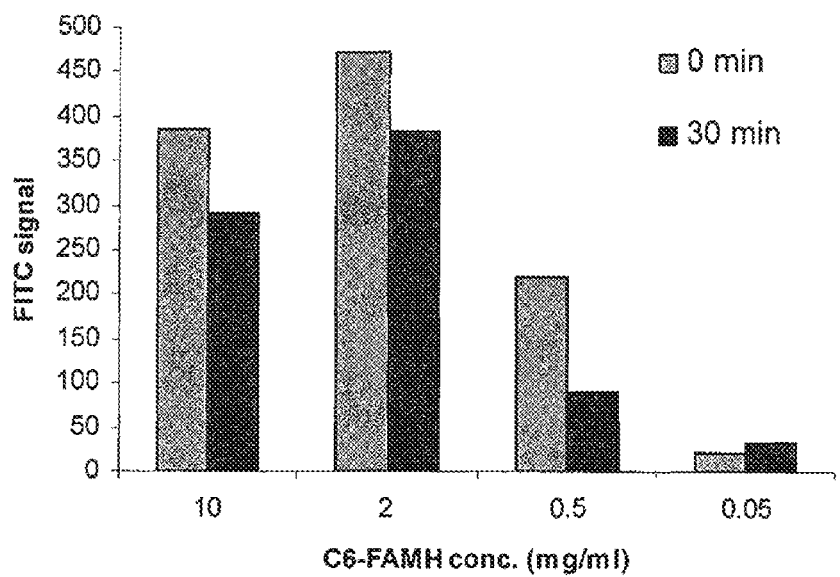

Avidin can be covalently conjugated to the cell surface through a hetero-bifunctional connector like C6-SANH (FIG. 2). Yeast cells were labeled with C6-SANH in carbonate buffered to a pH of 8.4 for 30 minutes at room temperature. Simultaneously, 200 µl of 50 mg/ml avidin was incubated in 5 mM periodate dissolved in phosphate buffer adjusted to a pH of 5.6 for 30 minutes at room temperature. After incubation periodate was removed using a desalting column, from which the avidin was eluted in phosphate buffer at pH 5.6. The periodate-treated avidin was then mixed with washed C6-SANH-treated cells for 30 minutes at room temperature. After the incubation, the cells were washed three times in PBS/BSA (pH 7.2), then labeled with biotinylated fluorescein to measure how much avidin was associated with the cell surface. After 20 minute incubation on ice, the cells were washed and analyzed by flow cytometry (FIG. 3A and FIG. 3B). To show the stability of the avidin-cell surface connection, cells were either labeled immediately with biotinylated fluorescein (0 min) or incubated in 1 mL PBS/BSA for 30 minutes at room temperature before labeling with biotinylated fluorescein (30 min) FIG. 3C demonstrates the stability of the avidin-cell linkage over time.

Example 2: Protein Display on the Yeast Surface Using Free Avidin to Replenish Surface Avidin Levels Yeast strain JKI100 (matα, GAL1 promoter BirA ligase::URA3, GAL1 promoter protein disulfide isomerase::LEU2, pep4::HIS, prb1Δ, trp1) was transformed with CEN plasmid carrying a small, single-domain, FLAG-tagged protein fused to the N-terminus of the BirA biotin acceptor peptide (BAP). Yeast were grown overnight in 5 mL SD-CAA media at 30° C. The cell culture was spun down and resuspended in 5 mL YPG/bovine serum albumin+2.5 μg/mL biotin supplement and shaken for six hours at 30° C. Approximately $1 \times 10^7$ cells were removed and mixed at a ratio of 1:300 with cells not expressing the protein-BAP fusion (1 expressing cell for every 300 non-expressing cells), and washed three times in 1 mL carbonate buffer (pH=8.4). The mixture of cells was resuspended in 40 μl 0.1 mg/ul NHS-PEG-biotin in carbonate buffer and incubated for 30 minutes at room temperature.

Cells were then washed three times in 1 mL PBS/BSA and incubated in 50 ul of 20 mg/mL avidin for ten minutes twice. Cells were inoculated into 3 mL biotin-less display media (made by mixing 30 μl of 100 mg/mL avidin with 3 mL filter sterilized biotin-less YPG/BSA/PEG (30 wt %)) and incubated in 2 wells of a six well plate overnight at 30° C. Cells were washed off the bottom of the well with 1 mL PBS/BSA and spun down and washed three times with 1 mL cold PBS/BSA. Cells were then incubated in 50 μl of 1:50 dilution chicken anti FLAG antibody for 20 minutes on ice. After washing in 500 μl PBS/BSA, cells were incubated in 50 ul 1:100 dilution goat anti-chicken Alexa633 and 50 nM biotin-fluorescein for 20 minutes on ice. After labeling, cells were washed once in 500 μl PBS/BSA and run on FACS.

The non-expressing cells were used as an internal negative control to demonstrate that protein capture (exhibited by a FLAG-positive population on the flow cytometer) was limited to cells expressing the plasmid for the protein-BAP fusion. To demonstrate the specific linkage between FLAG expression and the presence of plasmid, the avidin positive/FLAG positive population was sorted directly onto YPD plates (a non-selective, rich media). Two days later the colonies were replicate plated onto media only selective for cells that contain the FLAG/BAP fusion plasmid. It was demonstrated that plasmid positive cells were enriched to 10% of the total population in the sorted cells for an overall enrichment of 30-fold. This experiment shows that the display method described here does maintain the phenotype/genotype linkage necessary for protein engineering applications.

Example 3: Surface Display and Selection of IgG

The usefulness of the display system in isolating proteins that can bind a specific antigen was tested in a "mock selection". Yeast strain JKI100 (matα, GAL1 promoter BirA ligase::URA3, GAL1 promoter protein disulfide isomerase::LEU2, pep4::HIS, prb1Δ, trp1) was transformed with a CEN plasmid carrying both chains of one of two IgGs (some cells transformed with IgG-A and some transformed with IgG-B). In these constructs the heavy chain is fused to the N-terminus of the biotin acceptor peptide (BAP) and the light chain is fused to the C-terminus of a FLAG tag. Yeast were grown overnight in 5 mL SD-CAA media at 30° C. The culture was spun down and resuspended in 5 mL YPG/bovine serum albumin+2.5 μg/mL biotin supplement and grown under shaking for seven hours at 20° C. The cells were removed and mixed in a ratio of 1:10,000 IgG-A to IgG-B (one IgG-A expressing cell for every 10,000 IgG-expressing cell). One $OD_{600}$ mL of the mixture ($1 \times 10^7$ cells) was removed and washed three times in 1 mL carbonate buffer (pH=8.4). Cells were resuspended in 40 μl 0.1 mg/μl NHS-PEG-biotin in carbonate buffer and incubated for 30 minutes at room temperature. After three washes in 1 mL PBS/BSA cells were incubated in 50 μl of 20 mg/mL avidin for ten minutes, twice. Cells were inoculated into 3 mL biotin-less display media YPG/BSA/PEG (30 μl of 100 mg/mL avidin with 3 mL biotin-less filter-sterilized YPG/BSA/PEG (10 wt % PEG)) and incubated in 2 wells of a six well plate overnight at 20° C.

Cells were washed off the bottom of the well with 1 mL PBS/BSA and spun down then washed three times with 1 mL cold PBS/BSA. Cells were incubated in a 1:20 dilution of 1 uM His6 tagged IgG-A antigen. Cells were then labeled by incubation in 50 μl 1:50 dilution chicken anti FLAG antibody for 20 minutes on ice and 1:50 dilution of mouse anti-His6 antibody. Cells were washed once in 500 μl PBS/BSA and then incubated in 50 μl 1:100 dilution goat anti-chicken Alexa488 and 1:30 dilution of goat anti-mouse PE for 20 minutes on ice. After a wash in 500 μl PBS/BSA, cells binding IgG-A antigen were sorted by FACS and collected in 5 mL SD-CAA. The cells were expanded, induced, put through the selection assay, and then sorted an additional time for a total of two rounds of selection. Cells from the final sort were expanded, and their DNA prepped for sequencing. Sequencing analysis showed that the IgG-A clone had been enriched 9,800-fold over the IgG-B expressing clone. A control consisting of an equimolar mixture of the clones in which all IgG expressing cells were taken in the two rounds of selection was also performed to normalize for IgG-A selection that might have occurred independent of the surface display and sorting. This control showed that no such selection occurred, and the enrichment was due to the IgG-A antigen labeling only.

Example 4: Surface Display of scFv

Yeast strain JKI100 (matα, GAL1 promoter BirA ligase::URA3, GAL1 promoter protein disulfide isomerase::LEU2, pep4::HIS, prb1Δ, trp1) was transformed with a CEN plasmid carrying a single chain antibody recognizing either antigen A or antigen B. The fusion protein was engineered to have a biotin acceptor peptide fused at the C-terminus of the variable domain light chain which is fused to the C-terminus of the variable domain heavy chain fused to the C-terminus of a FLAG tag.

After transformation, the yeast transformants were mixed in a ratio of 1 cell of antigen-A binding scFv to 10,000 antigen-B binding cells. The mixture followed the same treatments, rounds of selection, and controls as those in Example 3. Antigen A-binding yeast cells were enriched 110-fold over two rounds of FACS.

Example 5: Surface Display of IgG with Nocodozole Treatment

Nocodozole treatment is performed to increase the percentage of avidin labeled cells in a population by inhibiting cell cycle. Yeast strain JKI100 (matα, GAL1 promoter BirA ligase::URA3, GAL1 promoter protein disulfide isomerase::LEU2, pep4::HIS, prb1Δ, trp1) was transformed with a CEN plasmid carrying both chains of an IgG. The heavy chain is fused to the N-terminus of the biotin acceptor peptide (BAP) and the light chain is fused to the C-terminus of a FLAG tag. Yeast were grown overnight in 5 mL SD-CAA media at 30°

C. The culture was spun down and resuspended in 5 mL YPG/bovine serum albumin and 2.5 µg/mL biotin supplement and grown under shaking for seven hours at 20° C. One $OD_{600}$ mL of cells ($1 \times 10^7$ cells) was removed and washed three times in 1 mL carbonate buffer (pH=8.4). Cells were resuspended in 40 µl 0.1 mg/µl NHS-PEG-biotin in carbonate buffer and incubated for 15 minutes at room temperature. After three washes in 1 mL PBS/BSA, cells were incubated in 50 µl of 20 mg/mL avidin for ten minutes. 0.3 mL of cells were inoculated into 1.2 mL biotin-less display media YPG/BSA/PEG (30 µl 100 mg/mL avidin with 3 mL biotin-less filter-sterilized YPG/BSA/PEG (10 wt % PEG)) with 0 µg/mL nocodozole or 20 µg/mL nocodozole and incubated in 2 wells of a six well plate overnight at 20° C. Cells were washed off the bottom of the well with 1 mL PBS/BSA and spun down then washed three times with 1 mL cold PBS/BSA. Cells were incubated in a 1:20 dilution of 1 uM His6 tagged antigen. Cells were then labeled by incubation in 50 µl 1:50 dilution chicken anti FLAG antibody for 20 minutes on ice and 1:50 dilution of mouse anti His6 antibody. Cells were washed once in 500 µl PBS/BSA and then incubated in 50 µl 1:100 dilution goat anti-chicken Alexa488 and 1:30 dilution of goat anti-mouse PE for 20 minutes on ice. In addition to the FLAG and antigen labeling described above, cells were labeled with 50 µl 50 nM biotin-fluorescein to test what fraction of yeast cells possesses avidin on their surface.

30% of the cells not treated with nocodazole do not possess surface labeled avidin. These cells are probably daughter cells that did not inherit the avidin from their mothers. The cells treated with 20 ug/mL nocodazole possessed only 5% unlabeled avidin cells (FIGS. 12A-12D). Labeling with the antigen and anti-FLAG antibody showed that the expression and binding ability of the displayed protein was minimally perturbed by the treatment. In addition, similar experiments were carried using treatments of hydroxyurea at 200 mM and 50 mM concentrations, EGTA at 5 mM concentration, and farnesol at 25 uM. These treatments also retarded cell division by varying amounts without significantly impacting expression or function of the displayed protein.

Example 6: Surface Expression of Biotinylated Cell Wall Protein

Figure 4B:
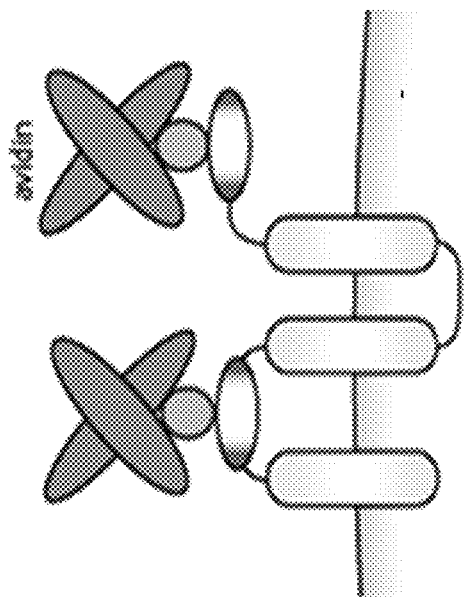
FIGS. 4A-4D illustrate an embodiment where an engineered cell wall protein fused to two biotin acceptor peptides (BAP) is expressed at the cell surface.
Figure 4A:
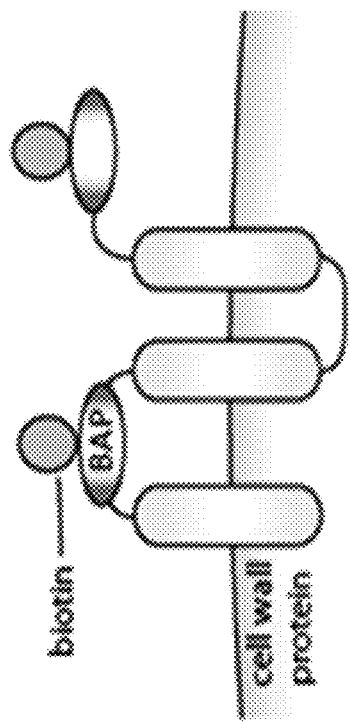
Figure 4D:
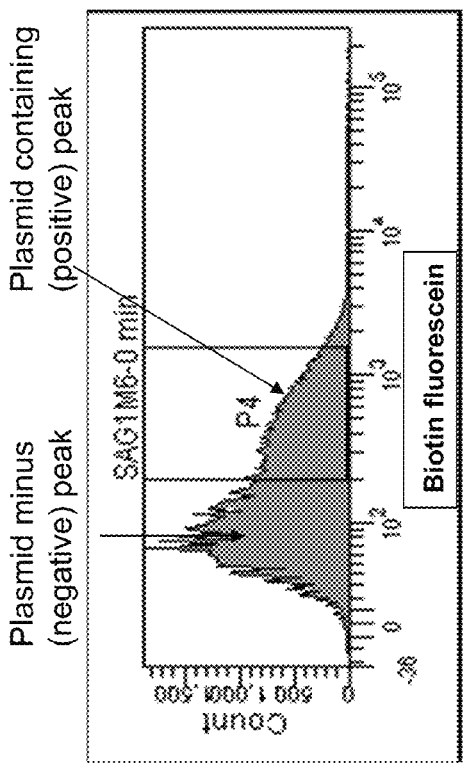
Figure 4C:
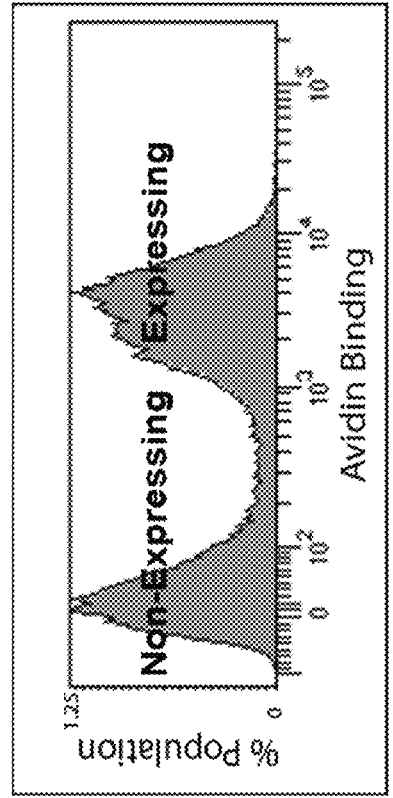

Yeast strain JKI100 (matα, GAL1 promoter BirA ligase::URA3, GAL1 promoter protein disulfide isomerase::LEU2, pep4::HIS, prb1Δ, trp1) was transformed with a CEN plasmid carrying a mutant of the cell wall protein SAG1 containing a biotin acceptor peptide in the extracellular domain (FIG. 4B). Yeast were grown overnight in 5 mL SD-CAA media at 30° C. The culture was spun down and resuspended in 5 mL YPG/bovine serum albumin and 2.5 µg/mL biotin supplement and grown under shaking for seven hours at 20° C. After an overnight incubation at 30° C., the cells were washed three times with 1 mL cold PBS/BSA. Cells were incubated in 20 mg/mL avidin for ten minutes, twice, then washed once in 1 mL PBS/BSA. Cells were then labeled with 50 µl 50 nM biotin-fluorescein and analyzed by flow cytometry to highlight cells displaying the biotinylated SAG1 protein (P4, FIG. 4D). Because CEN plasmids are unstable in yeast, a significant portion of the cells do not display the biotinylated SAG1 protein. These cells are the negative peak in the FIG. 4D. This instability also serves as an internal negative control to demonstrate that avidin and biotin-fluorescein labeling is exclusive to cells expressing the biotin-SAG1 protein.

Example 7: Selection of Thermostable Protein Mutants

Yeast strain JKI100 (matα, GAL1 promoter BirA ligase::URA3, GAL1 promoter protein disulfide isomerase::LEU2, pep4::HIS, prb1Δ, trp1) was transformed with a CEN plasmid carrying one of two small, single domain protein mutants. One mutant has a melting temperature of 42° C. as determined by differential scanning calorimetry. The other mutant has a melting temperature of 82° C. determined by DSC. Both of these mutant proteins were expressed as C-terminal fusions to the BAP biotin acceptor peptide and N-terminal fusions to the FLAG tag.

Figure 10B:
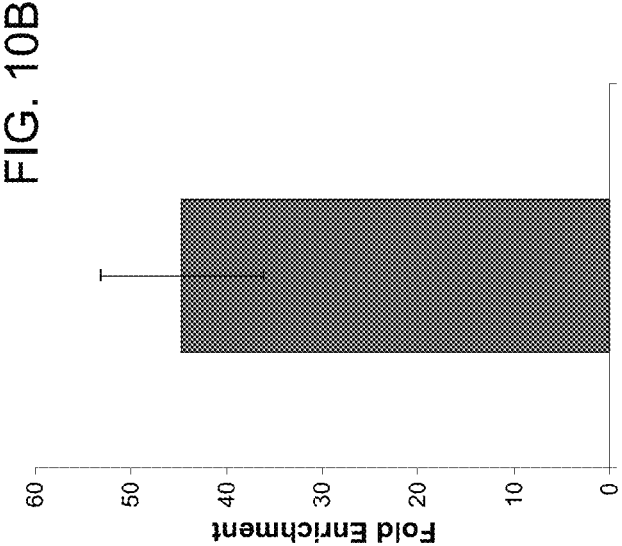
FIG. 10B shows a non limiting embodiment of the fold enrichment of thermostable protein mutants.
Figure 10A:
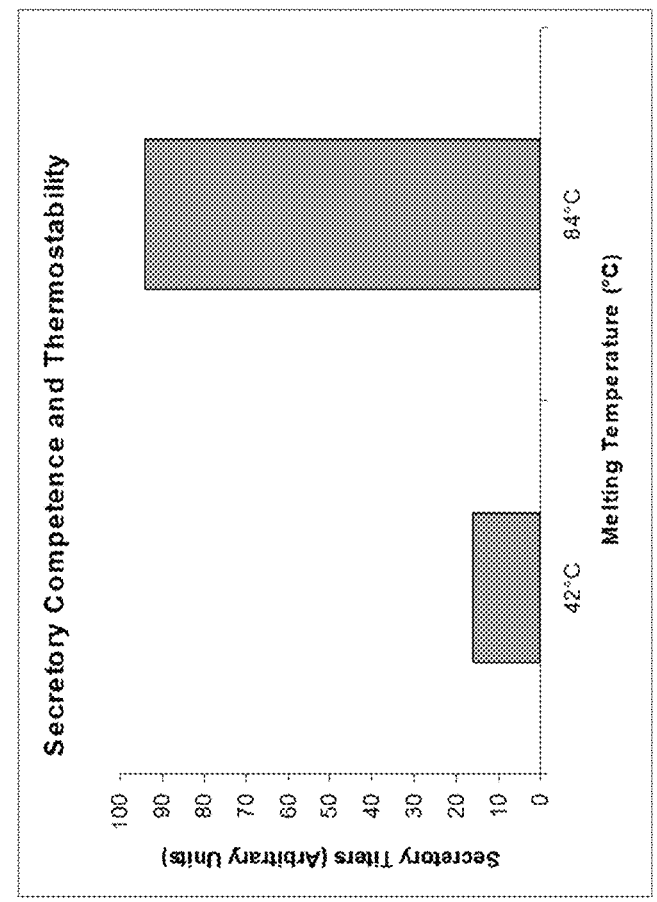
FIG. 10A shows a non limiting embodiment of the selection of thermostable protein mutants.
Figure 11A:
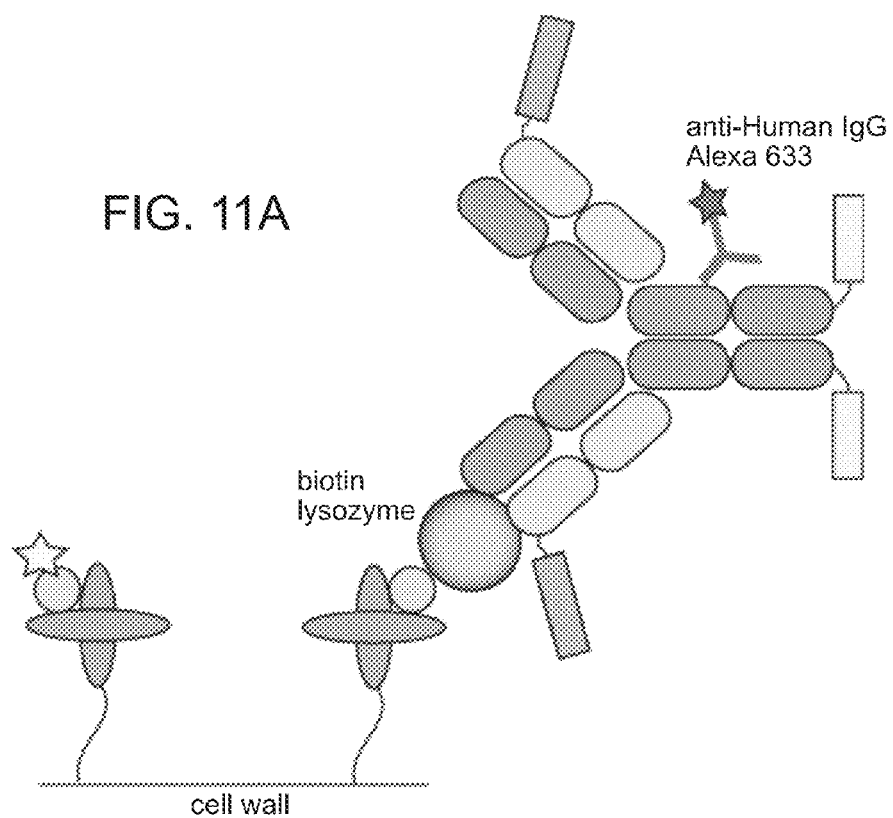
FIG. 11A shows a non-limiting embodiment of antibody expression and display at the cell surface.
Figure 11B:
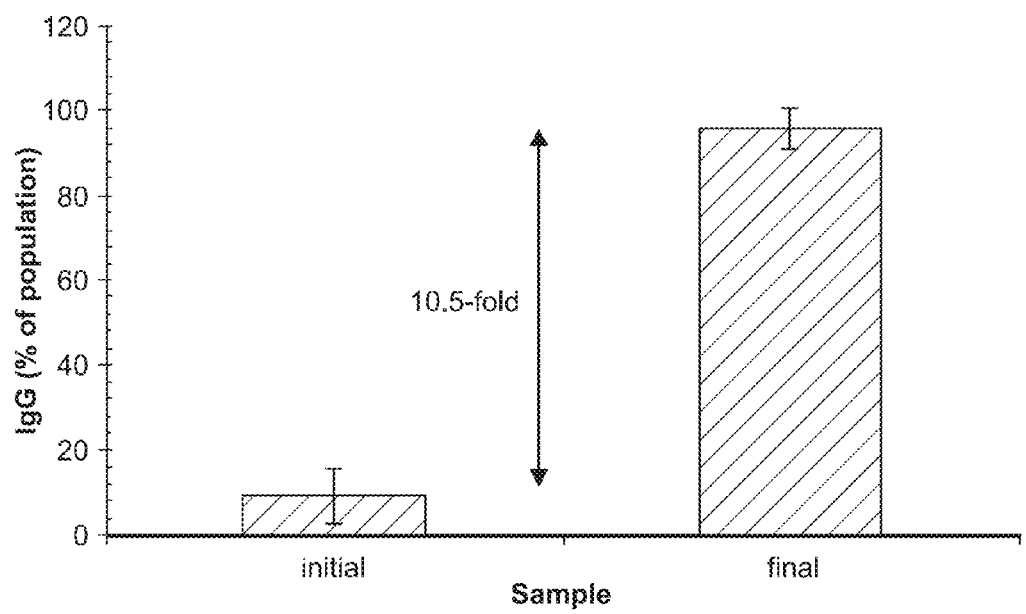
FIG. 11B shows a non-limiting embodiment of antibody expression and display at the cell surface and enrichment of the antibody population.
Figure 11C:
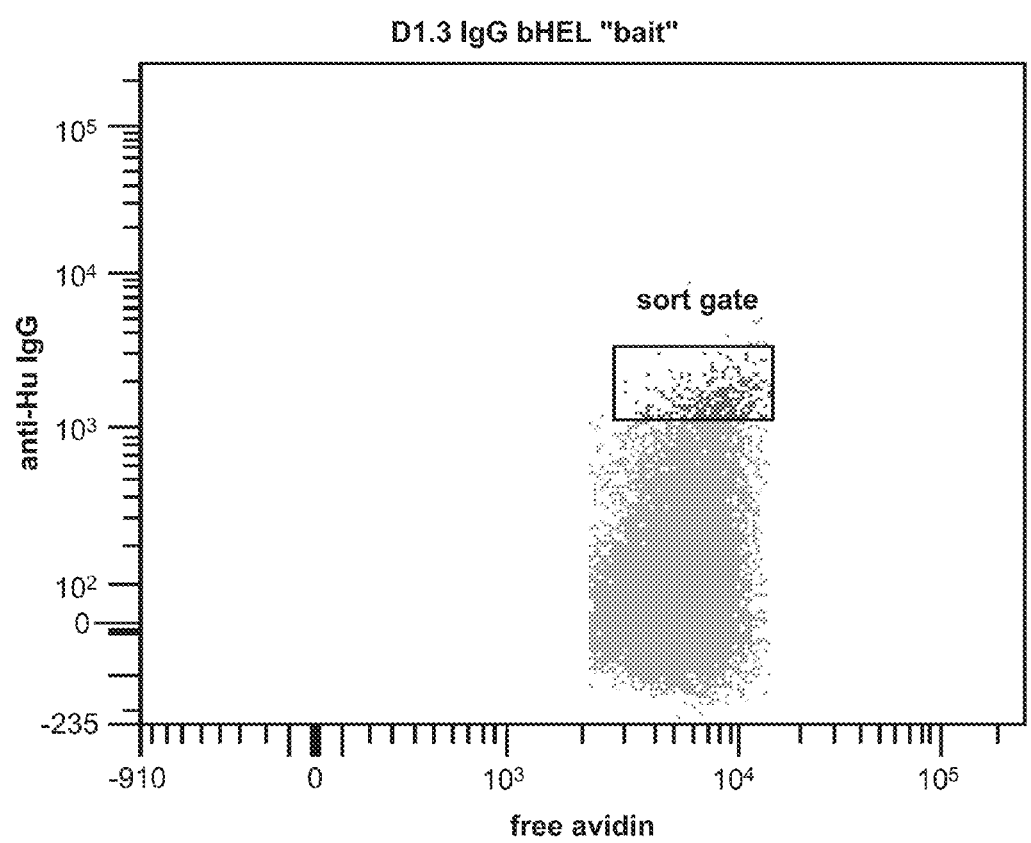
FIG. 11C shows a non-limiting embodiment of antibody expression and display at the cell surface and enrichment of the antibody population.
Figure 12A:
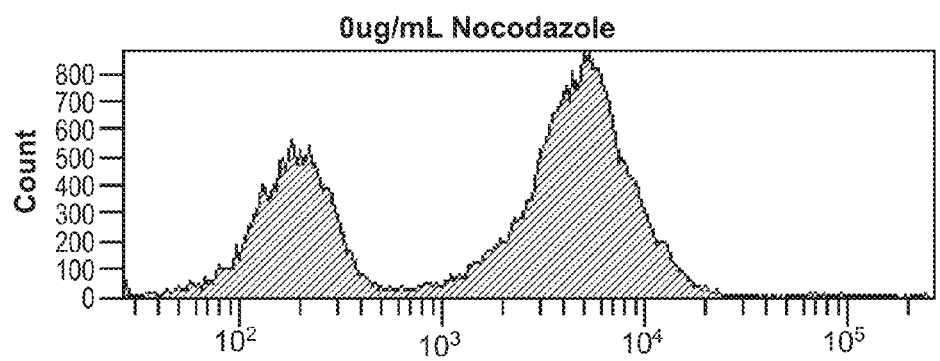
FIGS. 12A-12D show a non-limiting embodiment of protein display and cell cycle inhibition.
Figure 12B:
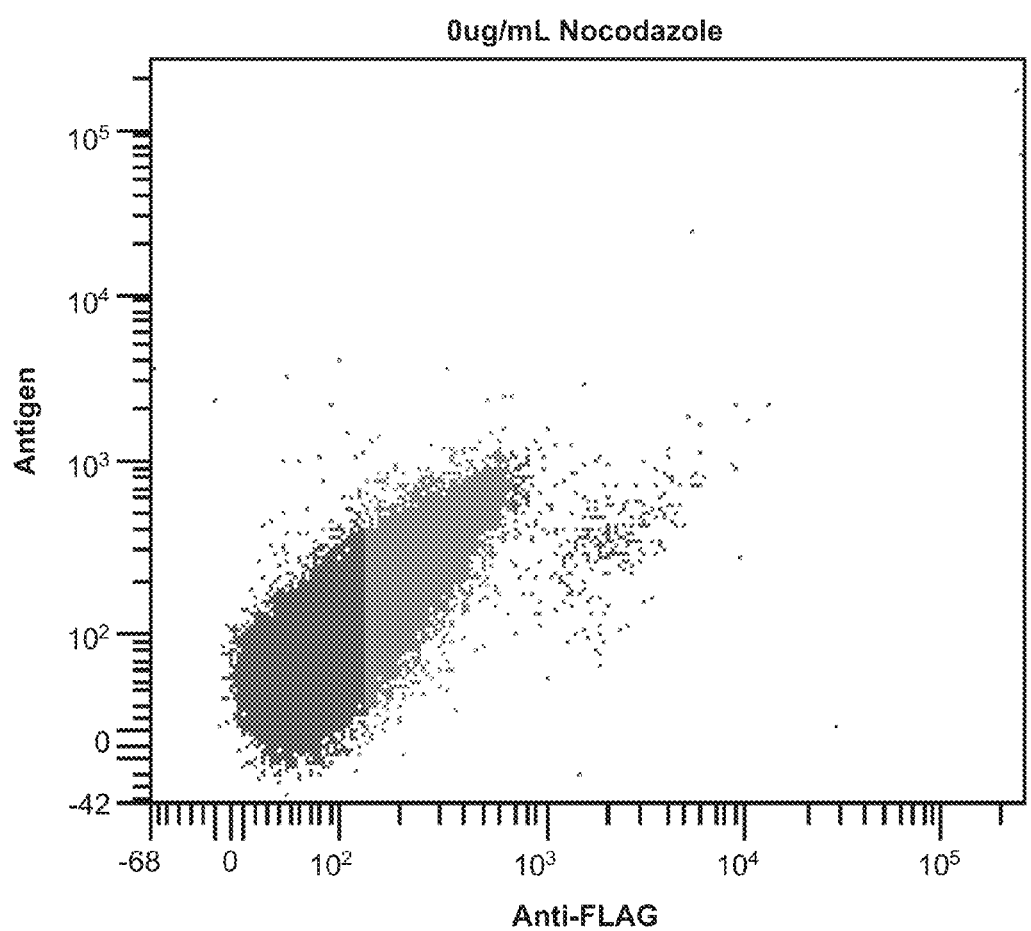
Figure 12C:
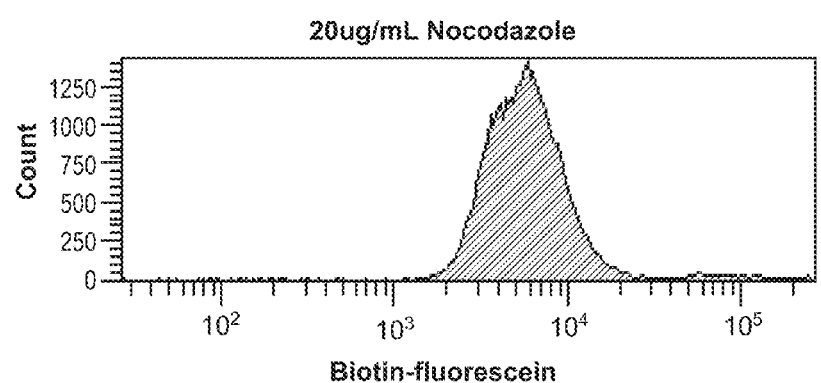
Figure 12D:
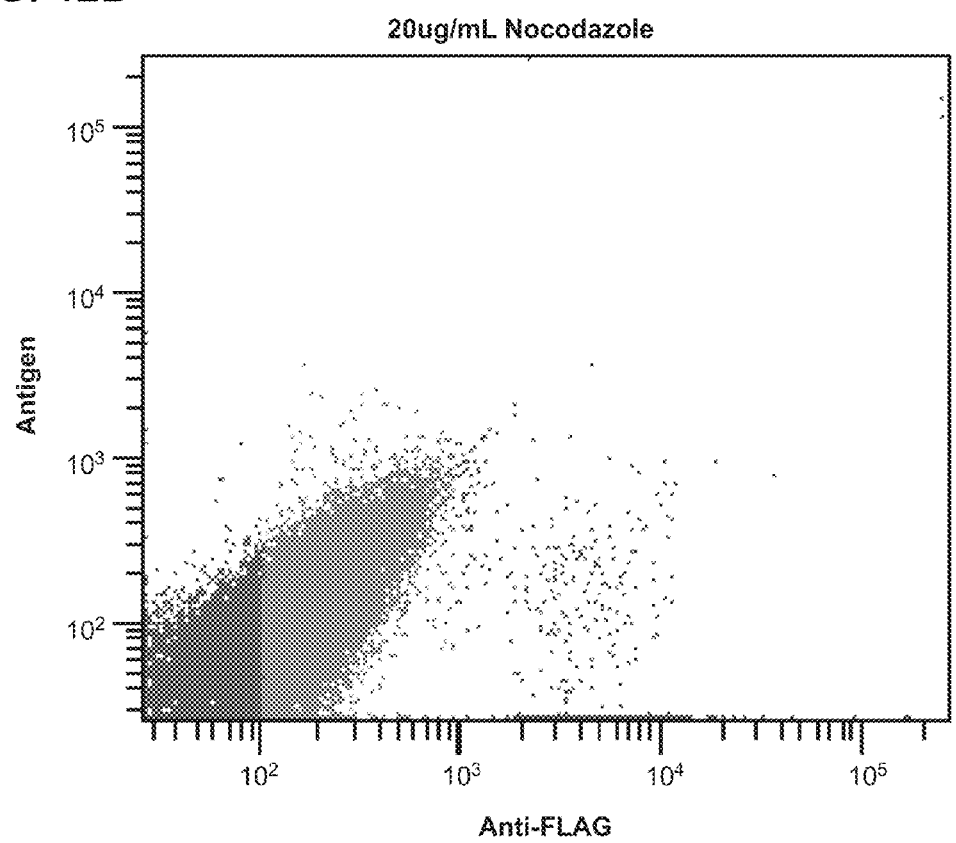

After transformation, the yeast transformants were mixed in a ratio 1 cell of the more thermostable mutant to 100 cells of the less thermostable mutant. The mixture followed the same treatments, rounds of selection, and controls as those in Example 3 except only FLAG tag was labeled and used as a criterion for selection. After two rounds of selection, isolated clones were sequenced, and it was determined that the more thermostable clone was enriched 45-fold over the less thermostable clone (FIGS. 10A and 10B).

Example 8: DNA Attachment to Cell Surface for Directed Evolution of DNA Modifying Enzymes Directed Evolution has been a successful strategy for engineering proteins with enhanced binding or activity characteristics. Most directed evolution of DNA modifying proteins such as polymerases has been done in bacteriophage or in emulsions of cell lysate (Tawfik D, Griffiths A. "Man-made Cell-like Compartments for Molecular Evolution." *Nature Biotechnology* 1998, 16:652-656; Ghadessy F., Ong, J., Holliger, P., "Directed Evolution of Polymerase Function by compartmentalized Self-replication." PNAS USA 2001, 98:4552-4557; Ong, J. L., Loakes, D., Jaroslawski, S., Too, K., Holliger, P., "Directed Evolution of DNA Polymerase, RNA Polymerase, and Reverse Transcriptase Activity in a Single Polypeptide." *Jour. Mol. Biol.* (2006), 361: 537-550; Jestin, J. L., Kristensen, P., Winter, G. "A Method for the Selection of Catalytic Activity Using Phage display and Proximity Coupling." *Angew Chem. Int Ed Engl* 1999, 38: 1124-2237; Brunet, E., Chauvin, C., Choumet, V., Jestin, J. L. "A Novel Strategy for the Functional Cloning of Enzymes Using Filamentous Phage Display: the Case of Nucleotidyl Transferases." *Nucleic Acids Res* 2002, 30:e40; Xia, G., Chen, L., Sera, T., Fa, M., Schultz, P., Romesberg, F. "Directed Evolution of Novel Polymerase Activities: Mutation of a DNA Polymerase into an efficient RNA Polymerase." *PNAS USA* 2002, 99:6597-6602; Fa, M., Radeghieri, A., Henry, A., Romesberg, F. "Expanding the Substrate Repertoire of a DNA Polymerase by Directed Evolution." *J American Chem. Society* 2004, 126: 1748-1754). In the former case, selection relies on the ability of the polymerase to incorporate a biotinylated substrate. In the latter case, the selection relies on the ability of the polymerase to completely transcribe its own gene while incorporating novel base pairs or catalytic activity. Consequently, these approaches are limited to cases where biotinylated dNTP incorporation or polymerase processivity is essential, or at least tolerated. A new selection system is presented, which overcomes earlier limitations and allows for the selection of polymerases that use many different dNTPs, or to select for polymerases with lower processivity. The technique outlined in FIGS. 13-16 links a DNA oligo to cells via a high affinity biotin/avidin interaction. Once attached to the cell, the DNA can interact with enzymes that are displayed on the cell surface as well or that are secreted into the supernatant.

Figure 13:
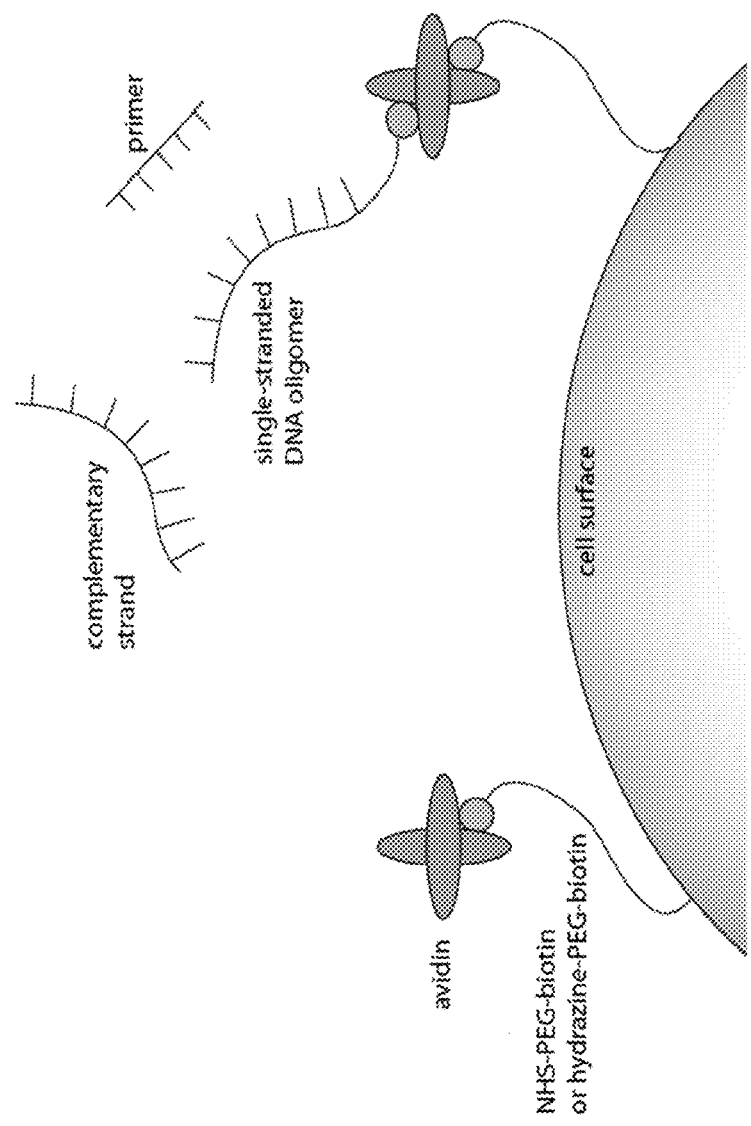
FIG. 13 shows a non-limiting embodiment of a substrate displayed on a cell. IN one embodiment a cell labeled with NHS-PEG-biotin or hydrazine-PEG-biotin is provided. Upon subsequent addition and binding of avidin, a biotinylated oligonucleotide is added and immobilized on the cell surface. In a next step a complementary strand or extension primer can be supplied. In on embodiment, enzymatic chemistry can be performed on the surface linked DNA construct by surface expressed enzymes.

Nucleic Acid Attachment to the Cell Surface (FIG. 13)

To use nucleic acid in display-based screening, nucleic acid is physically attached to the cell. The biotin/avidin interaction, being extremely high affinity ($K_d \sim 10^{-15}$ M), is well suited to attach DNA to the cell surface. The biotin/avidin interaction has been used previously to immobilize proteins on the cell surface (Manz, R., Assenmacher, M., Pfluger, E., Miltenyi, S., Radbruch, A. "Analysis and Sorting of Live Cells According to Secreted Molecules, Relocated to Cell-Surface Affinity Matrix." (1995) *PNAS*, 92(6): 1921-1925; Rakestraw A., Baskaran, A., Wittrup, K. D., "A Flow Cytometric Assay for Screening Improved Heterologous Protein Secretion in Yeast." (2006) *Biotechnology Progress*, 22(4): 1200-1208). Cells are labeled with biotin using a polyethylene glycol (PEG) linker. In one form this linker possesses biotin on one end and a free amine reactive N-succinimidyl ester (NHS) group on the other. In this manner biotin can be directly conjugated to proteins on the cell surface in an alkaline buffer. Biotin can also be attached to carbohydrate on the cell wall, thereby preserving the integrity of cell surface proteins. For this alternative the cells are treated with periodate (a compound that opens the carbohydrate ring and oxidizes adjacent hydroxyls into aldehydes) or an enzyme, such as galactose oxidase, that similarly but non-chemically opens carbohydrate ring structures. After treatment, the cells are labeled with biotin-polyethylene glycol-hydrazide which covalently links the biotin to the surface via the exposed aldehydes on the oxidized sugars. After labeling the cells with NHS-PEG-biotin or hydrazide-PEG-biotin, the labeled cells are exposed to avidin resulting in the binding of avidin to biotin. Because avidin is tetravalent, it can accept up to three additional biotin molecules. Nucleic acid strands can therefore be bound to the avidin by biotin conjugated to the 3' or 5' ends of a nucleic acid oligomer. For example, if a single stranded DNA oligomer is attached to avidin, the complementary strand or primer can be annealed, or modifications using single strand DNA as a substrate can be performed. Annealing of the complementary strand generates double stranded DNA, which can be subjected to enzymatic processes such as restriction cleavage or primer extension (FIG. 15 and FIGS. 16A and 16B) Immobilized DNA allows for the evaluation of a variety of enzymes. For instance polymerase activity can be detected by the incorporation of fluorescent oligonucleotides. The use of fluorescent complementary oligos or dNTPs, allows for the screening of enzyme activity of both surface displayed proteins and proteins in the supernatant. Cells can be isolated by flow cytometry allowing for the selection of enzymes with optimized properties. A variety of different moieties can be attached to the cell surface via the avidin linkage, including biotinylated RNA, peptides, and full length protein. This methodology thus provides a means to evaluate many different types of protein and enzymatic interactions on the surface of cells.

Biotinylated Oligo Attachment

Yeast were labeled with NHS-PEG-biotin and avidin in preparation for oligonucleotide attachment. A 5' biotinylated single-stranded oligo was added to be immobilized on the yeast surface via the avidin sandwich. The attached oligonucleotide was detected by annealing a FAM (6-carboxyfluorescein) fluorescent labeled complementary strand to the cell surface. Flow cytometry data for a complementary and non-complementary FAM labeled oligonucleotide are shown in FIGS. 14A and 14B.

On Cell Restriction Digest

Figure 15:
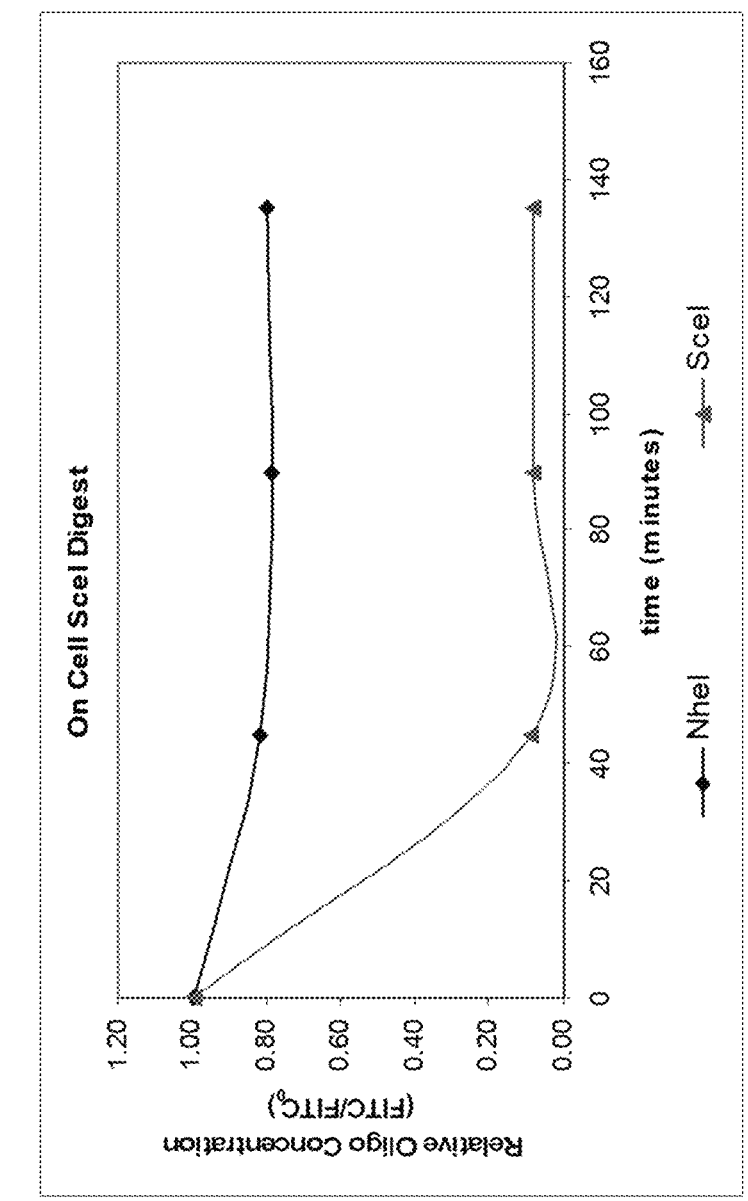
FIG. 15 shows a non-limiting embodiment depicting the decrease of a fluorescent signal over time of a surface attached FAM labeled double stranded oligonucleotide comprising an I-SceI restriction site, which was incubated with NheI or SceI. The resulting oligonucleotide cleavage was indicated by decreased FAM fluorescence; and, FIG. 16A shows a non-limiting embodiment of a fluorescent signal of a primer that was extended on a single-stranded DNA template attached to the surface of yeast. The fluorescent signal shows the incorporation of Cy-5 labeled dNTP by Klenow fragment.

The annealed double stranded oligo contains an I-SceI endonuclease site. The cells were incubated with I-SceI and analyzed by flow cytometry. As the DNA was cleaved, the fluorophores was released from the surface causing a decrease in FAM signal over time (FIG. 15). Treatment with NheI was used as a negative control.

On Cell Primer Extension

Figure 16A:
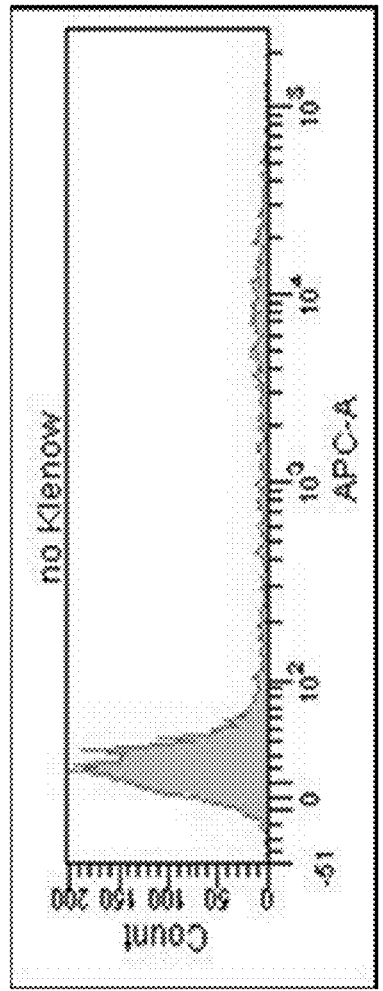
FIG. 16B shows a non-limiting embodiment of a fluorescent signal of a primer in the absence of Klenow fragment.
Figure 16B:
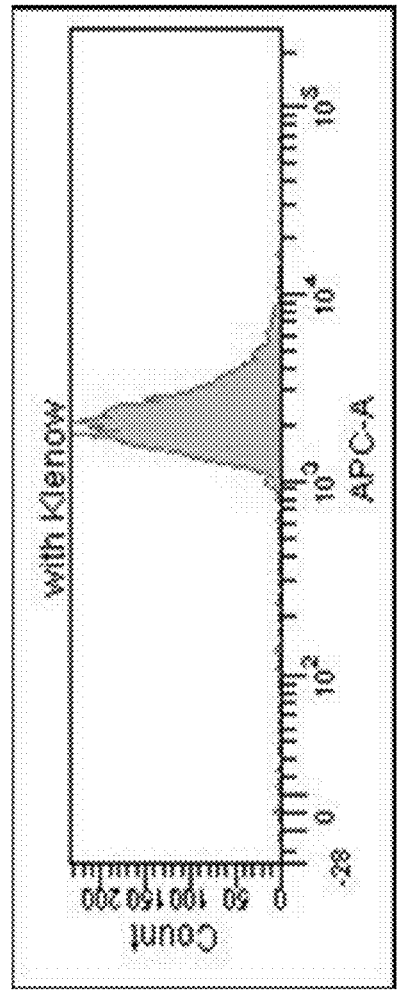

A small complementary primer was annealed to an oligo, which was immobilized on the surface of a yeast cell. The yeast were subsequently incubated in PCR buffer containing dNTPs including 25 μM dUTP-Cy5 fluorescent dye. When Klenow fragment polymerase was added to the mixture, the primer was extended allowing the surface construct to incorporate the fluorescent dye as indicated by flow cytometry (FIG. 16B).

The foregoing written specification is considered to be sufficient to enable one skilled in the art to practice the invention. The present invention is not to be limited in scope by examples provided, since the examples are intended as a single illustration of one aspect of the invention and other functionally equivalent embodiments are within the scope of the invention. Various modifications of the invention in addition to those shown and described herein will become apparent to those skilled in the art from the foregoing description and fall within the scope of the appended claims. The advantages and objects of the invention are not necessarily encompassed by each embodiment of the invention.

The contents of all references, patents and published patent applications cited throughout this application are incorporated herein by reference in their entirety.

What is claimed is:

1. A protein screening method comprising:
   a. expressing an engineered protein comprising a protein of interest fused to a first secretion leader peptide at the N-terminus of the protein of interest and a modification motif in a eukaryotic host cell having a cell surface and expressing a coupling enzyme in the eukaryotic host cell,
   wherein the host cell has a first binding partner coupled to the extracellular side of the host cell surface,
   wherein the modification motif is a biotinylation motif,
   wherein the first binding partner is an avidin protein, a streptavidin protein, or a variant thereof capable of binding a second binding partner,
   wherein the second binding partner is biotin or a biotin analog capable of binding avidin, streptavidin or variant thereof,
   wherein the first secretion leader peptide is a peptide that directs proteins to the eukaryotic secretory pathway,
   wherein the coupling enzyme catalyzes coupling of the second binding partner to the biotinylation motif,
   wherein the coupling enzyme is fused to a second secretion leader peptide at the N-terminus of the coupling enzyme,
   wherein the second secretion leader peptide is a peptide that directs proteins to the eukaryotic secretory pathway,
   wherein the second binding partner is coupled intracellularly to the modification motif of the expressed engineered protein, and
   wherein expression of the engineered protein results in secretion of the protein of interest coupled to the second binding partner and further results in the non-covalent binding of the second binding partner to the first binding partner; and,
   b. evaluating a property of the protein of interest displayed on the extracellular side of the host cell surface.

2. The method of claim 1, wherein the evaluating step comprises assaying a level of activity of the protein of interest, determining whether the protein of interest has a predetermined function, comparing the property of the protein of interest to the property of a reference protein, determining the amount of the protein of interest displayed on the cell surface, or any combination thereof.

3. The method of claim 1, wherein the protein of interest is an antibody, a single chain antibody, a scaffold protein, or a fragment thereof, and the property of the protein of interest being evaluated is the binding affinity of the protein of interest to a target molecule, wherein the target molecule comprises an antigen and/or epitope.

4. The method of claim 1, further comprising selecting one or more host cells on the basis of a first predetermined property of the displayed protein of interest.

5. The method of claim 4, further comprising selecting one or more of the host cells on the basis of a second predetermined property of the displayed protein of interest.

6. The method of claim 4, further comprising releasing the protein of interest from one or more selected host cells displaying at least a predetermined level of the protein of interest.

7. The method of claim 1, wherein the eukaryotic host cell is a yeast cell.

8. The method of claim 1, wherein the first binding partner interacts with the second binding partner with an affinity of from about $10^{-7}$M to about $10^{-15}$M.

9. The method of claim 1 comprising displaying a plurality of different proteins of interest, wherein each different protein of interest is expressed in a different host cell.

10. The method of claim 9, wherein the different proteins of interest are sequence variants of each other.

11. The method of claim 1, wherein the first binding partner is an avidin protein.

12. The method of claim 11, wherein the second binding partner is biotin.

13. The method of claim 1, wherein the second binding partner is biotin.

14. The method of claim 1, wherein the protein of interest is an antibody or antibody fragment, and the property of the protein of interest being evaluated is the binding affinity of the antibody or antibody fragment to an antigen.

15. The method of claim 1, further comprising selecting one or more host cells displaying the protein of interest, the protein of interest having a predetermined affinity for a target molecule, wherein the protein of interest is an antibody, a single chain antibody, a scaffold protein, or a fragment thereof, and wherein the target molecule comprises an antigen and/or epitope.

16. The method of claim 15, further comprising releasing the protein of interest from one or more selected host cells.

17. The method of claim 4, further comprising releasing the protein of interest from one or more selected host cells displaying the protein of interest having the first predetermined property.

* * * * *